United States Patent
Zhang et al.

(10) Patent No.: US 11,648,320 B2
(45) Date of Patent: May 16, 2023

(54) NON-COVALENTLY ASSEMBLED BIOMATRIX LAYER

(71) Applicant: DENOVOMATRIX GMBH, Dresden (DE)

(72) Inventors: Yixin Zhang, Dresden (DE); Alvin Thomas, Dresden (DE); Richard Wetzel, Dresden (DE); Dejan Husman, Dresden (DE); Robert Wieduwild, Dresden (DE)

(73) Assignee: DENOVOMATRIX GMBH, Dresden (DE)

( * ) Notice: Subject to any disclaimer, the term of this patent is extended or adjusted under 35 U.S.C. 154(b) by 435 days.

(21) Appl. No.: 16/622,960

(22) PCT Filed: Jun. 18, 2018

(86) PCT No.: PCT/EP2018/066145
§ 371 (c)(1),
(2) Date: Dec. 16, 2019

(87) PCT Pub. No.: WO2018/229304
PCT Pub. Date: Dec. 20, 2018

(65) Prior Publication Data
US 2021/0145980 A1 May 20, 2021

(30) Foreign Application Priority Data
Jun. 16, 2017 (EP) ..................................... 17176355

(51) Int. Cl.
| | |
|---|---|
| *A61K 47/69* | (2017.01) |
| *A61K 47/64* | (2017.01) |
| *A61K 47/60* | (2017.01) |
| *C12N 5/00* | (2006.01) |

(52) U.S. Cl.
CPC .......... *A61K 47/6903* (2017.08); *A61K 47/60* (2017.08); *A61K 47/6435* (2017.08); *C12N 5/0068* (2013.01); *C12N 2500/32* (2013.01); *C12N 2533/40* (2013.01)

(58) Field of Classification Search
CPC ................ A61K 47/6903; A61K 47/60; A61K 47/6435; C12N 5/0068; C12N 2500/32; C12N 2533/40
See application file for complete search history.

(56) References Cited

U.S. PATENT DOCUMENTS

2012/0052579 A1* 3/2012 Shannon ................ C12M 23/20
525/54.1
2015/0246132 A1* 9/2015 Wieduwild ............ A61K 35/33
514/56

FOREIGN PATENT DOCUMENTS

WO 2014040591 3/2014

OTHER PUBLICATIONS

F. Taraballi, et al. Glycine-spacers influence functional motifs exposure and self-assembling propensity of functionalized substrates tailored for neural stem cell cultures, Frontiers in Neuroengineering, Feb. 2010, vol. 3, Article 1, 1-9. (Year: 2010).*
Robert Wieduwild et al: "Noncovalent Hyrogel Beads as Microcarriers for Cell Culture", Angewandte Chemie International Edition, vol. 54, No. 13, Feb. 4, 2015, p. 3962-3966.
Christoph Tondera et al: "In Vivo Examination of Injectable Hydrogel System Crosslinked by Peptide-Oligosaccharide Interaction in Immunocompetent Nude Mice", Advanced Functional Materials, vol. 27, No. 15, Apr. 1, 2017, p. 1605189.
Robert Wieduwild et al: "Minimal Peptide Motif for Non-covalent Peptide-Heparin Hydrogels", Journal of the American Chemical Society, vol. 135, No. 8, Feb. 6, 2013, pp. 2919-2922.

* cited by examiner

*Primary Examiner* — Michael P Cohen
(74) *Attorney, Agent, or Firm* — JMB Davis Ben-David

(57) ABSTRACT

The present invention provides a biomatrix layer comprising, consisting essentially of or consisting of a sulfated oligosaccharide at a concentration in the range of 0.1 μM to 1,000 μM and a peptide-polyethylene glycol-conjugate according to formula (I): PEG-R1-(BX)n (I) wherein B is lysine or arginine, X is selected from alanine, glycine, serine, threonine, tyrosine, glutamic acid or aspartic acid and n is an integer selected from 3, 4, 5, 6, 7, 8, 9, 10, 11, 12, 13, 14, 15, 16, 17, 18, 19 and 20; $R_1$ may be absent or is a peptide comprising 5 to 30 amino acids; PEG is comprised at a concentration in the range of 0.1 μM to 1,000 μM; R1, if present, is comprised at a concentration in the range of 0.1 μM to 4,000 μM; (BX)n is comprised at a concentration in the range of 0.25 μM to 1,000 μM. The invention further relates to processes for assembling the biomatrix layer. The biomatrix layer can be used in various biomedical applications, such as neuroprostheses, biosensors, nerve grafts, cell culture and encapsulation of cells and microorganisms as well as for drug delivery.

15 Claims, 15 Drawing Sheets
Specification includes a Sequence Listing.

Conventional hydrogel protocol
Concentrated components

Biomatrix layer protocol
Diluted components

NON-COVALENTLY ASSEMBLED BIOMATRIX LAYER

CROSS-REFERENCE TO RELATED APPLICATIONS

This is the U.S. National Stage of International Patent Application No. PCT/EP2018/066145 filed on Jun. 18, 2018, which claims priority to European Patent Application No. 17176355.0 filed on Jun. 16, 2017.

FIELD OF THE INVENTION

The present invention provides a biomatrix layer with a thickness in the range from 3 nm to 40 µm, comprising, consisting essentially of or consisting of a negatively charged polymer (NCP) at a concentration in the range of 0.1 µM to 1,000 µM and a peptide-polyethylene glycol-conjugate at a concentration in the range of 0.1 µM to 1,000 µM. The invention further relates to processes for assembling the biomatrix layer. The biomatrix layer can be loaded with cells and organoids. Several characteristics of the biomatrix layer, such as thickness, stiffness and porosity are adjustable by selecting the type of the NCP and the peptide-polyethylene glycol-conjugate and adjusting the concentrations thereof during preparation of the biomatrix layer. The invention provides a combinatorial library of negatively charged polymer (NCP) and peptide-polyethylene glycol-conjugates, which may further contain bio-functional peptides, wherein said library enables the adjustment of the surface of the biomatrix layer for selective culture of specific cell types, coating of biomedical devices and the like. Moreover, the invention provides a kit comprising the ingredients of the combinatorial library. The biomatrix layer mimics the extracellular matrix and can be used in various biomedical applications.

BACKGROUND ART

Standard cell culture in plastic flasks does not have the capability to mimic the complexity of the natural extracellular matrix (ECM). Various chemically coated surfaces have been developed to meet the needs of specific cell types (Mei Y, Saha K, Bogatyrev S R, Yang J, Hook A L, Kalcioglu Z I, et al. Combinatorial development of biomaterials for clonal growth of human pluripotent stem cells. Nat Mater 2010, 9(9): 768-778; Celiz A D, Smith J G W, Patel A K, Hook A L, Rajamohan D, George V T, et al. Discovery of a Novel Polymer for Human Pluripotent Stem Cell Expansion and Multilineage Differentiation. Advanced Materials 2015, 27(27): 4006-4012). There are additional requirements for the development and engineering of biomaterials, e.g. to recapitulate the cell type-specific 3D environment and mechanical properties of natural ECM. Among the widely-used hydrogels, for example, Matrigel has been used as ECM-mimicking biomatrix, though it cannot be easily adjusted to the needs of specific cell types and tissues. The alterations in ECM composition have been shown to affect the repair of damaged liver tissue (Klaas M, Kangur T, Viil J, Mäemets-Allas K, Minajeva A, Vadi K, et al. The alterations in the extracellular matrix composition guide the repair of damaged liver tissue. Scientific reports 2016, 6: 27398) and the expansion of induced pluripotent stem cells (Adnan N, Mie M, Haque A, Hossain S, Mashimo Y, Akaike T, et al. Construction of a defined biomimetic matrix for long-term culture and maintenance of mouse induced pluripotent stem cells. Bioconjugate Chemistry 2016). To develop biomatrices tailored for particular applications, combinatorial libraries have been generated either through chemical syntheses (Ranga A, Gobaa S, Okawa Y, Mosiewicz K, Negro A, Lutolf M P. 3D niche microarrays for systems-level analyses of cell fate. Nature Communications 2014, 5: 4324; Klim J R, Li L, Wrighton P J, Piekarczyk M S, Kiessling L L. A defined glycosaminoglycan-binding substratum for human pluripotent stem cells. Nat Methods 2010, 7(12): 989-994; Vegas A J, Veiseh O, Doloff J C, Ma M, Tam H H, Bratlie K, et al. Combinatorial hydrogel library enables identification of materials that mitigate the foreign body response in primates. Nat Biotech 2016, 34(3): 345-352) or using ECMs from various porcine tissues (Beachley V Z, Wolf M T, Sadtler K, Manda S S, Jacobs H, Blatchley M R, et al. Tissue matrix arrays for high-throughput screening and systems analysis of cell function. Nat Meth 2015, 12(12): 1197-1204) for cell culture applications in vitro and for biocompatibility analyses in vivo.

A non-covalent hydrogel system formed by mixing heparin with 4-arm polyethylene glycol (starPEG) conjugated to heparin binding peptides has already been developed (Wieduwild R, Tsurkan M V, Chwalek K, Murawala P, Nowak M, Freudenberg U, et al. Minimal Peptide Motif for Non-Covalent Peptide-Heparin Hydrogels. J Am Chem Soc 2013, 135(8): 2919-2922). The peptides possess a simple $(BA)_n$ motif (where B is a basic residue Arg/Lys, and A is Ala), while increasing the repeat number n leads to stiffer hydrogels. The interaction between $(BA)_n$ and heparin in bulk hydrogel formation is associated with a random-coil to α-helix transformation, while the gelation time (instant to hours) is dependent on the choice of peptides and sulfated oligosaccharides (Wieduwild R, Krishnan S, Chwalek K, Boden A, Nowak M, Drechsel D, et al. Noncovalent Hydrogel Beads as Microcarriers for Cell Culture. Angew Chem Int Ed 2015, 56(13): 1521-3773). Through varying the peptide and sulfated oligosaccharide (e.g. dextran sulfate, heparin) components, the biomaterials could be tailored for applications such as 3D cell culture and drug release (WO2014040591 A2). This dynamic network showed shear-thinning and self-healing properties, which are essential for injectability. Injected hydrogels in mice have shown high biocompatibility and did not cause adverse inflammatory response (Tondera, C. et al. (2017) In Vivo Examination of an Injectable Hydrogel System Crosslinked by Peptide-Oligosaccharide Interaction in Immunocompetent Nude Mice. Adv. Funct. Mater. 27, 27, 1605189).

WO 2008/124165 A2 discloses non-covalent, self-organizing hydrogels, which are produced by coupling a dipeptide motif to a polymer chain.

Further known are low-molecular-weight heparin and a peptide bound to starPEG. A hydrogel is formed by the non-covalent bond between the peptide and heparin. The peptide, derived from HIP, contains the sequence (KA)4 (Nori Yamaguchi et al: "Rheological Characterization of Polysaccharide-Poly(ethylene glycol) Star Copolymer Hydrogels", BIOMACROMOLECULES, Vol. 6, No. 4, 28 May 2005 (2005 May 28), pages 1931-1940; Nori Yamaguchi et al: "Polysaccharide poly(ethylene glycol) star copolymer as a scaffold for the production of bioactive hydrogels", BIOMACROMOLECULES, Vol. 6, No. 4, July 2005 (2005 July), pages 1921-1930.

Generally, the formation of hydrogels which consist of a conjugate of starPEG with a heparin binding peptide and heparin or low-molecular-weight heparin is already known from U.S. Pat. No. 6,958,212 B1; Kyung Jae Jeong et al: "Interplay between Covalent and Physical Interactions within Environment Sensitive Hydrogels", BIOMACRO- MOLECULES, Vol. 10, No. 5, 23 Mar. 2009 (2009 Mar. 23), pages 1090-1099; Mikhail V. Tet al: "Enzymatically degradable heparin-polyethylene glycol gels with controlled mechanical properties", CHEMICAL COMMUNICATIONS, Vol. 46, No. 7, 16 Dec. 2009 (2009 Dec. 16), pages 1141-1143; Mikhail V. Tsurkan et al: "Modular StarPEG-Heparin-Gels with Bifunctional Peptide Linkers", MACROMOLECULAR RAPID COMMUNICATIONS, Vol. 31, No. 17, 16 Aug. 2010 (2010 Aug. 16), pages 1529-1533; Seal B. L. et al: "Physical matrices stabilized by enzymatically sensitive covalent crosslinks", ACTA BIOMATERIALIA, Vol. 2, No. 3, 1 May 2006 (2006 May 1), pages 241-251; Alison B. Pratt et al: "Synthetic extracellular matrices for in situ tissue engineering", BIOTECHNOLOGY AND BIOENGINEERING, Vol. 86, No. 1, 12 Feb. 2004 (2004 Feb. 12), pages 27-36; Brandon I. Seal et al: "Physical Polymer Matrices Based on Affinity Interactions between Peptides and Polysaccharides", BIOMACROMOLECULES, Vol. 4, No. 6, 1 Nov. 2003 (2003 Nov. 1), pages 1572-1582; Freudenberg U. et al: "A star-PEG-heparin hydrogel platform to aid cell replacement therapies for neurodegenerative diseases", BIOMATERIALS, Vol. 30, No. 28, October 2009 (2009 October), pages 5049-5060; Nie T. et al: "Production of heparin containing hydrogels for modulating cell responses", ACTA BIOMATERIALIA, Vol. 5, No. 3, March 2009 (2009 March), pages 865-875; Benoit et al: "The effect of heparin-functionalized PEG hydrogels on three-dimensional human mesenchymal stem cell osteogenic differentiation", BIOMATERIALS, Vol. 28, No. 1, 1 Jan. 2007 (2007 Jan. 1), pages 66-77; Brandon L. Seal et al: "Viscoelastic Behavior of Environmentally Sensitive Biomimetic Polymer Matrices", MACROMOLECULES, Vol. 39, No. 6, 23 Feb. 2006 (2006 Feb. 23), pages 2268-2274.)

However, the conventional heparin-containing hydrogels discussed above are bulky, require high and thus expensive amounts of raw materials for their preparation and are difficult to include bio-functional peptides, which allow the development of biomaterials for tailored cell culture applications. Therefore, the conventional bulky hydrogels discussed above do not always mimic the extracellular matrix properly and have therefore drawbacks regarding their use in biomedical applications.

In contrast, combinatorial screening based on biomatrix layer represents a promising strategy to develop biomaterials for tailored cell culture applications. Libraries incorporating different biochemical cues have been investigated but few can simultaneously recapitulate relevant biochemical, physical and structural features of the extracellular matrix.

BRIEF DESCRIPTION OF THE INVENTION

To overcome the obstacles and disadvantages of conventional hydrogels, it is the object of the present invention to provide a biomatrix layer with adjustable 3D structure and morphology and with an adjustable surface for selective culture of specific cells types, coating of biomedical devices etc. The biomatrix layer shall be stable, easy and cheap to produce and the ingredients of the biomatrix layer shall enable combinatorial screening to develop biomaterials for tailored cell culture applications.

This object is solved by providing a biomatrix layer according to claim 1.

The biomatrix layer of the invention represents a non-covalent system based on liquid-liquid phase separation (coacervation) and glycosaminoglycan-peptide interaction and is capable to generate libraries of biomatrix films. Glycosaminoglycans, in particular sulfated glycosaminoglycans, are combined with bio-functional peptides, which are represented by $R_1$ in formula (I). The building blocks are combinatorically assembled and affect the biochemical composition, mechanical properties and morphology of the resulting 3D biomatrices.

Screening for tailored biomaterials can be performed using the biomatrix layer of the invention. Attachment of specific cell lines and/or cell types dependents on the type of the NCP, in particular of the GAG, and the concentration of the bio-functional peptide, with the cells retaining their potential for proliferation and differentiation. The invention thus provides a biomatrix layer, which mimics the extracellular matrix properly and is thus advantageous in regard to its use in biomedical applications.

Moreover, the invention provides a kit comprising the building blocks of the combinatorial library, wherein said kit enables the screening for tailored biomaterials.

Simple stepwise pipetting allowed the creation of sandwich structures for segregated co-culture of different cells. The non-covalent system is therefore an ideal tool for screening tissue specific extracellular matrix mimics for single and multiple layered cell culture models.

In one embodiment, a process for preparing the biomatrix layer of the invention is provided.

In a further embodiment, the invention provides methods for adjusting the 3D-structure and morphology, in particular the thickness, stiffness and porosity of the biomatrix layer.

BRIEF DESCRIPTION OF THE DRAWINGS

Specific embodiments of the present invention are described in the working examples with reference to the accompanying drawings.

DETAILED DESCRIPTION OF THE INVENTION

Figure 1:
FIG. 1 shows a scheme for different thin layer formation methods. Conventional hydrogel protocol: Components in high concentrations (mM) are mixed and the resulting mixture are pipetted in cell culture media or buffer solution to form a coherent hydrogel film. Biomatrix layer protocol: Components in low concentrations (µM) are mixed, resulting in liquid droplets in solution, which then sink to the bottom by gravity and form porous or coherent hydrogel film, dependent on the composition. Abbreviations used: PEG: Poly-(ethylenglycol), GAG: glycosaminoglycan.
Figure 1:
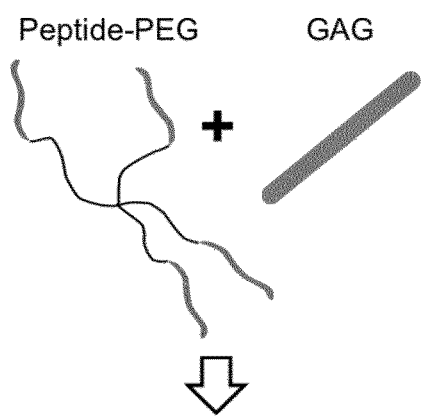
Figure 1:
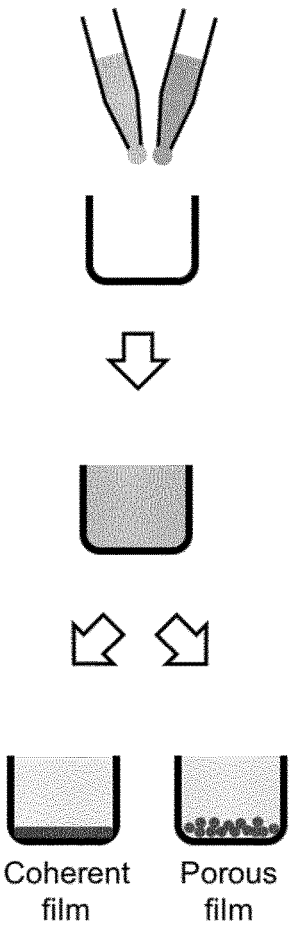
Figure 2:
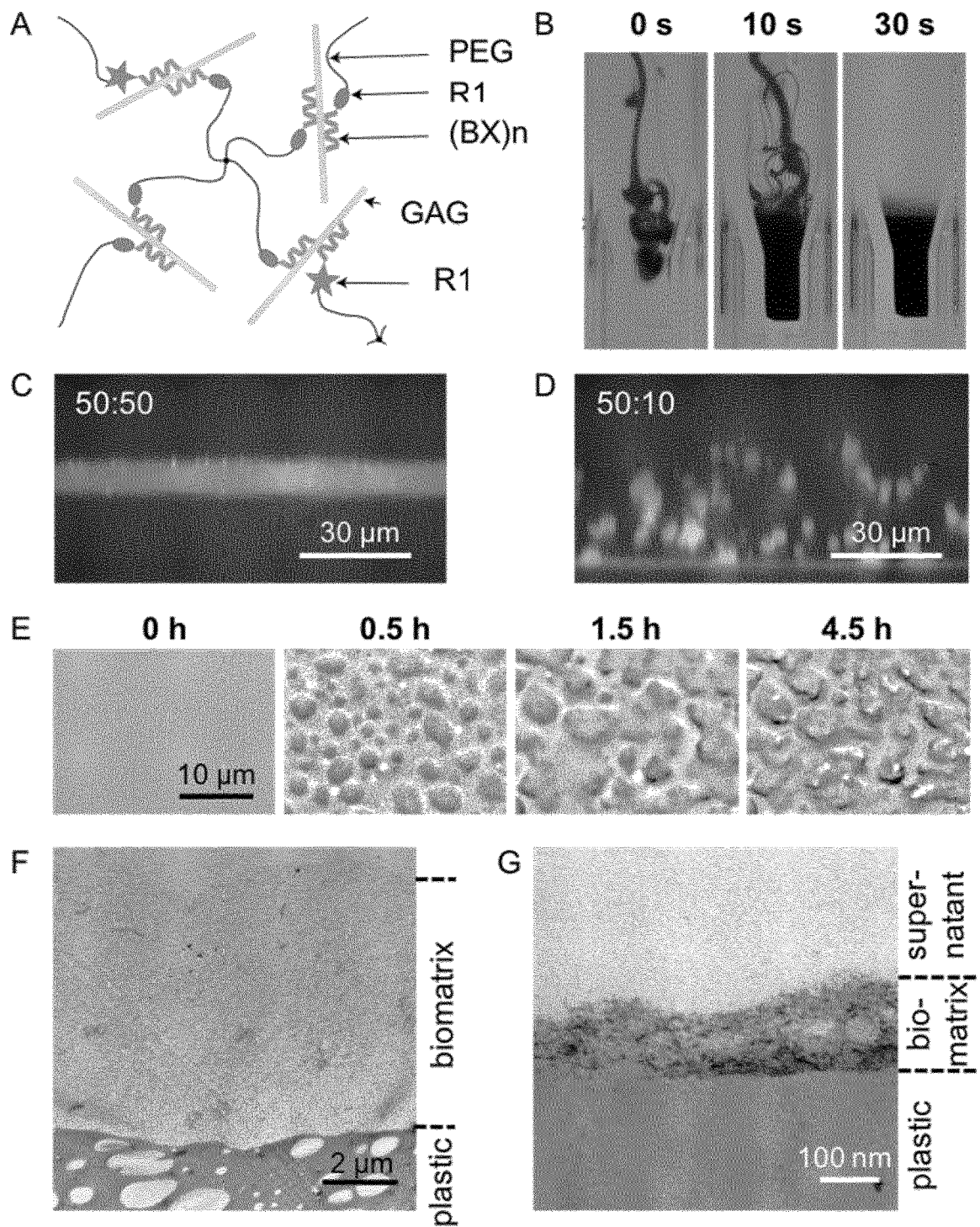
FIG. 2 shows biomatrix layer formation. A) Scheme of biomatrix composition. B) Conventional hydrogel protocol: phase separation occurs by pipetting a fresh mixture of 2.5 mM rhodamine labelled peptide-polyethylene glycol-conjugate comprising PEG and KA7 and 2.5 mM 14 kDa solution into PBS. C-D) Biomatrix layers protocol: thin layers were formed by mixing equal ratios of 50 µM rhodamine labelled peptide-polyethylene glycol-conjugate comprising PEG and KA7 solution and 50 µM (C) or 10 µM (D) of 14 kDa heparin. E) Time course of hydrogel thin layer formation by mixing equal ratios of 50 µM peptide-polyethylene glycol-conjugate comprising PEG, RGDSP and KA7 with 50 µM 14 kDa heparin (25 µM final concentration each) and incubated at 37° C. F) Transmission electron microscopy (TEM) image of a biomatrix layer prepared by mixing equal ratios of 50 µM peptide-polyethylene glycol-conjugate comprising PEG, RGDSP and KA7 with 50 µM 14 kDa heparin (25 µM final concentration each). G) TEM image of a biomatrix layer prepared by mixing equal ratios of 5 µM peptide-polyethylene glycol-conjugate comprising PEG, RGDSP and KA7 and 5 µM 14 kDa heparin (2.5 µM final concentration each).
Figure 3:
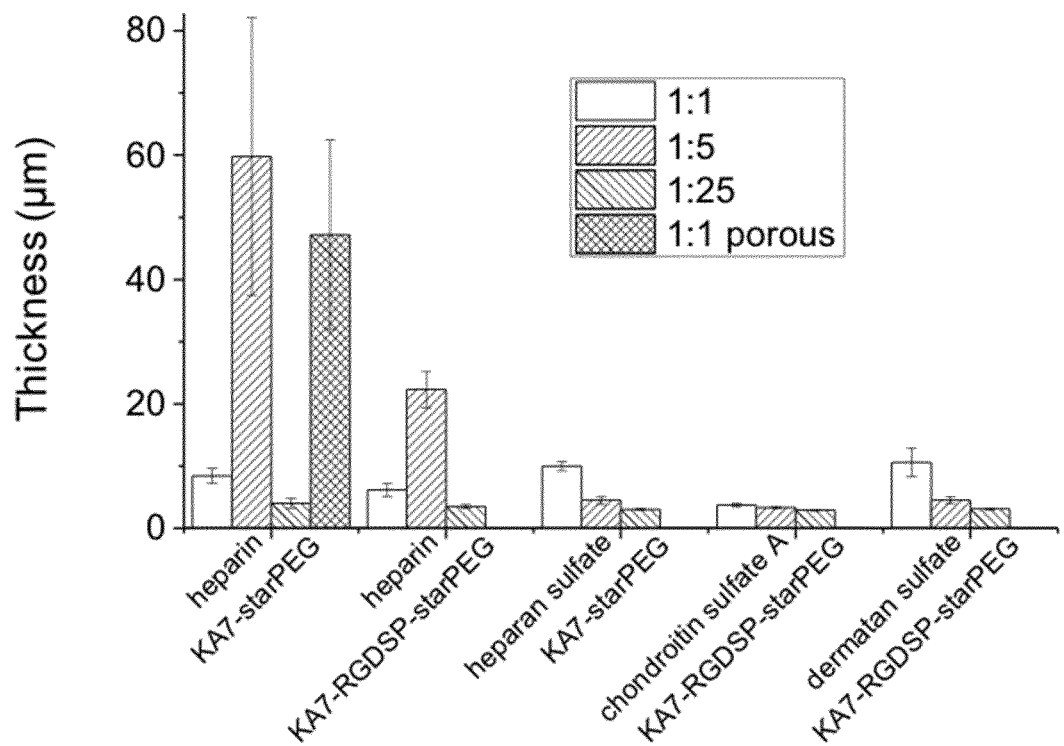
FIG. 3 shows analyses of biomatrix layer morphology and mechanical properties. A) Thickness of biomatrix layers depends on the composition. Layers were formed by mixing 50 µM peptide-polyethylene glycol-conjugate comprising PEG and KA7 or PEG, RGDSP and KA7 with 50 µM of different NCP in different molar ratios. For labelling 10% peptide-polyethylene glycol-conjugate comprising PEG-CWGG-KA7-Rho was used. For other NCPs the same weight per volume as 14 kDa heparin was used. B) Measurement of Young's modulus of biomatrix layers using AFM. Layers were formed with 1:1 ratio of PEG-peptide-conjugate to NCP. Matrigel was used as control and reference. Experiments were performed on two different days in triplicates each. Error bars show standard deviation (n=6).
Figure 3:
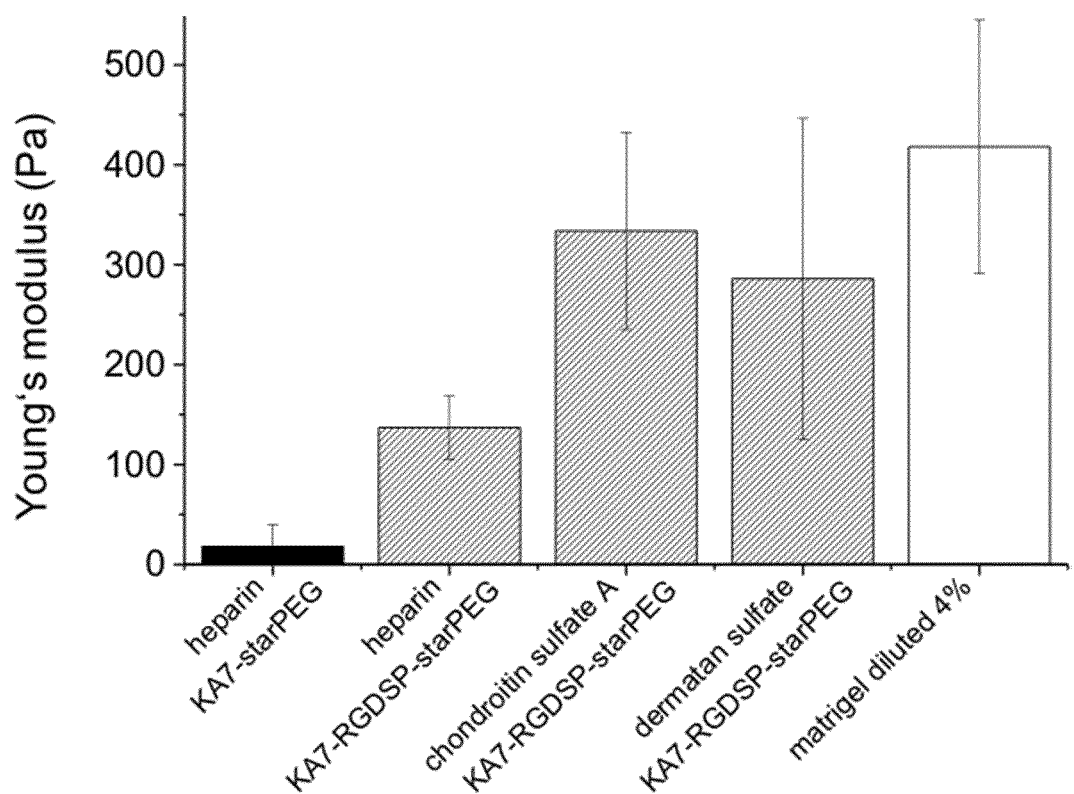
Figure 4:
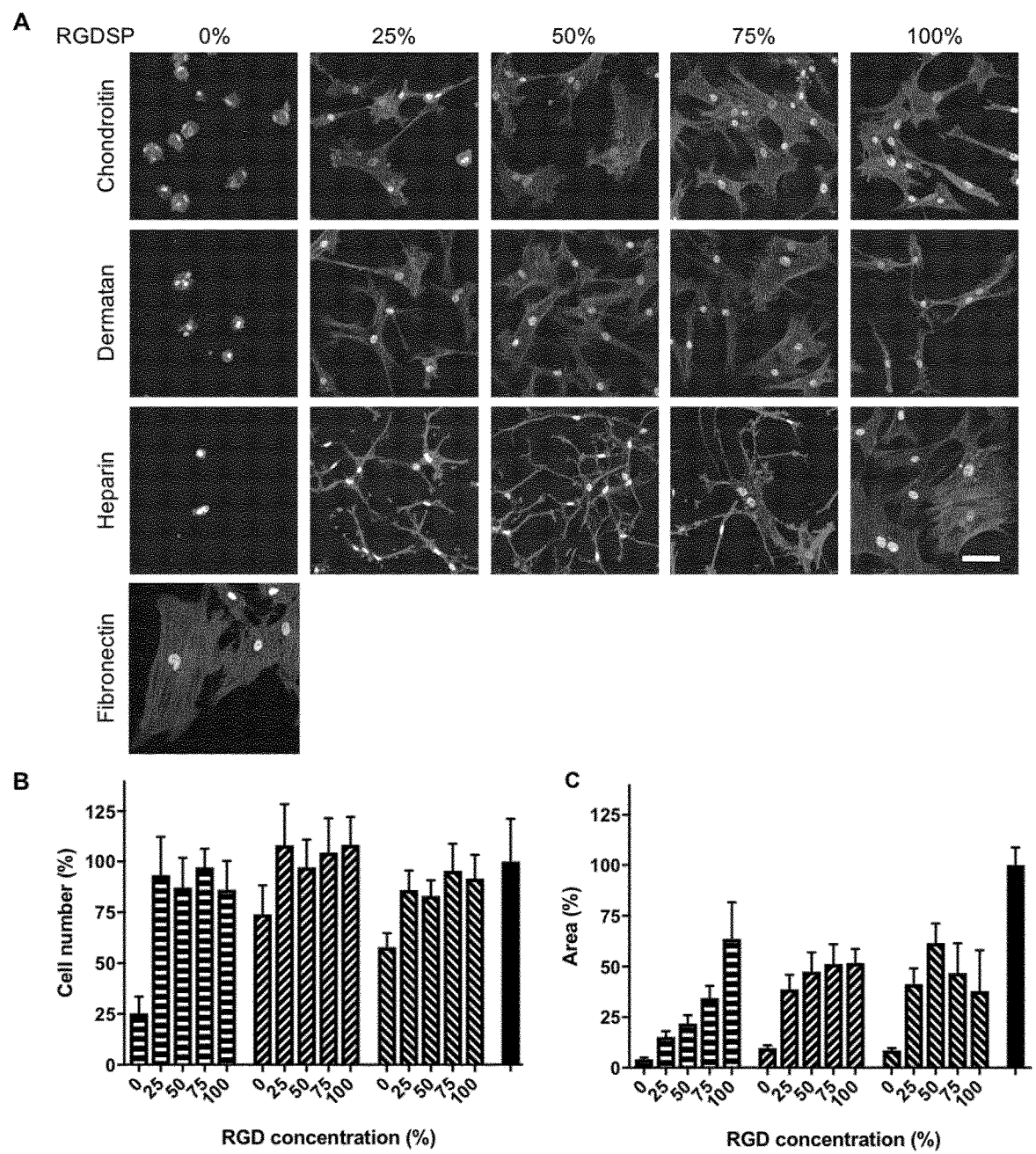
FIG. 4 shows results of the analysis of primary human mesenchymal stromal cells (MSC) attachment on biomatrix layers. Layers were by mixing equal ratio of 50 µM peptide-polyethylene glycol-conjugate comprising PEG and KA7 (with different percentages of peptide-polyethylene glycol-conjugate comprising PEG, RGDSP and KA7 with 50 µM 14 kDa heparin or same weight per volume for other NCPs. The control surface was coated with fibronectin. After overnight incubation cells were stained with phalloidin-CF633 (actin) and DAPI (nucleus) and fluorescent images acquired and quantified. A) Images of MSC cultured on different biomatrix layers and on fibronectin coatings (nuclei in white, actin in grey). B) Cell counts and C) cell area are analyzed for MSC cultured on different biomatrix layers compared to fibronectin coating. 1,250 MSC were seeded per well. The experiment was performed on two different days in triplicates each. Scale bar is 100 µm. Error bars show standard deviation (n=6).
Figure 5:
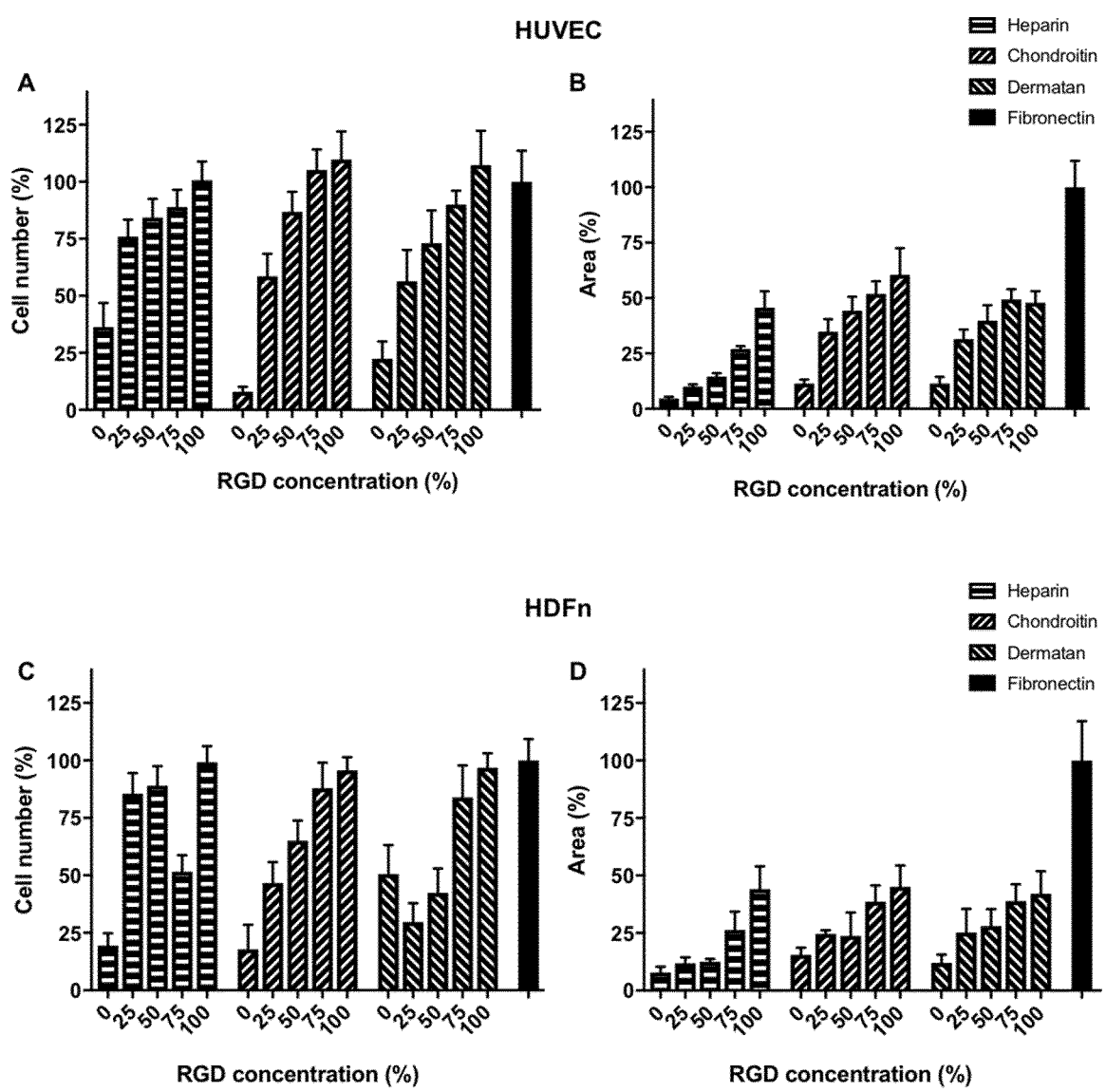
FIG. 5 shows results of the analysis of A-B) primary human umbilical veil endothelial cells (HUVEC) and C-D) neonatal human dermal fibroblasts (HDFn) attachment on biomatrix layers. Cell counts and covered area quantification on different biomatrix layer compositions compared to fibronectin coating are depicted. Layers were formed by mixing equal ratio of 50 µM peptide-polyethylene glycol-conjugate comprising PEG and KA7 (with different percentages of peptide-polyethylene glycol-conjugate comprising PEG, RGDSP and KA7 with 50 µM 14 kDa heparin or same weight per volume for other NCPs. The control surface was coated with 50 µg/ml fibronectin. After overnight incubation cells were stained with phalloidin-CF633 (actin) and DAPI (nucleus) and imaged using fluorescence spinning disc confocal microscopy and quantified. 2,500 HDFn or HUVEC were seeded per well. The experiment was performed on two different days in triplicates each. Scale bar is 100 µm. Error bars show standard deviation (n=6).
Figure 6:
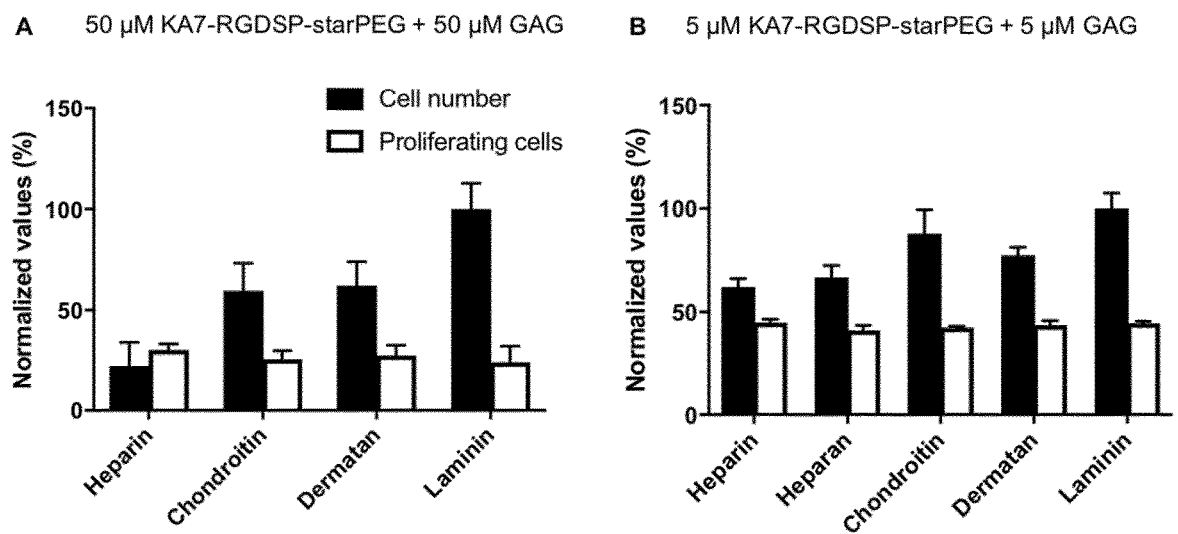
FIG. 6 shows results of the analysis of primary mouse neuronal progenitor cells (NPC) attachment and proliferation on biomatrix layers in comparison to laminin coatings. A) Layers were formed by mixing equal ratios of 50 µM peptide-polyethylene glycol-conjugate comprising PEG, RGDSP and KA7 with 50 µM of different GAG. 14 kDa heparin was used and equal weight for the other NCP. B) Layers were formed by mixing 5 µM peptide-polyethylene glycol-conjugate comprising PEG, RGDSP and KA7 with 5 µM of different NCPs. 14 kDa heparin was used and equal weight for the other NCP. A and B) 2,500 cells were seeded on films and incubated for 2 days before staining with EdU for proliferation and Hoechst33342 for cell number. All experiments were performed on two different days in triplicates each. Error bars show standard deviation (n=6).
Figure 7:
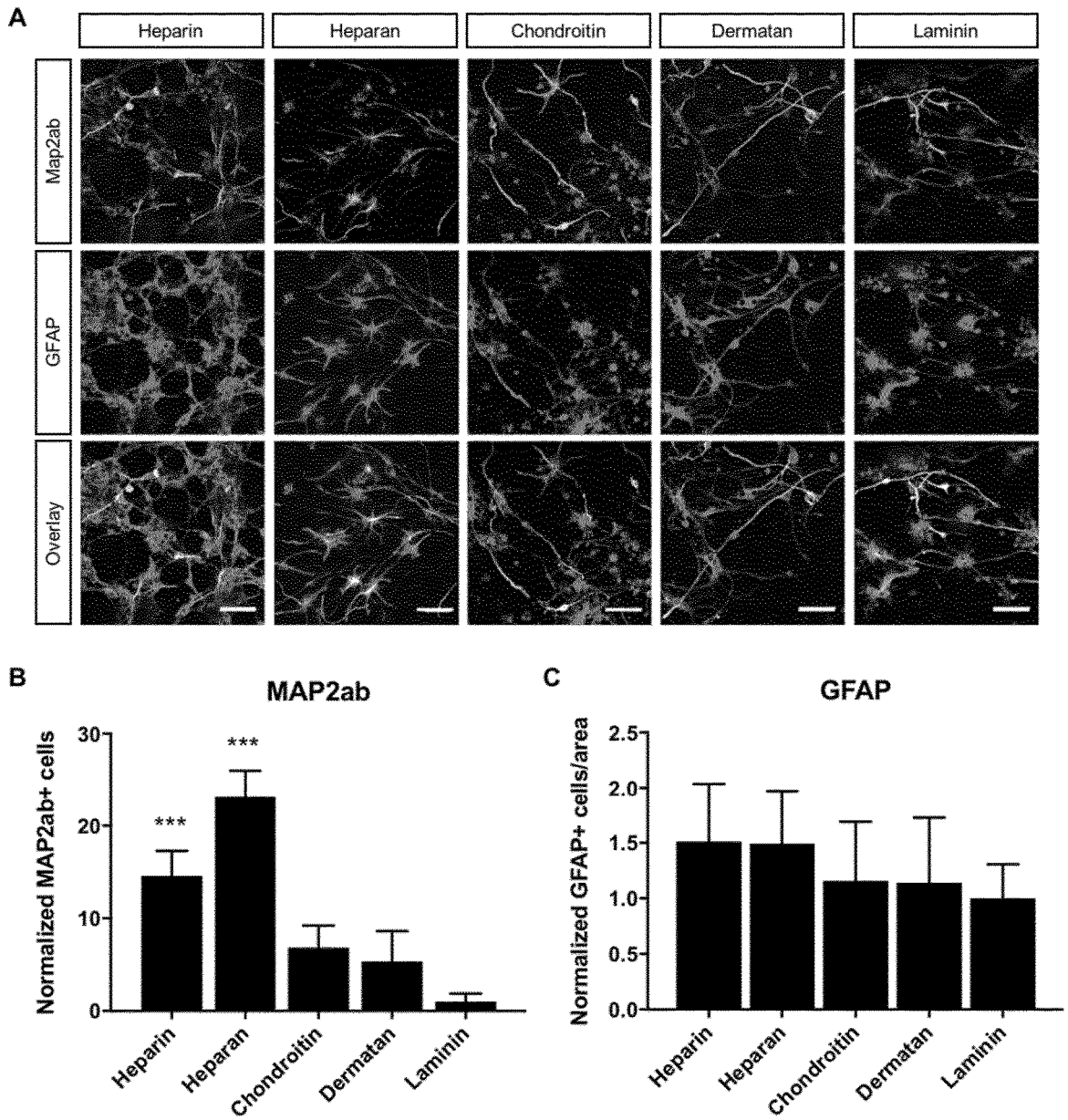
FIG. 7 shows results of the analysis of primary mouse neuronal progenitor cells (NPC) differentiation on biomatrix layers in comparison to laminin coatings. Layers were formed by mixing equal ratios of 5 µM peptide-polyethylene glycol-conjugate comprising PEG, RGDSP and KA7 with 5 µM of different NCPs. 14 kDa heparin was used and equal weight for the other NCP. A) Fluorescent images of neuronal (Map2ab) and astrocytic (GFAP) differentiated cells after 6 days of culture on biomatrix layers with different GAG and laminin. Nuclei were stained with Hoechst33342 blue. B) Analysis of rate of MAP2ab positive cells normalized to laminin. C) Analysis of the density of GFAP positive cells normalized to laminin. All experiments were performed on two different days in triplicates each. Error bars show standard deviation (n=6). Scale bars are 50 µm. Asterisks indicate statistical significance, ***: P≤0.01.
Figure 8:
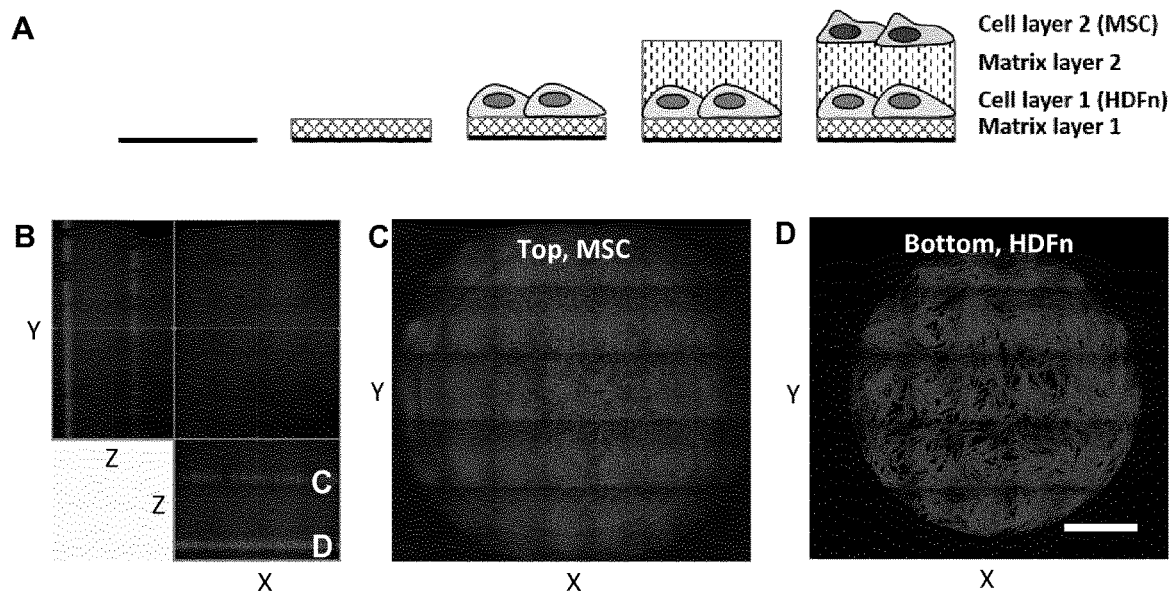
FIG. 8 shows results of the layer-by-layer co-culture of different cell types. Bottom layer was formed in PBS (pH 7.4) by mixing 5 µM peptide-polyethylene glycol-conjugate comprising PEG, RGDSP and KA7 with 0.7 mg/ml chondroitin sulfate A. After overnight incubation 5,000 HDFn were seeded and incubated overnight. As second biomatrix layer freshly mixed 2.5 mM peptide-polyethylene glycol-conjugate comprising PEG, RGDSP and KA7 and 3.5 mM 14 kDa heparin (5 µl overall) in HDFn cell culture medium were pipetted on top. 2,500 MSC were then seeded as top layer. Cells were stained with phalloidin-CF633 (actin) and imaged using fluorescence spinning disc confocal microscopy. A) Scheme of layer-by-layer co-culture formation. B) Z-stack and side views of the layer-by-layer assembly. C) Maximum projections of the MSC on the top layer. D) Maximum projection of the HDFn on the bottom layer. Scale bar is 1 mm.
Figure 9:
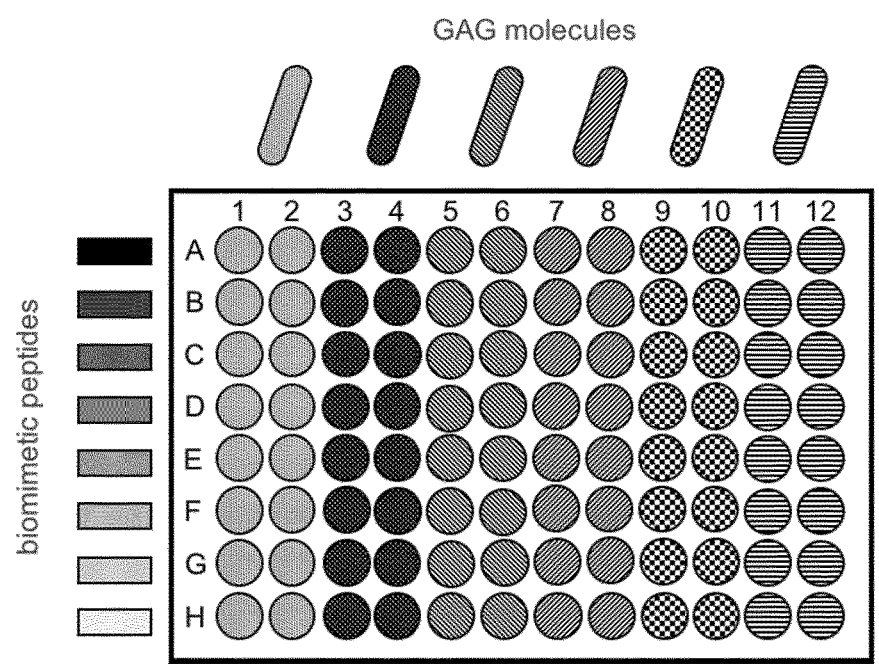
FIG. 9 shows an example of the assembly of the biomatrix kit by combining 6 different NCP with ingredients of the combinatorial peptide library. The kit can be used to screen for an ideal composition of the biomatrix layer of the invention.

The invention provides a biomatrix layer comprising, consisting essentially of or consisting of
a negatively charged polymer (NCP) at a concentration in the range of 0.1 μM to 1,000 μM; and
a peptide-polyethylene glycol-conjugate according to formula (I):

PEG-CW-spacer-$R_1$-spacer-(BX)$n$    (I);
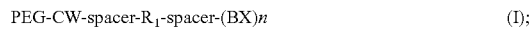

wherein
said spacer is absent or is a dipeptide, tripeptide or tetrapeptide, wherein said dipeptide, tripeptide or tetrapeptide consists of glycine, aminopropanoic acid, aminobutyric acid, aminopentanoic acid, aminohexanoic acid, aminoheptanoic acid, aminooctanoic acid and 3-aminoacrylic acid or combinations thereof, said spacer is preferably a dipeptide, most preferably the dipeptide GG;
CW is absent or is the dipeptide consisting of the amino acids cysteine and tryptophan;
B is lysine or arginine, X is selected from alanine, serine, threonine, tyrosine, or aspartic acid and n is an integer selected from 5, 6, 7, 8, 9, 10, 11, 12, 13, 14, 15, 16, 17, 18, 19 and 20;
$R_1$ represents a bio-functional peptide and may be absent or is a peptide comprising 5 to 30 amino acids;
PEG is comprised at a concentration in the range of 0.1 μM to 1,000 μM;
$R_1$, if present, is comprised at a concentration in the range of 0.1 μM to 4,000 μM; and
(BX)n is comprised at a concentration in the range of 0.4 μM to 4,000 μM.

The invention provides in one embodiment a biomatrix layer comprising, consisting essentially of or consisting of
a negatively charged polymer (NCP) at a concentration in the range of 0.1 μM to 1,000 μM; and
a peptide-polyethylene glycol-conjugate according to formula (Ia):

PEG-$R_1$-(BX)$n$    (Ia)

wherein
B is lysine or arginine, X is selected from alanine, serine, threonine, tyrosine, or aspartic acid and n is an integer selected from 5, 6, 7, 8, 9, 10, 11, 12, 13, 14, 15, 16, 17, 18, 19 and 20;
$R_1$ represents a bio-functional peptide and may be absent or is a peptide comprising 5 to 30 amino acids;
PEG is comprised at a concentration in the range of 0.1 μM to 1,000 μM;
$R_1$, if present, is comprised at a concentration in the range of 0.1 μM to 4,000 μM; and
(BX)n is comprised at a concentration in the range of 0.4 μM to 4,000 μM.

In one embodiment, the invention provides a biomatrix layer comprising, consisting essentially of or consisting of
a negatively charged polymer (NCP) at a concentration in the range of 0.1 μM to 250 μM; and
a peptide-polyethylene glycol-conjugate according to formula (Ia):

PEG-$R_1$-(BX)$n$    (Ia)

wherein
B is lysine or arginine, X is selected from alanine, serine, threonine, tyrosine, or aspartic acid and n is an integer selected from 5, 6, 7, 8, 9, 10, 11, 12, 13, 14, 15, 16, 17, 18, 19 and 20;
$R_1$ represents a bio-functional peptide and may be absent or is a peptide comprising 5 to 30 amino acids;
PEG is comprised at a concentration in the range of 0.1 µM to 250 µM;
$R_1$, if present, is comprised at a concentration in the range of 0.1 µM to 1,000 µM; and
(BX)n is comprised at a concentration in the range of 0.4 µM to 1,000 µM.

Accordingly, in a further preferred embodiment, the invention provides a biomatrix layer comprising, consisting essentially of or consisting of
a negatively charged polymer (NCP) at a concentration in the range of 900 µM to 1,000 µM; and
a peptide-polyethylene glycol-conjugate according to formula (Ia):

PEG-$R_1$-(BX)$n$            (Ia)

wherein
B is lysine or arginine, X is selected from alanine, serine, threonine, tyrosine, or aspartic acid and n is an integer selected from 5, 6, 7, 8, 9, 10, 11, 12, 13, 14, 15, 16, 17, 18, 19 and 20;
$R_1$ represents a bio-functional peptide and may be absent or is a peptide comprising 5 to 30 amino acids;
PEG is comprised at a concentration in the range of 900 µM to 1,000 µM;
$R_1$, if present, is comprised at a concentration in the range of 3,500 µM to 4,000 µM; and
(BX)n is comprised at a concentration in the range of 3,500 µM to 4,000 µM.

These concentrations of the components in the biomatrix layer are reached, when e.g. individual stock solutions comprising the components in a range from 2.5 µM to 7.5 µM, preferably 5 µM, in PBS buffer are used to prepare the biomatrix layer of the invention, Coacervation occurs as generally described for all embodiments herein and a biomatrix layer of the invention is formed, in which the components are concentrated in the ranges as described above compared the PBS buffer supernatant.

The inventors have surprisingly found that liquid-liquid phase separation (coacervation) was observed when pipetting the still fluidic peptide-polyethylene glycol-conjugate and NCP building blocks into buffer or cell culture media. Moreover, by mixing the two biomatrix components at 50 µM or lower concentrations (concentration in stem solutions of NCP and peptide-polyethylene glycol-conjugate before mixing), much lower than those used to form a conventional bulky hydrogel, the liquid-liquid phase separation led to the formation of coacervate droplets. The droplets underwent non-covalent gelation and formed a thin film on the bottom of the well plate.

To form the biomatrix layer according to the invention, a polymeric network is required which forms the structural backbone of the biomatrix layer.

Generally, the polymeric network may be any polymeric network. Preferably the polymeric network is capable of self-assembly. A polymeric network that is capable of self-assembly is easy to produce, guarantees the homogeneous distribution of the biomatrix building blocks and does not require additional steps for forming the thin layer polymer.

In a preferred embodiment, the polymeric network is a biomatrix. In some embodiments, the biomatrix may comprise two or more polymer constituents in order to take advantage of the properties that each of the polymer constituents impart to the resultant biomatrix.

Non-limiting examples of polymers suitable for forming a biomatrix to provide the polymeric network include polyvinyl alcohol (PVA), polyethylene glycol, poly(acrylic acid) and its derivatives; poly(ethyleneoxide) and its copolymers, polyphosphazene, silicones, polyacrylamides, polyvinylpyrrolidones, poly-hydroxyethylmethacrylate, polyurethanes and its derivatives; or combinations thereof.

In a more preferred embodiment, the polymer suitable for forming the biomatrix layer of the invention is polyethylene glycol (PEG).

PEG is an oligomer or polymer composed of ethylene oxide monomers. Because different applications require different polymer chain lengths, PEGs are prepared by polymerization of ethylene oxide and are commercially available over a wide range of molecular weights from 300 g/mol to 10,000,000 g/mol. While PEGs with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete.

PEGs are also available with different geometries:
Linear PEGs, where the ethylene oxide monomers are bound to each other in an unbranched polymer chain;
Branched PEGs, which have three to ten PEG chains emanating from a central core group;
Star PEGs, which have 10 to 100 PEG chains emanating from a central core group; and
Comb PEGs, which have multiple PEG chains normally grafted onto a polymer backbone.

The numbers that are often included in the names of PEGs indicate their average molecular weights (e.g. a PEG with n=9 would have an average molecular weight of approximately 400 daltons, and would be labeled PEG 400). Most PEGs include molecules with a distribution of molecular weights (i.e. they are polydisperse). The size distribution can be characterized statistically by its weight average molecular weight (Mw) and its number average molecular weight (Mn), the ratio of which is called the polydispersity index (Mw/Mn). MW and Mn can be measured by mass spectrometry.

PEG is soluble in water, methanol, ethanol, acetonitrile, benzene, and dichloromethane, and is insoluble in diethyl ether and hexane.

In another embodiment, the biomatrix layer of the invention comprises a linear PEG. Using linear PEGs has the advantage that linear PEGs are cheap and possess a narrower molecular weight distribution. Moreover, it may be easier to separate a linear PEG chain with two peptides bound to it from that with only one peptide, as compared to purify the 4-arm starPEG comprising 4 peptides from a mixture of star PEGs of lower degree of modification.

However, more suitable for preparing the biomatrix layer of the invention is using a starPEG. Suitably, said starPEG has a molecular weight in the range of 4 kD to 40 kD, preferably in the range of 4 kD to 30 kD, more preferably in the range of 4 kD to 20 kD, most preferably in the range of 5 kD to 15 kD. Further most preferably, said starPEG is a 4-arm starPEG, which has most suitably a molecular weight of 10 kD.

In a further embodiment of the invention, the PEG comprised in biomatrix layer of the invention may be a mixture of a starPEG and a liner PEG.

When linear PEG is comprised in the biomatrix layer of to the invention, it has suitably a molecular weight in the range of 1 kD to 100 kD, preferably in the range 2 kD to 80 kD, 3 kD to 60 kD, 4 kD to 40 kD, most preferably in the range of 5 kD to 20 kD. Even most preferably, the linear PEG comprised in the biomatrix layer according to the invention has a molecular weight selected from 5 kD, 10 kD, 15 kD and 20 kD.

The ratio of starPEG:liner PEG in said mixture may for example be 1:1, but can be adjusted to any ratio in accordance with the desired characteristics of the biomatrix layer to be produced.

In a further preferred embodiment, the PEG, which is used to prepare the biomatrix layer of the invention, is functionalized. By "functionalize" is meant to modify a molecule in a manner that results in the attachment of a functional group or moiety. For example, a molecule may be functionalized by the introduction of a molecule, which makes the molecule a strong nucleophile or a conjugated unsaturation. Preferably a molecule, for example PEG, is functionalized to become a thiol, amine, acrylate, azide, alkyne, or quinone. More preferably, for use in the preparation of the biomatrix layer of the invention, the PEG is maleimide-functionalized, carboxylic acid-functionalized, amino-functionalized, azide-functionalized, or alkyne-functionalized. This type of functionalization is required to conjugate PEG to the oligopeptide of formula (I). Thus, in a most preferred embodiment, the starPEG, in particular the 4-arm PEG, and/or the linear PEG is functionalized with a maleimide, carboxylic acid or amino group.

It has been shown that the use of polymer-peptide-conjugates leads to the formation of hydrogels that exhibit self-organizing properties (WO 2014040591 A2). Accordingly, in a preferred embodiment, the biomatrix layer of the invention comprises a conjugate of oligopeptides and polyethylene glycol (PEG), e.g. conjugates of 4-arm starPEG and oligopeptides or linear PEG and oligopeptides.

In a preferred embodiment, the biomatrix layer of the invention comprises a conjugate of peptide-polyethylene glycol-conjugate of formula (I) as described above.

The PEG-oligopeptide conjugate suitably comprises one, two or more of the oligopeptides which are coupled to a linear or 4-arm starPEG.

n is preferably an integer selected from 5, 6, 7, 8, 9, 10 and 11.

More preferably, n is an integer selected from 5, 6, 7, 8 and 9.

Most preferably, n is 5 and 7.

In a preferred embodiment, B is lysine.

In a further preferred embodiment, B is arginine.

In a preferred embodiment, X is alanine or serine.

In a most preferred embodiment, X is alanine.

In a further most preferred embodiment, X is serine.

In the peptides of the present invention, each amino acid residue is represented by a one-letter or a three-letter designation, corresponding to the trivial name of the amino acid, in accordance with the following conventional list:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Norleucine | L* | Nor |

(BX)n is preferably selected from KA11, KA9, KA7, KA6, KA5, KS7, KS6, KS5, RA7, RA6, RA5, RS7, RS6, and RS5. Most preferably, (BX)n is selected from: KA7, KA6, KA5, KS7, KS6 and KS5. The respective peptide sequences are shown in table 1 below:

TABLE 1

Preferred peptide sequences of the (BX)n

| (BX)n Peptide | Sequence | SEQ ID NO. |
|---|---|---|
| KA5 | KAKAKAKAKA | 1 |
| KA6 | KAKAKAKAKAKA | 2 |
| KA7 | KAKAKAKAKAKAKA | 3 |
| KA9 | KAKAKAKAKAKAKAKA | 4 |
| KA11 | KAKAKAKAKAKAKAKAKAKA | 5 |
| KS5 | KSKSKSKSKS | 6 |
| KS6 | KSKSKSKSKSKS | 7 |
| KS7 | KSKSKSKSKSKSKS | 8 |
| RA5 | RARARARARA | 9 |
| RA6 | RARARARARARA | 10 |
| RA7 | RARARARARARARA | 11 |
| RS5 | RSRSRSRSRS | 12 |
| RS6 | RSRSRSRSRSRS | 13 |
| RS7 | RSRSRSRSRSRSRS | 14 |

The peptide-polyethylene glycol-conjugate of the invention comprises in a further embodiment of the invention a bio-functional peptide $R_1$. The bio-functional peptide has various functions: In a preferred aspect, the bio-functional peptide is used to improve the adhesion of cells to the biomatrix layer of the invention resulting in the provision of a biopolymer. In still a further aspect of the invention, the bio-functional peptide can be used to facilitate the proteolysis of such a biopolymer by cells or proteases in vivo. It further recapitulates signaling function of soluble signaling proteins e.g. growth factors, etc.

In a preferred embodiment of the invention, $R_1$ contains 5 to 30 amino acids.

In a more preferred embodiment of the invention, $R_1$ contains 5 to 15 amino acids.

One special feature of the biomatrix layer of the invention is that a variety of bioactive peptides can be incorporated into the resulting biomaterial structure. For example, the bio-functional peptide can be designed to be a substrate for an enzyme used by cells migration through tissues and remodel tissues (e.g., as a substrate for plasmin, elastase or matrix metalloproteinases (MMPs), such as collagenase). The degradation characteristics of the biomatrix layer can be manipulated by changing the sequence of the bio-functional peptide. One may make a biomatrix layer gel that is degradable by collagenase, but not plasmin, or by plasmin, but not collagenase. Furthermore, it is possible to make the biomatrix layer gel degrade faster or slower in response to such an enzyme, simply by changing the amino acid sequence so as to alter the Km or kcat, or both, of the enzymatic reaction. One can thus make a biomaterial that is biomimetic, in that it is capable of being remodeled by the normal remodeling characteristics of cells.

Adhesion Sites

However, most preferred according to the invention is the incorporation of bio-functional peptides, represented by $R_1$, for cell adhesion, namely peptides that bind to adhesion-promoting receptors on the surfaces of cells into or onto the biomatrix layer of the present invention. It is straightforward to incorporate a variety of such adhesion-promoting peptides, such as the RGD (SEQ ID NO: 15) sequence from fibronectin or the RGDS (SEQ ID NO: 16) sequence. The RGD peptide (SEQ ID NO: 15) is the binding motif of fibronectin to cell surface receptor integrin. The RGDS sequence (SEQ ID NO: 16) was found initially to promote the attachment of rat kidney fibroblasts to fibronectin. Free RGDS peptide (SEQ ID NO: 16) inhibits attachment of cells to fibronectin-coated substrates. The RGDS sequence (SEQ ID NO: 16) is also a target for infectious agents (Treponema's syphilis, Mycobacterium's tuberculosis). RGDS (SEQ ID NO: 16) can also block fibrinogen-induced aggregation of intact erythrocytes and specific binding of fibrinogen to erythrocyte membranes.

In a further preferred embodiment, the sequence of the bio-functional peptide $R_1$ is selected from the group consisting of the sequences of SEQ ID NOs: 15 to 353 as disclosed in the sequence listing attached hereto. These sequences comprise oligopeptide sequences which mimic the ECM and signal peptides.

More preferably, the sequence of the bio-functional peptide $R_1$ is selected from the group consisting of the sequences of SEQ ID NOs: 15, 16, 17, 22, 26, 27, 30, 31, 32, 41, 43, 44, 45, 46, 49, 51, 54, 57, 64, 66, 67, 68, 78, 80, 84, 85, 90, 93, 99, 108, 120, 124, 131, 144, 145, 154, 156, 160, 171, 172, 175, 177, 180, 183, 185, 187, 188, 189, 190, 192, 200, 201, 211, 219, 222, 224, 230, 233, 236, 237, 238, 239, 241, 243, 246, 257, 259, 260, 262, 263, 264, 265, 277, 278, 279, 283, 299, 302, 315, 320, 321, 323, 333, 342, 345 and 348 as disclosed in the sequence listing attached hereto. These sequences comprise adhesion and growth factor mimetics.

Most preferably, the sequence of the bio-functional peptide $R_1$ is selected from the group consisting of the sequences of SEQ ID NOs: 17, 30, 32, 46, 49, 57, 63, 67, 77, 93, 130, 145, 155, 159, 187, 218, 233, 237, 240, 242, 245, 259, 264, 276, 282, 319, 320, 341, 345 and 347 as disclosed in the sequence listing attached hereto. These sequences comprise core sequences of adhesion peptides and sequences of signal peptides that are of special interest for use in the biomatrix layer of the invention.

In a particularly preferred embodiment of the invention, $R_1$ is RGDSP (SEQ ID NO: 17).

In one embodiment of the of the invention, the bio-functional peptide $R_1$ may also be absent, leading to peptide-polyethylene glycol-conjugate of formula (Ib):

$$\text{PEG-(BX)}n \qquad (Ib)$$

wherein B, X and n are as defined for formula (I).

Very good results in regard to the production of the biomatrix layer of the invention were achieved, when the peptide-polyethylene glycol-conjugate was a mixture of a peptide-polyethylene glycol-conjugate of formula (Ia) and a peptide-polyethylene glycol-conjugate of formula (Ib). Thus, in a most preferred embodiment, the invention provides a biomatrix layer comprising a mixture of a peptide-polyethylene glycol-conjugate of formula (Ia) and a peptide-polyethylene glycol-conjugate of formula (Ib). In this mixture, up to three different conjugates according to formula (Ia), which contain different bio-functional peptides at position $R_1$, can be contained.

The proportion of said peptide-polyethylene glycol-conjugate of formula (Ia) in said mixture is tunable and tuning of the proportion of said peptide-polyethylene glycol-conjugate of formula (Ia) in said mixture can be used to control the cell load, i.e. surface coverage of the biomatrix layer with cells. Suitably the proportion of the peptide-polyethylene glycol-conjugate of formula (Ia) in said mixture is in the range from 0 to 100 mol %, suitably in the range of 0.1 to 99.9 mol %. A proportion of said peptide-polyethylene glycol-conjugate of formula (Ia) of 0 mol % means that the peptide-polyethylene glycol-conjugate of formula (Ia) is absent and only a peptide-polyethylene glycol-conjugate of formula (Ib) is present. A proportion of said peptide-polyethylene glycol-conjugate of formula (Ia) of 100 mol % means that only the peptide-polyethylene glycol-conjugate of formula (Ia) is present and that the peptide-polyethylene glycol-conjugate of formula (Ib) is absent. In a preferred embodiment, the proportion of the peptide-polyethylene glycol-conjugate of formula (Ia) in said mixture is in the range from 1 to 99 mol % or 10 to 95 mol %, more preferably 10 to 90 mol %, 20 to 70 mol % or 25 to 55 mol %.

In a more preferred embodiment, the proportion of the peptide-polyethylene glycol-conjugate of formula (Ia) in said mixture is 25 mol %. For example, for MSCs, when heparin was used as NCP, 25 mol % of a peptide-polyethylene glycol-conjugate of formula (Ia) led to a remarkable increase in cell number on the biomatrix film. Best adhesion and spreading to heparin hydrogels was achieved with 100 mol % starPEG-RGDSP. The surface coverage increased gradually with increasing proportion of the peptide-polyethylene glycol-conjugate of formula (Ia). Surprisingly, one of the highest surface coverage with MSCs was achieved on a biomatrix layer comprising a chondroitin sulfate as NCP and a proportion of 50 mol % of a the peptide-polyethylene glycol-conjugate of formula (Ia) was used (see working examples). Accordingly, in further a most preferred embodiment, the proportion of the peptide-polyethylene glycol-conjugate of formula (Ia) in the mixture with a peptide-polyethylene glycol-conjugate of formula (Ib) is 50 mol %.

Suitably, the bio-functional peptide $R_1$ is linked to the PEG and (BX)n building blocks by short peptide sequences. Accordingly, the peptide-polyethylene glycol-conjugate of formula (I) is preferably a peptide-polyethylene glycol-conjugate of formula (II):

$$\text{PEG-CWGG-}R_1\text{-GG-(BX)}n \qquad (II)$$

wherein B, X, n and $R_1$ are as defined for formula (I).

Also in the peptide-polyethylene glycol-conjugate of formula (II), $R_1$ can be absent. Accordingly, the peptide-polyethylene glycol-conjugate of formula (I) is preferably a peptide-polyethylene glycol-conjugate of formula (IIa):

PEG-CWGG-(BX)n      (IIa)

wherein B, X, n and $R_1$ are as defined for formula (I).

As described for the peptide-polyethylene glycol-conjugates of formulae (I), (Ia) and (Ib), in a most preferred embodiment, the invention provides a biomatrix layer comprising a mixture of a peptide-polyethylene glycol-conjugate of formula (II) and a peptide-polyethylene glycol-conjugate of formula (IIa). In this mixture, up to three different conjugates according to formula (II), which contain different bio-functional peptides at position $R_1$, can be contained.

Suitably the proportion of the peptide-polyethylene glycol-conjugate of formula (II) in said mixture is in the range from 0 to 100 mol %, suitably 0.1 to 99.9 mol %. A proportion of said peptide-polyethylene glycol-conjugate of formula (II) of 0 mol % means that the peptide-polyethylene glycol-conjugate of formula (II) is absent and only a peptide-polyethylene glycol-conjugate of formula (IIa) is present. A proportion of said peptide-polyethylene glycol-conjugate of formula (II) of 100 mol % means that only the peptide-polyethylene glycol-conjugate of formula (II) is present and the peptide-polyethylene glycol-conjugate of formula (IIa) is absent. In a preferred embodiment, the proportion of the peptide-polyethylene glycol-conjugate of formula (II) in said mixture is in the range from 1 to 99 mol % or 10 to 95 mol %, more preferably, 10 to 90 mol %, 20 to 70 mol % or 25 to 55 mol %. Most preferably, the proportion of the peptide-polyethylene glycol-conjugate of formula (II) in said mixture is 25 mol %. Even most preferably, the proportion of the peptide-polyethylene glycol-conjugate of formula (II) in the mixture with a peptide-polyethylene glycol-conjugate of formula (Ib) is 50 mol %.

The production of the peptide-polyethylene glycol-conjugates of formulae (I), (Ia), (II) and (IIa) can be done, for example, simply by mixing the respective peptide with the maleimide-functionalized, carboxylic acid-functionalized, or amino-functionalized PEG under conditions which permit the conjugate formation. For example, the thiol group of a cysteine residue of the linker peptide can be used to link the peptides to maleimide-functionalized PEG by Michael-type addition reaction. Alternatively, to modify the amino-functionalized PEG with azide, the resulting polymer will allow the conjugation of alkyne-containing peptide through click chemistry.

In a particularly preferred embodiment of the invention, the biomatrix layer comprises a peptide-polyethylene glycol-conjugate selected from starPEG-RGDSP-KA7 and 10 kD starPEG-KA7 or a mixture thereof as defined above, wherein the starPEG is a 4-arm starPEG with a molecular weight of 10 kD; or a peptide-polyethylene glycol-conjugate selected from starPEG-CWGG-RGDSP-GG-KA7 and 10 kD starPEG-CWGG-KA7 or a mixture thereof as defined above, wherein the starPEG is a 4-arm starPEG with a molecular weight of 10 kD Corresponding to a specifically preferred embodiment of the present invention, the biomatrix layer comprises in addition a negatively charged polymer (NCP), which can be naturally occurring NCP or a synthetic NCP. According to this embodiment, an oligosaccharide/oligopeptide/PEG-system exists where the oligopeptide (which is represented by $R_1$-(BX)n, such as CWGG-R1-GG-(BX)n and CWGG-(BX)n) is chemically conjugated to the PEG and the gel formation is carried out through mixing the oligopeptide-PEG-conjugate and the NCP. The non-covalent macromolecular self-organization is also induced by the interaction of the oligopeptide-PEG-conjugate and the NCP. The choice of the PEG and the NCP can lead to various gel properties including the flow behavior, the gelling condition, the gelling speed, the thickness, the stiffness, the porosity as well as adjustable affinity of peptides interacting with bioactive proteins, for example, cells and growth factors and the like. However, variability in gel properties is also realized through changes of a the peptide sequence motif $R_1$-(BX)n, wherein according to the concept of the present invention the corresponding biomatrix layer is principally also possible without $R_1$. In this manner, the flexible design of the oligopeptide sequence can lead to a broad variety of gel properties, that not only lead to the above-stated rheological properties, the gelling condition, the gelling speed, the thickness, the stiffness, the porosity and protein binding properties, but also leads to properties such as for example, the biological degradation due to proteolytic hydrolysis or other enzymatic activity or non-enzymatic activity, such as light impact sensitivity.

The NCP comprised in the biomatrix layer of the invention is typically selected from the group consisting of glycosaminoglycans (GAGs), sulphated or phosphated linear polymers, and sulphated or phosphated cyclic polymers. Preferred are negatively charged oligosaccharides. According to an advantageous embodiment, said negatively charged oligosaccharide is a sulfated or phosphorylated oligosaccharide, preferably selected from a group of oligosaccharides which comprises heparin, dextran sulfate, α-cyclodextrin sulfate, β-cyclodextrin sulfate, γ-cyclodextrin sulfate, α-cyclodextrin phosphate, β-cyclodextrin phosphate, γ-cyclodextrin phosphate, heparan sulfate, chondroitin sulfate, dermatan sulfate and keratan sulfate. According to another advantageous embodiment, said NCP is selected from polystyrene sulfate (PSS), sulfated alginate, sulfated hyaluronic acid, cyclic dextran sulfate, cyclic dextran phosphate and phytic acid.

In a preferred embodiment, the NCP is selected from the group consisting of polystyrene sulfate (PSS), sulfated alginate, sulfated hyaluronic acid, cyclic dextran sulfate, cyclic dextran phosphate and phytic acid.

More preferably, the biomatrix layer of the invention further comprises a NCP, which is a sulfated glycosaminoglycan (GAG). GAGs are long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) or galactose. GAGs are highly polar and attract water.

GAGs have high degrees of heterogeneity with regards to molecular mass, disaccharide construction, and sulfation. Based on core disaccharide structures, GAGs are classified into four groups: heparin/heparan sulfate and chondroitin sulfate/dermatan sulfate, keratan sulfate and hyaluronic acid.

In a preferred embodiment, the biomatrix layer of the invention comprises a NCP selected from the group comprising, consisting essentially or consisting of heparin, heparan sulfate, chondroitin sulfate, dermatan sulfate, keratan sulfate, dextran sulfate and hyaluronic acid.

In an especially preferred embodiment, the biomatrix layer of the invention comprises a NCP selected from the group comprising, consisting essentially or consisting of heparin, heparan sulfate, chondroitin sulfate, dermatan sulfate, keratan sulfate, dextran sulfate and hyaluronic acid.

In a preferred embodiment of the invention, the NCP is heparin. Heparin originates from the mucosa of pig intestine or bovine lung tissue. Heparin is preferably of pharmaceutical quality.

In a further preferred embodiment, the NCP is heparan sulfate.

In a further preferred embodiment, the NCP is chondroitin sulfate.

In a further preferred embodiment, the NCP is dermatan sulfate.

In a further preferred embodiment, the NCP is keratan sulfate.

In a further preferred embodiment, the NCP is dextran sulfate.

In further preferred embodiment, the NCP is hyaluronic acid or sulfated hyaluronic acid.

In further preferred embodiment, the NCP is sulfated alginate.

In further preferred embodiment, the NCP is cyclic dextran sulfate.

In further preferred embodiment, the NCP is cyclic dextran phosphate.

In further preferred embodiment, the NCP is phytic acid.

The heparin, heparan sulfate, chondroitin sulfate, dermatan sulfate, keratan sulfate, dextran sulfate, polystyrene sulfate (PSS), sulfated alginate, sulfated hyaluronic acid, cyclic dextran sulfate, cyclic dextran phosphate or phytic acid has suitably a molecular weight in the range of 4 kD to 600 kD. Preferred is the use of heparin, heparan sulfate, chondroitin sulfate, dermatan sulfate, keratan sulfate, dextran sulfate or hyaluronic acid in pharmaceutical quality.

The biomatrix layer of the invention differs from conventional hydrogels structurally and is formed by using stock solutions comprising low concentrations of the building blocks in the range from 0.1 µM to 1,000 µM.

Accordingly, PEG is comprised in a stock solution at a concentration in the range from 0.1 µM to 250 µM, preferably in the range from 0.1 µM to 125 µM or 0.1 µM to 75 µM, more preferably 0.1 µM to 75 µM or 0.1 µM to 50 µM. Most preferably PEG is comprised in a stock solution at a concentration of 2.5 µM or at a concentration of 25 µM, or even most preferably in the range of 1 µM to 10 µM. A suitable stock solution comprises 5 µM PEG.

$R_1$, if present, is comprised in a stock solution at a concentration in the range from 0.1 µM to 1000 µM, preferably in the range from 0.1 µM to 500 µM or 0.1 µM to 300 µM, more preferably 0.1 µM to 300 µM or 0.1 µM to 200 µM. Most preferably $R_1$ is comprised at a concentration of 10 µM or at a concentration of 100 µM. A suitable stock solution comprises 5 µM $R_1$.

(BX)n is comprised in a stock solution at a concentration in the range from 0.4 µM to 1000 µM, preferably in the range from 0.4 µM to 750 µM or 0.4 µM to 500 µM, more preferably 0.4 µM to 250 µM or 0.4 µM to 100 µM. Most preferably, (BX)n is comprised at a concentration of 10 µM or 100 µM. A suitable stock solution comprises 5 µM (BX)n.

The NCP is comprised at a concentration in the range from 0.1 µM to 250 µM, preferably in the range from 0.1 µM to 125 µM or 0.1 µM to 75 µM, more preferably 0.1 µM to 75 µM or 0.1 µM to 50 µM. Most preferably, the NCP is comprised at a concentration in the range from 0.1 µM to 25 µM. A suitable stock solution comprises 5 µM NCP.

The stock solutions can be prepared in any suitable buffer solution. Preferred in accordance with the invention is phosphate buffered saline (PBS) to prepare the stock solutions.

Peptide-polyethylene glycol-conjugate and NCP are present in the biomatrix layer of the invention in a predefined ratio peptide-polyethylene glycol-conjugate:NCP in the range between 1:100 and 100:1, preferably between 1:90 and 90:1, 1:80 and 80:1, 1:70 and 70:1 or 1:60 and 60:1, more preferably 1:50 and 50:1, 1:40 and 40:1, 1:30 and 30:1, 1:20 and 20:1 or 1:10 and 10:1, most preferably in the range between 1:9 and 9:1, 1:8 and 8:1, 1:7 and 7:1, 1:6 and 6:1, 1:5 and 5:1, 1:4 and 4:1, 1:3 and 3:1, 1:2 and 2:1, especially preferred 1:1 or between 1:2 and 2:1.

The ratio peptide-polyethylene glycol-conjugate:NCP has been found to influence the porosity of the biomatrix layer. To adjust the porosity of the biomatrix layer, the ratio of peptide-polyethylene glycol (PEG)-conjugate:NCP is typically varied in the aforementioned ranges, wherein the lower the proportion of NCP is, the higher is the porosity of the biomatrix layer. Highly porous thin layer films could be generated by lowering the proportion of NCP in the biomatrix layer. For example, by mixing of 50 µM NCP and 50 µM peptide-polyethylene glycol-conjugate (resulting in 25 µM NCP and 25 µM peptide-polyethylene glycol-conjugate in the mixture) led to a coherent film, lowering the NCP concentration to 10 µM resulted in a highly porous structure.

Altering the peptide-polyethylene glycol-conjugate:NCP ratio can also change the gelation speed. Increased gelation speed leads to increased porosity of the biomatrix layer. The gelation speed is also influenced by the inclusion of the bio-functional peptide motifs at position $R_1$. Inclusion/presence of $R_1$, such as the integrin-binding motif RGDSP (SEQ ID NO: 16) in the peptide-polyethylene glycol-conjugate decreases the gelation rate and thus leads to less porous biomatrix layers. The formation of a porous structure can further be affected by selecting the type of NCP. When, for example, heparin was replaced by dextran sulfate, which accelerates the gelation, a highly porous structure of the biomatrix layer was achieved. E.g., Mixing 50 µM dextran sulfate and 50 µM star-PEG-KA7 led to highly porous biomatrix layer films.

The gelation rate can for example be increased by using a mixture of a peptide-polyethylene glycol (PEG)-conjugate of formula (Ia) with a peptide-polyethylene glycol (PEG)-conjugate of formula (Ib), wherein the proportion of the compound of formula (Ia), in which $R_1$ is present, is at least 10%; and/or by using a mixture of a peptide-polyethylene glycol (PEG)-conjugate of formula (II), with a peptide-polyethylene glycol (PEG)-conjugate of formula (IIa), wherein the proportion of the compound of formula (II) is at least 10%.

By selecting the type of the peptide-polyethylene glycol (PEG)-conjugate, it is also possible to adjust the biomatrix layer to a specific application or use. If it is desired to produce a biomatrix layer, which is inert to cell adhesion, then only peptide-polyethylene glycol (PEG)-conjugate of formula (Ib) or formula (IIa), where $R_1$ is not present, is used in the hydrogel. If adhesion should be provided to cells, at least 10% of a peptide-polyethylene glycol (PEG)-conjugate of formula (I) or formula (II), where $R_1$ is present, should be mixed in. For certain biomedical applications, it is also possible to produce a biomatrix layer, wherein the peptide-polyethylene glycol (PEG)-conjugate consists to 100% of a peptide-polyethylene glycol (PEG)-conjugate formula (I) or formula (II), where $R_1$ is present.

The stiffness of the biomatrix layer film can be tuned by multiple parameters, e.g. NCP type, peptide-polyethylene glycol-conjugate:NCP ratio, and extension of the peptide sequences at position $R_1$ and/or (BX)n.

Interestingly, NCP concentration showed strong effects on the stiffness of hydrogel films when a peptide-polyethylene glycol-conjugate was used, in which $R_1$ was present. For example, increasing the heparin concentration resulted in stiffer hydrogels. This effect was not observed, when a peptide-polyethylene glycol-conjugate was used, in which $R_1$ was absent.

Also the extension of $R_1$, which is defined to be a peptide consisting of 5 to 30 amino acids, is influencing the stiffness. The stiffness of the biomatrix layer is the higher, the lower the number of amino acids contained in $R_1$ is.

Varying the ratio of peptide-polyethylene glycol (PEG)-conjugate:NCP in the range between 100:1 and 1:100 also leads to an adjustment of the stiffness; wherein the higher the proportion of sulfated oligosaccharide is the higher is the stiffness of the biomatrix layer. The stiffness can also be adjusted by increasing or decreasing the gelation rate, wherein decreasing the gelation rate results in a stronger stiffness of the biomatrix layers.

As already mentioned before, slower gelation leads to more compact film formation, as described above, thus resulting in stiffer biomatrix layers. The replacement of heparin with another NCP, e.g. chondroitin sulfate A and dermatan sulfate decreased the gelation rate and thereby increased the stiffness of the biomatrix layer.

The stiffness of the biomatrix layer may be further adjusted by selecting the amino acid X in the (BX)n peptide of the peptide-polyethylene glycol-conjugate especially in regard to the negative charge of the amino acid in this position; wherein the higher the negative charge of the selected amino acid for X is the stronger is the stiffness of the biomatrix layer. The stiffness of the biomatrix layer may be further adjusted by selecting the number of replicates n of the motif (BX)n within the peptide-polyethylene glycol-conjugate; wherein the larger n is the stronger is the stiffness of the biomatrix layer.

The stiffness of the thin layer matrix may be further adjusted by selecting the amino acid B in the (BX)n peptide. Using arginine in the position of B leads to stiffer biomatrix layers. If softer biomatrix layers are desired, then B is preferably lysine.

By selecting the type of the peptide-polyethylene glycol (PEG)-conjugate, it is also possible to adjust the stiffness of the biomatrix layer. The following types of peptide-polyethylene glycol (PEG)-conjugates can be used/incorporated in the hydrogel to adjust the stiffness of the biomatrix layer:
  a peptide-polyethylene glycol (PEG)-conjugate of formula (I) or formula (II), where $R_1$ is present,
  a peptide-polyethylene glycol (PEG)-conjugate of formula (Ia) or formula (II), where $R_1$ is present,
  a mixture of a peptide-polyethylene glycol (PEG)-conjugate of formula (Ia) with a peptide-polyethylene glycol (PEG)-conjugate of formula (Ib), wherein the proportion of the conjugate of formula (I), in which $R_1$ is present, is at least 10%,
  a mixture of a peptide-polyethylene glycol (PEG)-conjugate of formula (II) with a peptide-polyethylene glycol (PEG)-conjugate of formula (IIa), wherein the proportion of the conjugate of formula (II) in said mixture is at least 10%;
  a peptide-polyethylene glycol (PEG)-conjugate of formula (Ib) or formula (IIa), where $R_1$ is not present,
wherein the presence of $R_1$ generally leads to an decrease of the stiffness.

In a further embodiment of the invention, biomatrix layers are preferred, which comprise the peptide-polyethylene glycol-conjugate at a concentration in the range from 0.1 µM to 1,000 µM, such as 0.1 µM to 250 µM, preferably in the range from 0.1 µM to 125 µM or 0.1 µM to 75 µM, more preferably 0.1 µM to 75 µM or 0.1 µM to 50 µM. Most preferably PEG is comprised at a concentration of 2.5 µM or at a concentration of 25 µM, or even most preferably in the range of 1 µM to 10 µM. In another preferred embodiment, PEG is comprised in the range from 900 µM to 1,000 µM.

It is a great advantage of the biomatrix layer of the invention that its porosity and stiffness can be adapted to its desired function, i.e. for mimicking both the protein and NCP parts of ECM and providing an ECM for adhesion and growing/differentiating cells.

The biomatrix layer according to the invention differs from conventional hydrogels in particular in its thickness. The thickness of the biomatrix layer is typically in the range from 3 nm to 40 µm, preferably 3 nm to 1 µm or 3 nm to 500 nm, more preferably 3 nm to 100 nm, most preferably 3 nm to 50 nm or 3nm to 10 nm; and can be adjusted by selecting the type of NCP, selecting the concentration of the peptide-polyethylene glycol (PEG)-conjugate and NCP and by varying the ratio of peptide-polyethylene glycol (PEG)-conjugate:NCP. The thickness of the biomatrix layer can further be adjusted by controlling the volume of raw material, which is applied to area to be coated, for example the volume of raw materials applied to a well of a 96-well plate.

With regard to the type of NCP, thin hydrogels in the range from 3 nm to 40 µm can be obtained by using heparan sulfate, chondroitin sulfate, dermatan sulfate, keratan sulfate, dextran sulfate or hyaluronic acid instead of heparin.

The concentration of the peptide-polyethylene glycol (PEG)-conjugate and NCP in the buffer solution is typically selected from the range between 0.1 and 250 µM, most preferably in the range from 1 to 10 µM for PEG and 0.1 to 25 µM for NCP. The higher the concentration of the peptide-polyethylene glycol (PEG)-conjugate and NCP is, the higher is the thickness of the resulting biomatrix layer.

The ratio of peptide-polyethylene glycol (PEG)-conjugate:NCP in the buffer solution of step iii) is typically varied in the range between 1:100 and 100:1, preferably in the range from 1:6 and 6:1, most preferably in the range from 1:2 and 2:1, wherein the lower the proportion of NCP is, the thinner is the resulting biomatrix layer.

The biomatrix layer according to invention, with the composition as described herein has several advantageous characteristics. In one aspect, the biomatrix layer is highly resistant against deionized water, DMF, DMSO, ethanol, 1M HCl and 1 M NaOH.

The biomatrix layer of the invention shows a very good biocompatibility and has the advantage of a defined chemical composition. The biomatrix layer of the invention is thus broadly applicable in biomedicine.

It is a further advantage of the biomatrix layer of the invention, that the cell load/surface coverage of the biomatrix layer can be adjusted, in particular increased by
  selecting the type of NCP used to produce the biomatrix layer; and/or
  using a peptide-polyethylene glycol (PEG)-conjugate of formula (I), (Ia) or of formula (II); or
  using a mixture of a peptide-polyethylene glycol (PEG)-conjugate of formula (Ia), with peptide-polyethylene glycol (PEG)-conjugate of formula (Ib), wherein the proportion of the compound of formula (I), in which $R_1$ is present, is at least 10%, and/or
  using a mixture of a peptide-polyethylene glycol (PEG)-conjugate of formula (II), with peptide-polyethylene glycol (PEG)-conjugate of formula (IIa), wherein the proportion of the compound of formula (II), in which R$_1$ is present, is at least 10%;
wherein surface coverage of the biomatrix layer with cells increases by increasing the content or proportion of the peptide-polyethylene glycol (PEG)-conjugate of formula (I), (Ia) or formula (II), i.e. by the presence of the bio-functional peptide R$_1$.

Heparin, heparin sulfate, chondroitin sulfate, dermatan sulfate, keratan sulfate as well as hyaluronic acid contribute to an increased cell load and surface coverage of the biomatrix layer by cells.

When the biomatrix layer according to the invention comprises cells, the cells are typically mammalian cells, insect cells, bacteria or yeast cells, preferably mammalian cells, most preferably human cells or human cell lines. In a particularly preferred embodiment, the cells are human stem cells, more preferably human primary stem cells, or most preferably iPS derived stem cells of human origin. Example for cells, which may be comprised in or onto the biomatrix layer, are human fibroblast cells, mesenchymal stromal cells (MSC), neuronal progenitor cells (NPC) or human umbilical vein endothelial cells (HUVEC).

A further great advantage of the present invention is that all building blocks of the biomatrix layer of the invention are variable and thus form the basis of library for purpose-specific creation of biomatrix layers. For example, by selecting the building blocks from said library, it is possible to create a biomatrix layer, which is capable of binding a specific cell type or cell line by adhesion on the surface of the biomatrix layer. The biomatrix layer of the invention is further suitable to promote cell survival, to control cell proliferation, to preserve stemness and to guide cell differentiation into specific cell lineages.

Thus, in a further, most preferred embodiment, the invention provides a combinatorial library of building blocks of the biomatrix layer, which comprises, essentially consists of or consists of
  NCPs,
  PEGs,
  (BX)n peptides, wherein B, X and n are as defined herein, and
  R$_1$ peptides, wherein R$_1$ is as defined herein.

The library is suitably provided in the form of stock solutions in PBS (phosphate-buffered saline). More preferably, it is provided a combinatorial library of building blocks of the biomatrix layer according to any one of the preceding claims, comprising individual stock solutions of said building blocks in PBS buffer, comprising, essentially consisting of or consisting of
  2.5 µM to 7.5 µM, preferably 5.0 µM NCPs selected from the group consisting of heparin, heparan sulfate, chondroitin sulfate, dermatan sulfate, keratan sulfate, dextran sulfate and hyaluronic acid,
  2.5 µM to 7.5 µM, preferably 5.0 µM PEGs, preferably 4-arm star-PEGs in the range of 4 kD to 40 kD;
  2.5 µM to 7.5 µM, preferably 5.0 µM (BX)n peptides selected from the group consisting of the peptides with SEQ ID NOs: 1 to 14, and
  2.5 µM to 7.5 µM, preferably 5.0 µM R$_1$ peptides peptide selected from the group consisting of the peptides with SEQ ID NOs: 15 to 353.

Said stock solutions have the advantage that the biomatrix layer of the invention can be easily prepared by mixing suitable amounts of the individual stock solutions. Suitable amount in this regard means that coacervation and matrix layer formation occurs.

In a further preferred embodiment, the invention provides a kit for producing a purpose-specific biomatrix layer of the invention, comprising the stock solutions in PBS comprising 2.0 µM to 7.5 µM of
  a NCP,
  a PEG,
  a library of (BX)n peptides, wherein B, X and n are as defined herein,
  a library of R$_1$ peptides, wherein R1 is as defined herein, and
  instructions for use the afore mentioned agents to produce a purpose-specific biomatrix layer of the invention.

As regards the library and kit above, the NCP is preferably selected from heparin, heparan sulfate, chondroitin sulfate, dermatan sulfate, keratan sulfate, dextran sulfate, hyaluronic acid, polystyrene sulfate (PSS), sulfated alginate, sulfated hyaluronic acid, cyclic dextran sulfate, cyclic dextran phosphate and phytic acid, most preferably selected from heparin, heparan sulfate, chondroitin sulfate, dermatan sulfate, keratan sulfate, dextran sulfate, hyaluronic acid, The PEG is a linear PEG or starPEG as defined herein, preferably a 4-arm starPEG with a molecular weight between 4 kD and 40 kD, most preferably 10 kD.

The library of (BX)n peptides consists preferably of the peptides according SEQ ID Nos.: 1 to 14.

The library of R$_1$ peptides consists preferably of the peptides according SEQ ID Nos.: 15 to 353. In a preferred embodiment, the library of R$_1$ peptides does not contain the peptide RGDSP (SEQ ID NO: 17). Accordingly, in a most preferred embodiment, the library of R$_1$ peptides consists of the peptides according SEQ ID Nos.: 15, 16, 18 to 353.

The library and kit can also be used to screen for an ideal composition of the biomatrix layer of the invention, specifically adapted to a desired purpose or use of the biomatrix layer. A desired purpose or use is for example adapting or preparing a biomatrix layer, which is specifically suitable for adhesion of specific cells or cell lines, for example human cells or human cell lines, a particular human stem cells, preferably human primary stem cells, or most preferably iPS derived stem cells of human origin. For example, the ideal composition of a biomatrix layer for adhesion of human fibroblast cells, mesenchymal stromal cells (MSC), neuronal progenitor cells (NPC) or human umbilical vein endothelial cells (HUVEC) can be screened using the library or kit of the invention. Another desired purpose or use is adapting or preparing a biomatrix layer, which is specifically suitable for coating biomedical devices to improve biocompatibility of the biomedical devices.

Such screening can for example be performed in HTS format as a high throughput screen. For example, the formation of the biomatrix layer may be carried in a well plate, such as a 96- or 384-well plate, wherein each well will be loaded with a different mixture of building blocks selected from the library of the invention.

In a further embodiment of the invention, the biomatrix layer is capable of forming a 3D biomatrix layer, which is especially suitable for providing a biomatrix layer for the targeted release of therapeutic reagents, wherein via a corresponding method therapeutic reagents may be entrapped or encapsulated within the above-described biomatrix layer. The group of each of the utilized therapeutic reagents comprises preferably cells, cell spheres (e.g. mesensphere, neurosphere) or organoids or a morphogen or an active pharmaceutical ingredient.

When the biomatrix layer according to the invention comprises cells as the therapeutic agent, the cells are as defined above.

An organoid is a miniaturized and simplified version of an organ produced in vitro in three dimensions that shows realistic micro-anatomy. Organoids are derived from one or a few cells from a tissue, embryonic stem cells or induced pluripotent stem cells, which can self-organize in three-dimensional culture owing to their self-renewal and differentiation capacities.

The 3D biomatrix layer of the present invention can provide a convenient in vitro model for the study of complex cell-cell and cell-matrix interactions in the absence of exogenous substrates and may benefit the development of regenerative medicine strategies, which is not possible with traditional cell culture methods, which rely on growing cells as monolayers. Mesenchymal stem cell (MSC) spheroids, or "mesenspheres" of different sizes can be formed and maintained in the 3D biomatrix layer of the present invention. 3D culturing of mesenspheres have been shown to exhibit no evidence of cell necrosis or differentiation, while mesenspheres in differentiation media exhibited differentiation similar to conventional 2D culture methods based on histological markers of osteogenic and adipogenic commitment. Furthermore, when plated onto tissue culture plates, cells that had been cultured within mesenspheres in growth medium recovered morphology typical of cells cultured continuously in adherent monolayers and retained their capacity for multi-lineage differentiation potential. In fact, more robust matrix mineralization and lipid vacuole content were evident in recovered MSCs when compared to monolayers, suggesting enhanced differentiation by cells cultured as 3D spheroids. Thus, a 3D culture system for mesenchymal stem cells may circumvent limitations associated with conventional monolayer cultures and enhance the differentiation potential of multipotent cells (Baraniak P. R., McDevitt T. C., Scaffold-free culture of mesenchymal stem cell spheroids in suspension preserves multilineage potential. Cell Tissue Res. 2012 March; 347(3):701-11).

The 3D biomatrix layer of the present invention can further provide a convenient environment to produce neurospheres. A neurosphere is a culture system composed of free-floating clusters of neural stem cells. Neurospheres provide a method to investigate neural precursor cells in vitro. Putative neural stem cells are suspended in a medium lacking adherent substrates but containing necessary growth factors, such as epidermal growth factor and fibroblast growth factor. This allows the neural stem cells to form into the characteristic 3-D clusters. A typical use of the neurosphere is in neurosphere assays.

A morphogen is a substance whose non-uniform distribution governs the pattern of tissue development in the process of morphogenesis or pattern formation, one of the core processes of developmental biology, establishing positions of the various specialized cell types within a tissue. More specifically, a morphogen is a signaling molecule that acts directly on cells to produce specific cellular responses depending on its local concentration.

Typically, morphogens are produced by source cells and diffuse through surrounding tissues in an embryo during early development, such that concentration gradients are set up. These gradients drive the process of differentiation of unspecialized stem cells into different cell types, ultimately forming all the tissues and organs of the body. The control of morphogenesis is a central element in evolutionary developmental biology.

Mammalian morphogens suitable for use in the biomatrix layer of the invention include retinoic acid, sonic hedgehog (SHH), transforming growth factor beta (TGF-β)/bone morphogenic protein (BMP), and Wnt/beta-catenin. During development, retinoic acid, a metabolite of vitamin A, is used to stimulate the growth of the posterior end of the organism. Retinoic acid binds to retinoic acid receptors that acts as transcription factors to regulate the expression of Hox genes. Exposure of embryos to exogenous retinoids especially in the first trimester results in birth defects. TGF-β family members are involved in dorsoventral patterning and the formation of some organs. Binding to TGF-β to type II TGF beta receptors recruits type I receptors causing the latter to be transphosphorylated. The type I receptors activate Smad proteins that in turn act as transcription factors that regulate gene transcription. Sonic hedgehog (Shh) are morphogens that are essential to early patterning in the developing embryo. Shh binds to the Patched receptor which in the absence of Shh inhibits the Smoothened receptor. Activated smoothened in turn causes Gli1, Gli2, and Gli3 to be translocated into the nucleus where they activate target genes such at PTCH1 and Engrailed.

When the biomatrix layer according to the invention comprises an active pharmaceutical ingredient as the therapeutic agent, the active pharmaceutical ingredient is typically selected from anti-cancer compounds, anti-coagulation compounds, anti-inflammatory compounds, immune-suppressive compounds, therapeutic antibodies, diagnostic reagents, hormones, growth factors, cytokines, small molecules as inhibitors for growth factors, small molecules as inhibitors for cytokines, aptamer-inhibitors for growth factors and aptamer-inhibitors for cytokines. In a particularly preferred embodiment, the active pharmaceutical ingredient is selected from doxorubicin, paclitaxel, cyclosporin A, tacrolimus, rapamycin, anti-VEGF antibody, and anti-TNF-α antibody.

When the biomatrix layer according to the invention comprises a morphogen as the therapeutic agent, the morphogen is typically selected from TNF-α, TGF-β, IFN-γ, FGF, VEGF, and EGF.

Hydrogels are particularly useful for the delivery of drugs, in particular protein therapeutics. Hydrogels are biocompatible, and provide a gentle environment for proteins to minimize denaturation of the proteins. The proteins are physically entrapped within the gels or bound to the gel by electrostatic interactions between the natural protein and the NCP or between covalently coupled protein-(BX)n peptide and NCP.

Proteins are released by degradation of the biomatrix or release kinetic given by the electrostatic interaction. Degradable R1 can be incorporated within the PEG polymers that form the hydrogel, and via degradation of segments within the gel, the proteins will be released as the gel degrades.

The invention further relates to processes for preparing a biomatrix layer according to the invention.

In a first aspect, said process for preparing a biomatrix layer according to the invention comprises the steps of
i) preparing a peptide-polyethylene glycol (PEG)-conjugate of formula (Ia):

PEG-R$_1$-(BX)$n$        (Ia), and optionally of formula (II)

PEG-CWGG-R$_1$-GG-(BX)$n$        (II)

wherein
B is lysine or arginine, X is selected from alanine, glycine, serine, threonine, tyrosine, glutamic acid or aspartic acid and n is an integer selected from 5, 6, 7, 8, 9, 10, 11, 12, 13, 14, 15, 16, 17, 18, 19 and 20; and R₁ may be absent or is a peptide comprising 5 to 30 amino acids;

ii) mixing said polyethylene glycol (PEG)-conjugate of with a NCP;

iii) adding the mixture of step ii) in a suitable buffer solution or medium, wherein said polyethylene glycol (PEG)-conjugate of formula (Ia) or of formula (II) is contained in said buffer solution at a concentration in the range of 0.1 µM to 250 µM and said NCP is contained in said buffer solution at a concentration in the range of 0.1 µM to 250 µM; and iv) forming the biomatrix layer by gelation, and optional, when said hydrogel comprises cells or organoids, the additional steps of:

v) seeding said cells or organoids onto the biomatrix layer obtained by step iv) as described above; and vi) incubating said biomatrix layer and said seeded cells or organoids to facilitate cell adhesion to the biomatrix layer.

It should be recognized that the advantages and advantageous embodiments described above for the biomatrix layer according to the invention equally apply to the processes for preparing said biomatrix layer such that it shall be referred to the above.

In a further embodiment, said peptide-polyethylene glycol (PEG)-conjugate is a conjugate of formula (Ib):

PEG-(BX)n                               (Ib)

wherein B, X and n are as defined herein.

In a further embodiment, said conjugate is a conjugate of formula (IIa):

PEG-CWGG-(BX)n                    (IIa)

wherein B, X and n are as defined herein.

As described above for the biomatrix layer of the invention, said peptide-polyethylene glycol-conjugate can also be a mixture of a peptide-polyethylene glycol-conjugate of formula (Ia) and a peptide-polyethylene glycol-conjugate of formula (Ib) or a peptide-polyethylene glycol-conjugate of formula (II) and a peptide-polyethylene glycol-conjugate of formula (IIa) with suitable proportions as described herein. In these mixtures, up to three different conjugates according to formula (I), (Ia), (II) or (IIa), which contain different bio-functional peptides at position R₁, can be contained, respectively.

Steps ii) of mixing said polyethylene glycol (PEG)-conjugate of with a NCP and iii) of adding the mixture of step iii) in a suitable buffer solution or medium are very simple processes and are preferably performed in aqueous solution, buffer or cell culture medium. A suitable buffer is for example PBS (phosphate buffered saline).

In a most preferred embodiment, the invention provides a process for preparing a biomatrix layer comprising the steps of i) preparing a peptide-polyethylene glycol (PEG)-conjugate of formula (Ia):

PEG-R₁-(BX)n                             (Ia), and optionally of formula (II)

PEG-CWGG-R₁-GG-(BX)n              (II)

wherein

PEG is a 10 kD 4-arm star-PEG;

(BX)n is a peptide selected from SEQ ID NOs: 1 to 14, and

R₁ may be absent or is a bio-functional peptide selected from SEQ ID NOs: 15 to 353;

ii) dissolving said peptide-polyethylene glycol (PEG)-conjugate and NCP in said buffer at 100× of the final concentration;

iii) diluting and mixing solutions of step ii) in a suitable buffer solution, wherein polyethylene glycol (PEG)-conjugate of formula (Ia) or of formula (II) and said NCP are each contained in said buffer solution at a concentration in the range of 0.1 µM to 250 µM; and iv) forming the biomatrix layer by gelation, and optional, when said hydrogel comprises cells or organoids, the additional steps of:

v) seeding said cells or organoids onto the biomatrix layer obtained by step iv) as described above; and vi) incubating said biomatrix layer and said seeded cells or organoids to facilitate cell adhesion to the biomatrix layer.

In an alternative embodiment, the process can be altered such that in first step, a matrix without the bio-functional peptide R₁ is prepared and that in a second step, a post-modification is performed by adding a peptide comprising the bio-functional peptide, wherein said added peptide is selected from R₁-(BX)n, CW-R₁-GG-(BX)n and CWGG-R₁-GG-(BX)n. The resulting biomatrix layer is comparable to the biomatrix layer obtained with the original process of the invention.

The formation of the biomatrix layer, i.e. the gelation can be performed at a temperature in the range of 0° C. to 50° C. Preferably, the gelation is performed at a temperature in the range of 10° C. to 45° C., 20° C. to 40° C. or 30° C. to 35° C. Most preferably, the gelation is performed at a temperature in the range from room temperature to 37° C.

As described above several characteristics of the biomatrix layer of the invention, such as thickness, porosity, stiffness and cell load can be tuned by selecting different building blocks to create the biomatrix layer. Accordingly, the invention does also provide processes for adjusting the thickness, porosity, stiffness and cell load of the biomatrix layer of the invention.

In one embodiment, the invention provides a process for adjusting the thickness of the biomatrix layer, preferably in the range of 3 nm to 40 µm comprising selecting the type of NCP used to produce the biomatrix layer; and/or selecting the concentration of peptide-polyethylene glycol (PEG)-conjugate:NCP; and/or varying the ratio of peptide-polyethylene glycol (PEG)-conjugate:NCP in the buffer solution of step iii) in the range between 1:1 and 1:25; wherein the lower the proportion of NCP is the thinner is the resulting biomatrix layer; and/or controlling the volume of raw material, which is applied to area to be coated, wherein the rawer material is applied to a specific area, the greater is the thickness or the biomatrix layer.

For example, the thickness of the biomatrix layer can be decreased by using heparin sulfate, chondroitin sulfate, heparin sulfate, dermatan sulfate or hyaluronic acid for preparing the biomatrix layer.

In a further embodiment, the invention provides a process for adjusting the porosity of the biomatrix layer by varying the ratio of peptide-polyethylene glycol (PEG)-conjugate:NCP or in the buffer solution or medium of step iii) in the range between 1:100 and 100:1; wherein the lower the proportion of sulfated oligosaccharide is, the higher is the porosity of the biomatrix layer; and/or increasing or decreasing the gelation rate, wherein increasing the gelation rate results in an increased porosity of the biomatrix layers.

The gelation rate can, e.g., be increased by selecting the type of sulfated oligosaccharide, e.g. dextran sulfate; and/or using a peptide-polyethylene glycol (PEG)-conjugate of formula (I), (Ia) or of formula (II); or using a mixture of a peptide-polyethylene glycol (PEG)-conjugate of formula (Ia), with peptide-polyethylene glycol (PEG)-conjugate of formula (Ib), wherein the proportion of the compound of formula (Ia), in which $R_1$ is present, is varied between 0 and 100%, wherein for cell adhesion purposes the proportion of the compound of formula (Ia) in the mixture is at least 10% and/or using a mixture of a peptide-polyethylene glycol (PEG)-conjugate of formula (II), with peptide-polyethylene glycol (PEG)-conjugate of formula (IIa), wherein the proportion of the compound of formula (IIa) is varied between 0 and 100%, wherein for cell adhesion purposes the proportion of the compound of formula (II) in the mixture is at least 10%.

In a further embodiment, the invention provides a process for adjusting the stiffness of the biomatrix layer comprising selecting the type of sulfated oligosaccharide used to produce the biomatrix layer; and/or selecting the amino acid at position X within the (BX)n peptide-polyethylene glycol-conjugate in particular in regard to its negative charge; wherein the higher the negative charge of the selected amino acid for X is, the stronger is the stiffness of the biomatrix layer; and/or selecting the number of replicates n of the motif (BX)n within the peptide-polyethylene glycol-conjugate; wherein the larger n is, the stronger is the stiffness of the biomatrix layer; and/or varying the ratio of peptide-polyethylene glycol (PEG)-conjugate:NCP in the buffer solution or medium of step iii) in the range between 100:1 and 1:100; wherein the higher the proportion of NCP is, the higher is the porosity of the biomatrix layer; and/or increasing or decreasing the gelation rate, wherein decreasing the gelation rate results in a stronger stiffness of the biomatrix layers.

In a further embodiment, the invention provides a process for adjusting the stiffness of the biomatrix layer comprising using chondroitin sulfate or dermatan sulfate to produce the biomatrix layer; and/or using a peptide-polyethylene glycol (PEG)-conjugate of formula (I), (Ia) or of formula (II); or using a mixture of a peptide-polyethylene glycol (PEG)-conjugate of formula (Ia), with peptide-polyethylene glycol (PEG)-conjugate of formula (Ib), wherein the proportion of the compound of formula (Ia), in which $R_1$ is present, is varied between 0 and 100%, wherein for cell adhesion purposes the proportion of the compound of formula (Ia) is at least 10% and/or using a mixture of a peptide-polyethylene glycol (PEG)-conjugate of formula (II), with peptide-polyethylene glycol (PEG)-conjugate of formula (IIa), wherein the proportion of the compound of formula (II), in which $R_1$ is present, is varied between 0 and 100%, wherein for cell adhesion purposes the proportion of the compound of formula (II) is at least 10%.

In a further embodiment, the invention provides a process for adjusting the cell load/surface coverage of the biomatrix layer, comprising selecting the type of sulfated oligosaccharide used to produce the biomatrix layer; and/or using a peptide-polyethylene glycol (PEG)-conjugate of formula (I), (Ia) or of formula (II); or using a mixture of a peptide-polyethylene glycol (PEG)-conjugate of formula (Ia), with peptide-polyethylene glycol (PEG)-conjugate of formula (Ib), wherein the proportion of the compound of formula (Ia), in which $R_1$ is present, is varied between 0 and 100%, wherein for cell adhesion purposes the proportion of the compound of formula (Ia) is at least 10%; and/or using a mixture of a peptide-polyethylene glycol (PEG)-conjugate of formula (II), with peptide-polyethylene glycol (PEG)-conjugate of formula (IIa), wherein the proportion of the compound of formula (II), in which $R_1$ is present, is varied between 0 and 100%, wherein for cell adhesion purposes the proportion of the compound of formula (II) is at least 10%, wherein surface coverage of the biomatrix layer with cells increases by increasing the content or proportion of the peptide-polyethylene glycol (PEG)-conjugate of formula (Ia) or formula (II).

The cell load/surface coverage of the biomatrix layer can be increased by using heparin, heparin sulfate, chondroitin sulfate, dermatan sulfate, keratan sulfate or hyaluronic acid to produce the biomatrix layer.

In a further aspect, the invention provides a process for preparing a biomatrix layer, which comprises cells or organoids. In this case, the process further comprises the additional steps of:

v) seeding said cells or organoids on the biomatrix layer obtained by step iv) as described above; and vi) incubating said biomatrix layer and said seeded cells or organoids to facilitate cell adhesion to the biomatrix layer.

Alternatively, the cells or organoids are not added to the already formed biomatrix layer, but are already added during the process of preparing the biomatrix layer according to the invention. Suitably, the cells are then already contained in the medium, such as a cell culture medium of step iii).

In a further aspect, the invention provides a process for preparing a biomatrix layer comprising cells or organoids, wherein said process optionally comprises the further step of:

vii) culturing said cell- or organoid-containing biomatrix layer.

The culturing of said cell- or organoid-containing biomatrix layer is typically performed in liquid culture in a culture medium, which supports the growth and development or which maintains the viability of the adhered or encapsulated cells or organoids. Culturing is typically performed at a temperature in the range of in the range of 0° C. to 50° C., preferably in the range of 10° C. to 45° C., 20° C. to 40° C. or 30° C. to 35° C. Most preferably, culturing is performed at a temperature in the range from room temperature to 37° C., which is best for maintaining the viability and/or for growth and further development of the adhered or encapsulated cells.

When cells are provided onto the biomatrix, $1\text{-}10^6$ cells/$cm^2$, preferably 10 to $10^6$ cells/$cm^2$ more preferably $10^2$ to $10^5$ cells/$cm^2$, most preferably $10^3$ to $10^5$ cells/$cm^2$ are seeded onto the biomatrix layer of the invention.

When cells are encapsulated into the biomatrix, $1\text{-}10^{10}$ cells/mL, preferably 10 to $10^9$ cells/mL, more preferably $10^2$ to $10^8$ cells/mL, most preferably $10^3$ to $10^7$ cells/mL are used for cell encapsulation.

A typical culture medium, in which the cells are grown and provided for seeding onto or into the biomatrix layer of the invention is DMEM (Dulbecco's Modified Eagle Medium, Gibco), preferably DMEM containing 10% FBS Fetal Bovine Serum).

In a further embodiment, the invention provides a process for producing a multilayer biomatrix containing cells, in which cells of different types are physically segregated through step-wise pipetting using self-assembling approach. Said method comprises the steps of
  i) forming a first biomatrix layer film;
  ii) seeding a first type of cells onto the first biomatrix layer film,
  iii) incubation of the seeded cells to form a first cell layer,
  iv) forming a second biomatrix layer film on top of the first cell layer,
  v) incubation, e.g. overnight,
  vi) seeding a second type of cells onto second biomatrix layer film to form a sandwich structure,
  vii) culturing the sandwich structure, e.g. for one day.

The liquid-liquid phase separation mechanism allowed the simple pipetting of the building blocks of the first and second biomatrix layer films directly into cell culture media. Sandwich formation does not involve chemical reaction and causes minimal physical stress to the cells. As shown in the working examples herein, each cell type expanded while remaining their characteristic phenotype. Therewith a successful application of the biomatrix layer for sandwich cell culture assays could be demonstrated. Segregation of different cells in distinct layers is very important for orchestrating their biological functions in vivo. The layer-by-layer method using an easy pipetting procedure permits the construction of various models, not only in more native-like co-culture environment but also compatible for microscopy imaging.

In a further aspect of the invention, a process for preparing a biomatrix layer is provided, wherein said biomatrix layer comprises a morphogen or an active pharmaceutical ingredient. The addition of the morphogen or active pharmaceutical ingredient may be done in step ii) or iii) of the above described method.

Said active pharmaceutical ingredient is typically contained in the mixture of step iii) in a final concentration of 0.01 µg/l to 2.0 g/l; preferably in the range of 0.1 µg/l to 1.5 g/l, 1.0 µg/l to 1.0 g/l or 10 µg/l to 0.5 g/l, more preferably in the range of 0.1 mg/l to 0.1 mg/l, most preferably in the range of 1.0 mg/l to 0.01 g/l.

The invention further provides a biomatrix layer, which is obtainable by a process according to the invention. It should be recognized that the advantages and advantageous embodiments described above for the biomatrix layer and the processes according to the invention equally apply to the biomatrix layer, which is obtainable a process of the invention, such that it shall be referred to the above.

In yet a further aspect, the invention provides the use of a biomatrix layer according to the invention in biomedical applications, such as neuroprostheses, biosensors, nerve grafts, cell culture, tissue or cell storage, drug delivery and coating of biomedical devices. The non-covalent biomatrix layer of the invention is for example an ideal tool for screening tissue specific extracellular matrix mimics for single and multiple layered cell culture models.

The invention is described in more detail by 16 figures and 19 working examples.

EXAMPLE 1

Peptide Synthesis

All peptides mentioned herein are produced by utilizing a standardized-fluorenylmethoxycarbonyl chemistry (FMOC chemistry) on a solid phase with 2-(1H-benzotriazol-1-yl)-1,1,3,3 tetramethyluronoiumhexafluorophosphate-activation (HBTU-activation) in an automatic solid phase peptide synthesizer (ResPep SL, Intavis, Cologne, Germany). To obtain good peptide quality, each amino acid was coupled two times with the fivefold excess, wherein all non-reacting amino groups were protected with acetic acid anhydride. For cleaving the peptide from the resin, the resin was treated for one and one half hour with a mixture of trifluoroacetic acid (TFA) triisopropylsilane (TIS)/water/dithiothreitol (DTT), wherein these components are present in a ratio of 90 (v/v):2.5 (v/v):2.5 (v/v):2.5 (m/v).

The peptides were dissolved in water, which contained 2 mg/ml tris(2-carboxyethyl)phosphine (TCEP). The peptide purification was carried out by means of reverse-phase high pressure liquid chromatography (UPLC) on a preparative HPLC-device (Prostar™, Agilent Technologies, Santa Clara, USA) which was provided with a preparative C18-column (AXIA™ 1001 A grain size 10 µm, 250×30 mM, Phenomenex Torrance USA). The peptide was eluted from the column by utilizing a gradient of 5% to 100% solvent B at 20 ml/min, wherein solvent A is 0.1% trifluoroacetic acid (TFA) in water and solvent B is 0.1% TFA and 5% water in acetonitril.

The purity was confirmed through analytical reverse-phase ultrahigh pressure liquid chromatography (UPLC Aquity™ with UV detector, Waters, Milford Mass., USA) provided with an analytical C18-column (AQUITY™ UPLC BEH C18, grain size 1.7 µm, 50×2.1 mM, Waters, Milford, Mass., USA) by utilizing an isocratic gradient and an electrospray-ionisation-mass-spectrometry (ESI-MS) (AQUITY™ TQ detector, Waters, Milford, Mass., USA). The peptide was dry frozen into a white powder (CHRIST ALPHA™ 2-4LD plus+ vacuubrand RZ6) and at 4° C. under dry conditions stored for not more than one week prior to further treatment.

EXAMPLE 2

Synthesis of Peptide-PEG-Conjugates

The synthesis of the peptide-starPEG conjugates utilized in biomatrix assembly was conducted via Michael-type addition reactions between 10 kDa maleimide functionalized four-arm polyethylene glycol (starPEG, JenKem Technology, Beijing, China) and cysteine-terminated peptides. Both components were dissolved in PBS (pH 7.4) and mixed in a molar ratio of 1:5 (starPEG:peptide) with a total concentration of 80 mg/ml. The reaction mixture was quickly sealed and stirred on a stirring plate at 750 rpm at room temperature (24° C.) for 2 hours. The crude product was dialyzed to remove uncoupled peptides and salt in a dialysis tube with an 8 kDa cutoff (Spectrum Laboratories, Inc., Rancho Dominguez, Calif., USA) against 10 l water under constant water exchange for 2 days. Afterwards the product was analyzed by reverse phase UPLC (ACQUITY system, Waters, Milford, Mass., USA) using an analytical reverse phase C18 column for protein separation (Phenomenex, Torrance, Calif., USA) and an isocratic gradient. The dialyzed product in water was lyophilized.

EXAMPLE 3

Production of the Biomatrix Layers

Heparin sodium salt from porcine intestinal mucosa was bought from Millipore (MERCK KGaA (Darmstadt, Germany). Chondroitin sulfate A sodium salt from bovine trachea, dextran sulfate sodium salt (5 kDa) from *Leuconostoc* spp., heparan sulfate sodium salt from bovine kidney and dermatan sulfate from porcine intestinal mucosa were bought from Sigma-Aldrich Co. LLC. (St. Louis, Mo., USA). Peptide-starPEG conjugates and NCP were dissolved in PBS (pH 7.4) or cell culture medium and filtered (0.22 µM). Both components were then mixed in equal volume to finally 200 µl using 96 well plates and 60 µl using µ-angiogenesis slides (ibidi GmbH, Martinsried, Germany)). Thin layers were formed at 24° C. or at 37° C., 95% humidity and 5% $CO_2$.

EXAMPLE 4

Gelation Time Analysis

Biomatrix layers were prepared in µ-angiogenesis slides. Directly after mixing the components the slides were put into a chamber with 37° C. mounted on the microscope (Axio Observer Z1, Zeiss, Oberkochen, Germany). Bright field pictures of the forming biomatrix layer were taken after at different time points.

EXAMPLE 5

Analysis of Biomatrix Layer Structure in 3 Dimensions

Biomatrix layers were washed with PBS or full cell culture medium three times and the structure of the thin layer was analyzed in by using fluorescence spinning disc confocal microscopy (Axio Observer Z1 (Zeiss, Oberkochen, Germany) with spinning disk unit CSU-X1M 5000 dual cam (Yokagawa, Tokyo, Japan)). Image analysis was performed by using ImageJ 1.48v[23]. The thickness was then determined by calculating the FWHM (full-width-at-half-maximum) for the intensity profiles and measuring the distance of these FWHM between the left and the right shoulder of the plot[24].

EXAMPLE 6

Stiffness Analysis Using Atomic Force Microscopy (AFM)

For these AFM studies, the biomatrix layers were prepared in 24 well plates in a volume of 1.2 ml. Once the gels were formed the supernatant was exchanged before the experiment. Spherical silica particles with diameters of 10 µm and 20 µm were glued onto the tip less triangular pyrex-nitride cantilevers, PNP-TR-TL of length 200 µm and force constant of about 0.08 N/m (NanoWorld AG, Neuchâtel, Switzerland). All force measurements were performed in PBS (pH 7.4) using a Nanowizard II (JPK Instruments AG, Berlin, Germany) mounted on an optical microscope (AxioObserver Z1). Force curves were mapped in 8×8 grid over the sample surface area of 10×10 µm. The depth of indentation made was optimized to 400-500 nm where the young's moduli tends towards a constant value and the substrate below does not influence the calculations. The values were averaged from biomatrix layers independently prepared and measured at two different days with three grids measured per sample. The JPKSPM data processing software (JPK Instruments AG) was used to fit the obtained force to the Hertz model to calculate the Young's moduli considering a spherical indenter. Controls for the measurements were made by probing 0.2% Agarose gels and Matrigel[25].

EXAMPLE 7

General Cell Culture

Primary human mesenchymal stromal cells (MSC), HUVEC and HeLa cells and glioblastoma U-251 MG cells were used. Each cell type was grown in appropriate media: HDFn: medium 106 with 2% low serum growth supplements; MSC: DMEM GlutaMax low glucose (1 g/l) with 10% FBS, NPC: Neurobasal medium with 2% B27 supplement, 1% GlutaMax and 1% Pen/Strep—for expansion with 10 ng/ml EGF and FGF2 (Peprotech, Rocky Hill, N.J., USA) (media until here all Thermo Fisher Scientific), HUVEC: Endothelial cell growth medium and 2% supplement mix (PromoCell GmbH, Heidelberg, Germany). Except NPC all cell types were grown in uncoated T-25 flasks from Greiner Bio-One International AG (Kremsmünster, Austria). NPC were expanded by growing on poly-D-lysine/laminin (PDL: Sigma-Aldrich Co. LLC.; laminin: Roche Diagnostics, Rotkreuz, Switzerland) coated culture flasks. NPC originate from adult mouse gentate gyrus within hippocampus.

EXAMPLE 8

Cell Culture on Biomatrix Layer

Different RGDSP concentrations were achieved by mixing KA7-starPEG with KA7-RGDSP-starPEG in the according molar ratios. The formation of the biomatrix layers was allowed overnight while stored at room temperature. Protein coatings made with 60 µl in µ-angiogenesis slides of 50 mg/ml fibronectin or 5 µg/ml of laminin were used as controls. The supernatant of the formed biomatrix was removed and cells were added in full cell culture medium to the biomatrix layers and control surfaces. Full cell culture medium was changed after first day of culture and then every second day.

EXAMPLE 9

Layer-by-Layer Co-Culture

The first layer of the biomatrix was prepared by mixing 5 µM KA7-RGDSP-starPEG and 0.7 mg/ml chondroitin sulfate A (same weight per volume as 50 µM 14 kDa heparin). After seeding of HDFn and overnight incubation, the second thin layer was formed. 14 kDa heparin and KA7-RGDSP-starPEG conjugate were dissolved in full HDFn cell culture medium and filtered through a 0.22 µm centrifuge tube filter. These solutions were mixed (by vortexing) to reach a final concentration of 3.5 mM 14 kDa heparin and 2.5 mM KA7-RGDSP-starPEG conjugate. To form the second layer 5 µl of the mixture were injected into the cell culture medium on the HDFn layer. After another overnight incubation step MSC were added and cultured further in full MSC cell culture medium.

EXAMPLE 10

Staining Hippocampal Neural Precursor Cells for Stemness Markers

Cells were fixed with 4% PFA for 10 minutes and then permeabilised with 0.1% Triton X-100 for 10 minutes, followed by blocking with 10% donkey serum for 1 hour. Subsequently, cells were incubated with rabbit anti-Sox2 (MERCK KGaA, Darmstadt, Germany) and mouse anti-Nestin antibodies (Becton, Dickinson and Company (BD), Franklin Lakes, N.J., USA) diluted 1:500 for 2 hours. Secondary antibodies, anti-mouse Alexa Fluor 488 and anti-rabbit DyLight 549 (Dianova GmbH, Hamburg, Germany) were applied at 1:500 for 1 hour. Finally, nuclei were stained with Hoechst33342 (1:4000). Samples were imaged with inverted confocal microscope Axio Observer Z1 (Plan-Apochromat 10×/0.45 M27) (Zeiss) equipped with a spinning disk unit CSU-X1M 5000 dual cam (Yokagawa). To measure cell size and number ImageJ 1.48v was used.

EXAMPLE 11

Differentiation Assay of Hippocampal Neural Precursor Cells

Differentiation was introduced by withdrawal of EGF and step-wise reduction of FGF2. First, cells were cultured with complete media and 5 ng/ml FGF2 for 2 days. Then cells were cultured 4 more days without growth factors before being fixed with 4% PFA for 10 minutes. Cells were the permeabilised with 0.1% Triton X-100 for 10 minutes, followed by blocking with 10% donkey serum for 1 hour. Subsequently, cells were incubated with mouse anti-Map2ab (Sigma-Aldrich Co. LLC.) and rabbit anti-GFAP (Agilent Technologies, Santa Clara, USA) diluted 1:500 for 2 hours. Secondary antibodies, anti-mouse Alexa Fluor 488 and anti-rabbit DyLight 549 were applied at 1:500 for 1 hour (Dianova GmbH). Finally, nuclei were stained with Hoechst33342 (1:4000). Cells were imaged with an inverted confocal microscope Axio Observer Z1 (Plan-Apochromat 20×/0.8) (Zeiss) and analyzed manually with the ImageJ cell counter plugin.

EXAMPLE 12

Immunocytochemistry for Cell Spreading

Prior to immunostaining, samples were fixed with 4% PFA for 15 minutes at room temperature (24° C.) and blocked in 0.25% bovine serum albumin, 1% Tergitol solution and 0.1% heparin in PBS (pH 7.4) for 1 hour. Next, phalloidin was applied in blocking buffer for 1 hour. Afterwards 0.1 µg/ml DAPI in PBS was applied for 5 minutes followed by three times 5 minutes washing with the buffer. Samples were imaged with inverted confocal microscope Axio Observer Z1 (Plan-Apochromat 10×/0.45 M27) (Zeiss) equipped with a spinning disc unit CSU-X1M 5000 dual cam (Yokagawa). For image analysis ImageJ 1.48v was used.

EXAMPLE 13

Staining for Cell Proliferation

Cell proliferation was evaluated using Click-iT® EdU Imaging Kit (555 nm excitation) according to manufacturer's instructions (Thermo Fisher Scientific). Briefly, cells were incubated with 10 µM EdU for 2 hours at 37° C. followed by fixation with 4% PFA and permeabilization with 0.5% Triton X-100 in PBS (pH 7.4). Finally, the EdU was detected with Click-iT® reaction cocktail and counter-stained with Hoechst 33342. The staining was visualized with inverted confocal microscope Axio Observer Z1 (Plan-Apochromat 10×/0.45 M27) (Zeiss) equipped with a spinning disc unit CSU-X1M 5000 dual cam (Yokagawa).

Tissue engineers require a versatile platform to experiment with various compositions to mimic different biological environments. In practice, a promising approach often involves simple design and a feasible method. Moreover, the potential biomedical applications also demand for the use of safe building blocks. The presented versatile physical biomatrix layer system is mediated by the unspecific electrostatically driven liquid-liquid phase separation (coacervation) followed by the gelation through specific peptide/NCP interaction. The self-assembling system allows creating a 3D matrix by just one pipetting step. Furthermore, more complex structures such as multiple cell layers can easily build up. It also uses the safe building blocks: while many sulfated oligosaccharides are FDA approved compounds, the conjugation of synthetic peptides with the most widely used biopolymer PEG also minimizes the potential risk of both biological contamination and immunogenicity. Therewith, an easy-to-use 3D biomatrix system to tailor defined biomatrix compositions and to complement conventional 2D surface-coatings of large proteins from animal extraction is provided.

Different NCP can be incorporated into the biomatrix layers, allowing the use of all NCP from ECM in their native forms. Varying concentrations of peptide and NCP influences the chemical composition, mechanical property and morphology. Thus, by using different building blocks of NCP and peptide-starPEG conjugates, the biomatrix can be tailored to fit the requirements of different cell types. Optimal compositions of defined 3D matrix films for culturing primary cells such as MSC and NPC were identified, providing the environment for their adhesion, proliferation and differentiation.

EXAMPLE 14

Figure 10:
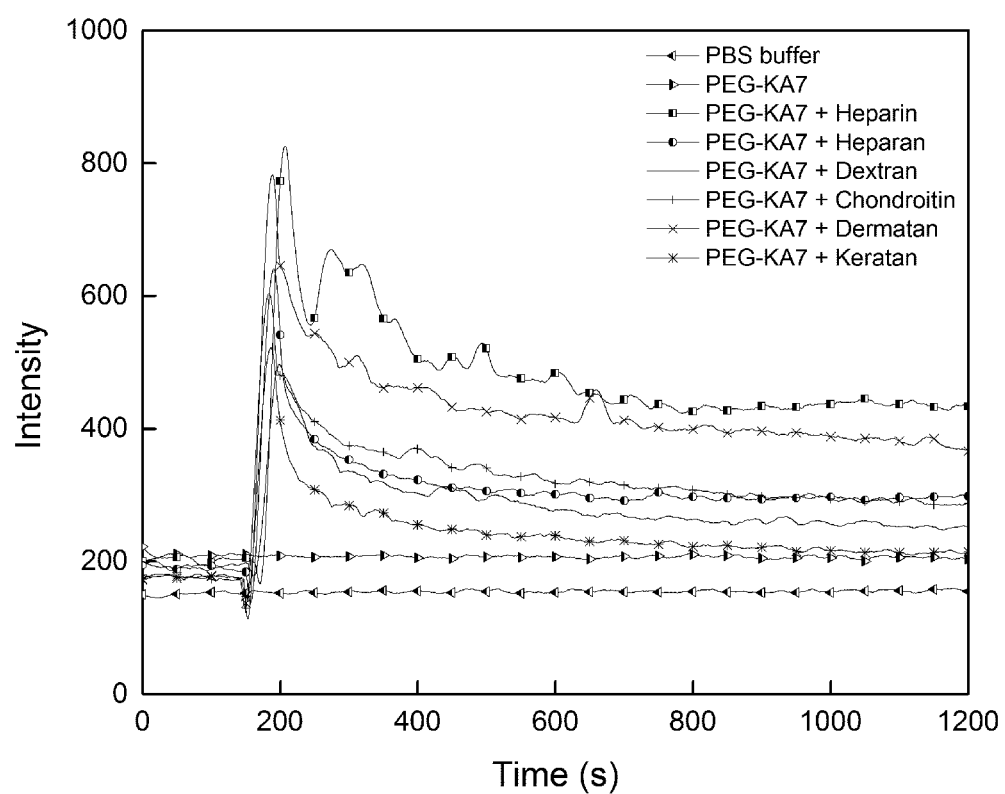
FIG. 10 shows light scattering measured indicating coacervation of peptide-PEG conjugate with different NCPs when NCPs are added.

Light Scattering Measurements Indicating Coacervation of Peptide-PEG Conjugate with Different NCP and with Different $R_1$ Peptides Light scattering ability of the solution containing PEG-KA7 and the individual NCPs was measured on a PerkinElmer LS45 fluorescence spectrophotometer at 500 nm for 1800 seconds with 500 data points sampled. Each NCP was added to a solution of PEG-KA7 to a final concentration of 5 µM for each of the components. Baselines were initially observed using PBS buffer and PEG-KA7, marked with triangles. The NCP solutions were added at 180 s, after a steady baseline was observed. The scattering of light increased instantly at the point of the addition of NCP, indicating the turbidity as a result of coacervation (FIG. 10). The light scattering decreased gradually over time, hinting the deposition of the coacervates. This measurements indicate glycosaminoglycan-peptide interaction for glycosaminoglycans of heparin, heparan sulfate, dextran sulfate, chondroitin sulfate, dermatan sulfate, and keratan sulfate.

Figure 11:
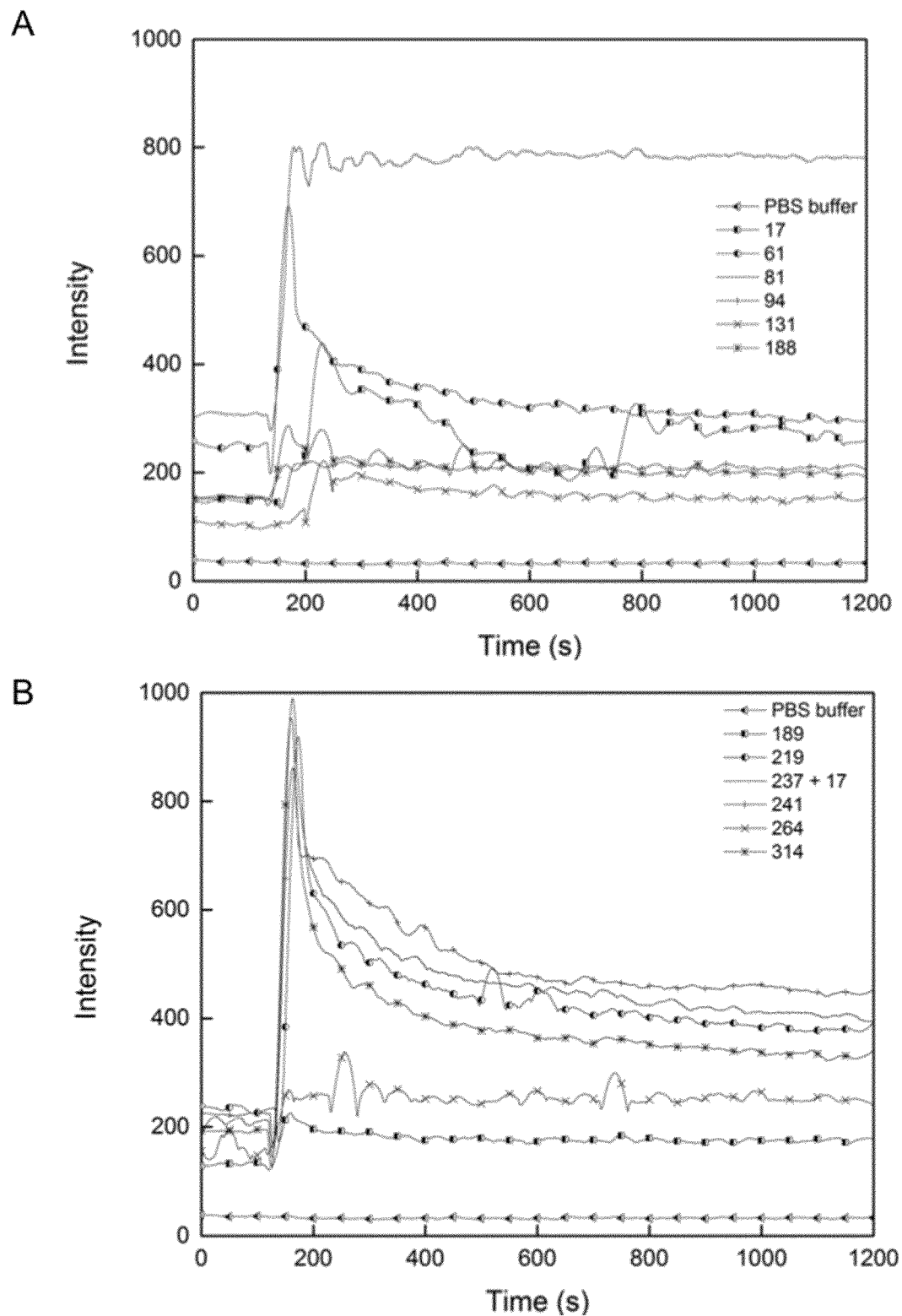
FIG. 11 shows light scattering measured indicating coacervation of PEG-$R_1$ conjugates with heparin comprising different $R_1$ peptides. The numbers in the figure legend represent the SEQ ID NOs. of the different $R_1$ peptides comprised in the tested PEG-$R_1$ conjugates. Light scattering ability of the solution containing mixture of peptide-polyethylene glycol-conjugate comprising PEG, $R_1$ and KA7 and heparin, was measured on a PerkinElmer LS45 fluorescence spectrophotometer at 500 nm for 1200 s. Heparin was added to a solution of peptide-polyethylene glycol-conjugate comprising PEG, $R_1$ and KA7 to a final concentration of 5 µM for each of the components. Baselines were initially observed using PBS buffer or 5 µM peptide-polyethylene glycol-conjugate comprising PEG and KA7 solution, marked with triangles. The heparin solutions was added at 150 s, after a steady baseline was observed. The scattering of light increased instantly, indicating the turbidity as a result of coacervation. All measurements indicate interaction of the tested peptide-polyethylene glycol-conjugate comprising PEG, $R_1$ and KA7 conjugates with heparin as a representative for NCPs.

Light scattering measurements were also performed with PEG-peptide conjugates with heparin comprising different $R_1$ peptides (FIG. 11). Light scattering ability of the solution containing mixture of PEG-R$_1$-KA7 and heparin, was measured on a PerkinElmer LS45 fluorescence spectrophotometer at 500 nm for 1200 s. Heparin was added to a solution of PEG-R$_1$-KA7 to a final concentration of 5 µM for each of the components. Baselines were initially observed using PBS buffer or 5 µM PEG-KA7 solution, marked with triangles. The heparin solutions was added at 150 s, after a steady baseline was observed. The scattering of light increased instantly, indicating the turbidity as a result of coacervation. All measurements indicate interaction of the tested PEG-R$_1$-KA7 conjugates with heparin as an representative for NCPs.

EXAMPLE 15

Figure 12:
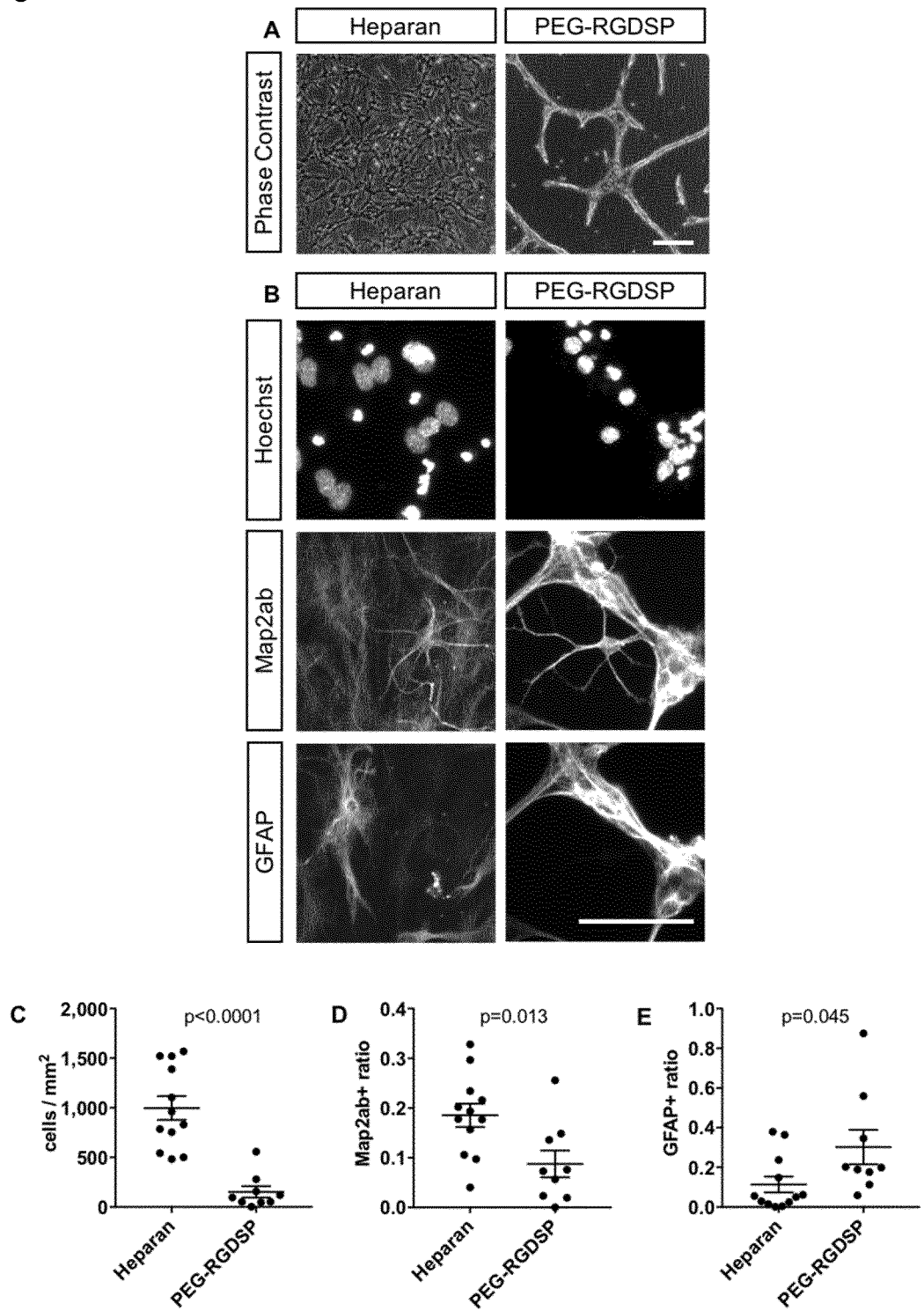
FIG. 12 shows results of the analysis of primary human mesenchymal stromal cells (MSC) being expanded in standard media containing 10% FBS and serum-free media.

Analysis of Primary Mouse Neuronal Progenitor Cells (NPC) Differentiation on Biomatrix Layers Comprising of Heparan Sulfate and KA7-RGDSP-starPEG Biomatrix layers were formed by mixing 5 µM of heparan sulfate (heparan) with PEG-RGSP-KA7. Conventional PEG hydrogel coatings were prepared by thio-maleimide Michael-type addition using a RGDSP peptide containing two terminal cysteines and the 4arm-starPEG. (FIG. 12A) Phase contrast images show differential growth of neural precursor at day 5 of the differentiation protocol. (FIG. 12B) Fluorescent images highlight nuclei through staining of DNA (Hoechst), neuronal cells (Microtubule-Associated Protein 2ab (Map2ab)), and astrocytes (glial fibrillary acidic protein (GFAP)) cells after 6 days of culture on both surfaces. Scale bars is 100 µm. Results of the image analysis are shown as (FIG. 12C) cell numbers, (FIG. 12D) rate of MAP2ab-positive cells and (E) rate of GFAP-positive cells in relation to total cell counts. Data represent the mean±SEM from 2 independent experiments in triplicate conducted in parallel with 2 primary cells lines derived from independent isolations. Cell numbers are higher for heparan biomatrix coatings at highly significant levels by t-Test with 419)=5.73. The proportion of Map2ab positive neurons are increased (419)=2.74) whereas less GFAP positive astrocytes are detected (t(19)=2.15) on heparan biomatrices in comparison to PEG-RGDSP gels.

EXAMPLE 16

Analysis of Primary Human Mesenchymal Stromal Cells (MSC) Being Expanded in Standard Media Containing 10% FBS and Serum-Free Media Primary human mesenchymal stromal cells (MSC) have been cultured in standard, serum-containing media (10% FBS in DMEM GlutaMax, Invitrogen) for 3 days and doubling times of cells were compared to defined, serum-free media (StemPro, Invitrogen) when growing of biomatrix layers or plastic. Doubling time of cells was calculated according the formula: $T_d=(t_{day3}-t_{day1})\times\log(2)/\log(N_{day3}/N_{day1})$, where t represents the time points of cell counting and N the cell number counted.

Figure 13:
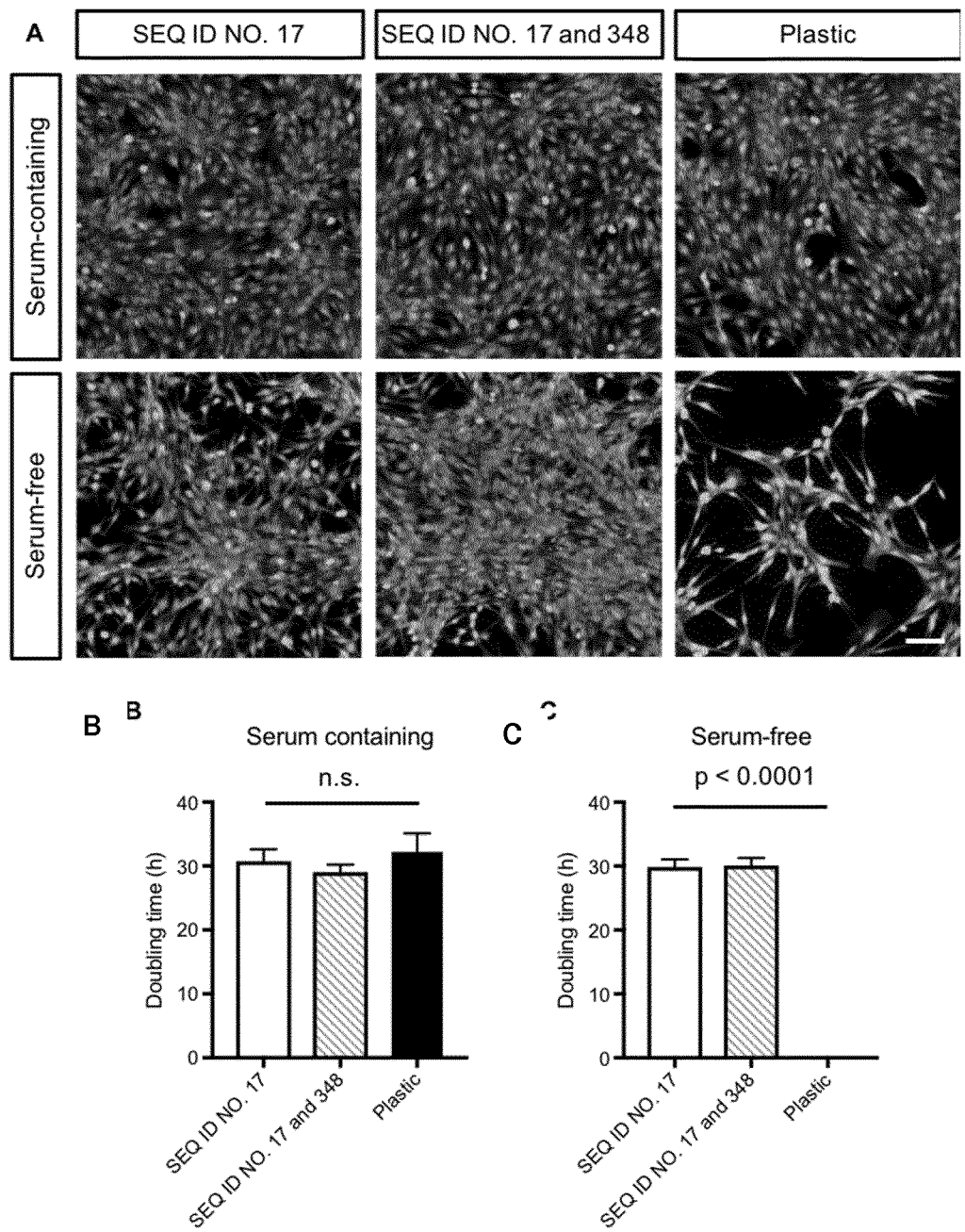
FIG. 13 shows results of the analysis of primary human mesenchymal stromal cells (MSC) being expanded in standard media containing 10% FBS and serum-free media. (A) MSC have been kept in culture for 3 days before being fixed and stained with Hoechst and CellMaskGreen. Surfaces were coated by mixing 5 μM Dextran-sulfate (DS) with either 2.5 μM peptide-polyethylene glycol-conjugate comprising PEG, RGDSP and KA7 (comprising the $R_1$ peptide of SEQ ID NO. 17) and 2.5 μM PEG-CWGG-KA7 without $R_1$ sequence or 2.5 μM peptide-polyethylene glycol-conjugate comprising PEG, RGDSP and KA7 and 2.5 μM peptide-polyethylene glycol-conjugate comprising PEG, YRSRKYSSWYVALKRK and KA7 (comprising the $R_1$ peptide of SEQ ID NO. 348) to form the biomatrix layer. Plain plastic were used for comparison. Scale bar is 100 μm. Cell counts derived from fluorescent images of fixed cells after 1 day and 3 days of culture were used to calculate the doubling time (Td). (B) Td for MSC cultured on the biomatrix coatings compared to plastic in serum-containing media. (C) Td for MSC cultured on the biomatrix coatings compared to plastic in serum-free media. Data represent the mean±SD from 2 independent experiments. Differences between values are analyzed with t-test and p-values are indicated in the figure (n.s.—not significant).

The biomatrix layers were made of the NCP dextran sulfate and different mixtures of PEG-peptide conjugate. One biomatrix layer was made by mixing PEG-RGDSP-KA7 (SEQ ID NO. 17) with PEG-KA7 at 1:1 ratio. The second biomatrix layer was made by mixing PEG-RGDSP-KA7 (SEQ ID NO. 17) and 2.5µM PEG-YRSRKYSSWY-VALKRK-KA7 (SEQ ID NO. 348). MSC were seeded at 7,000 cells/cm$^2$. A first set of samples was fixed after 24 hours in culture (day 1) using 4% PFA. A second set of samples was fixed after about 72 hours in culture (day 3). Cells were stained with Hoechst33342 (1:4000, Invitrogen) and CellMaskGreen (1:5000, Invitrogen). Images were acquired and analyzed for cell numbers using a BioTek Lionheart FX automated microscope (10× objective) and Gen5 software (version 3.03). For calculation of the doubling time, the exact interval time between day 1 and day 3 was utilized. The results (FIG. 13) show uniform cell grow and similar doubling time on all surfaces when serum-containing media is used. In serum-free culture conditions, plastic surfaces did not provide suitable environment for growth of MSC as indicated by creation of cell colonies and not quantifiable doubling times as cells got fewer within the 3 days of culture. In conclusion, biomatrix layers with both mixtures of peptides presented provide a defined environment to enable MSC expansion with serum-free media.

EXAMPLE 17

Figure 14:
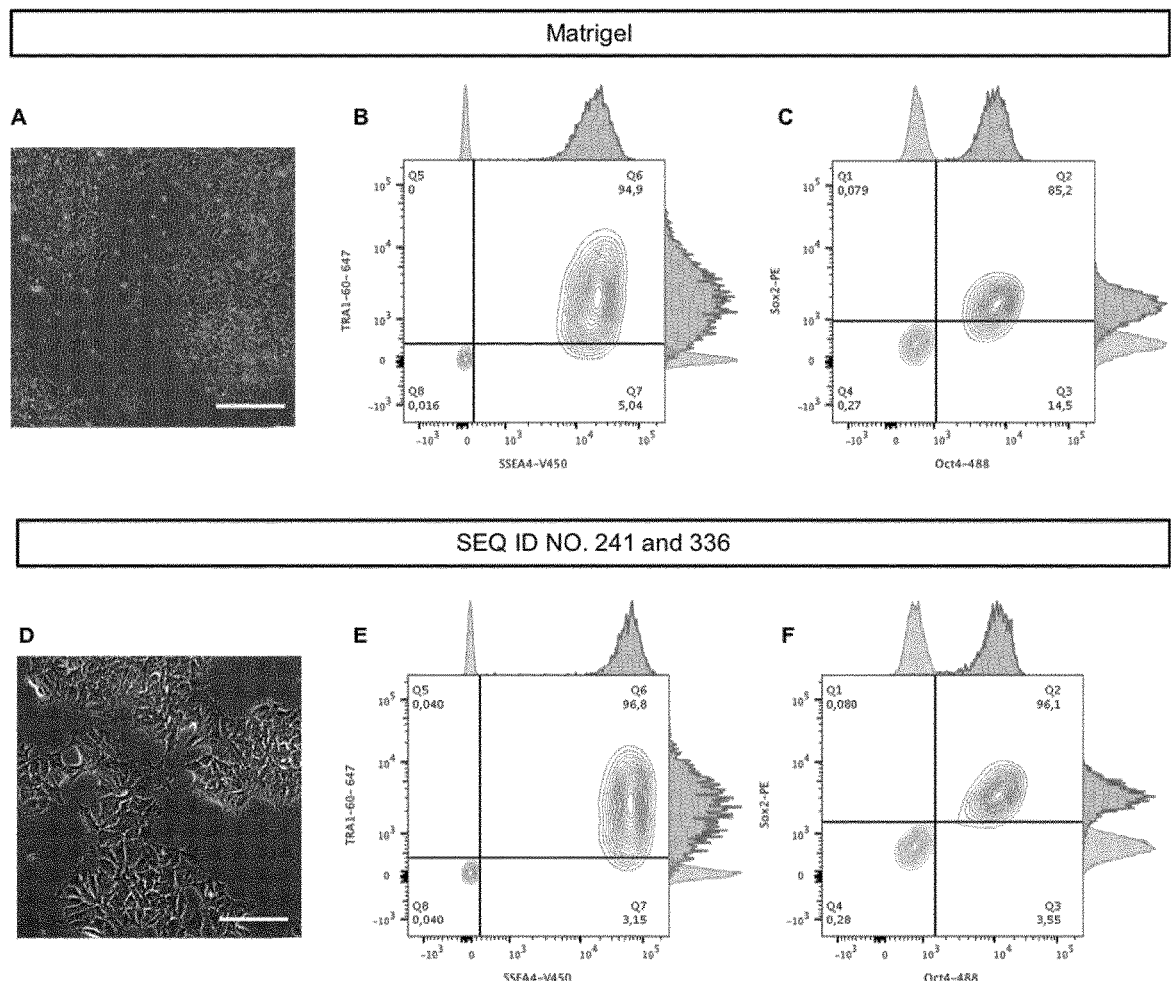
FIG. 14 shows results of the analysis of stemness marker expression by flow cytometry of human induced pluripotent stem cells (iPSC) after 5 passages of culture. iPSC have been expanded on A-C) biomatrix layer made of a mixture of 5 μM heparin with 2.5 μM peptide-polyethylene glycol-conjugate comprising PEG, PQVTRGDVFTMP and KA7 (comprising $R_1$ peptide of SEQ ID NO. 241) and 2.5 μM peptide-polyethylene glycol-conjugate comprising PEG, WQPPRARI and KA7 (comprising $R_1$ peptide of SEQ ID NO. 336). D-F) Coatings prepared of 9 μg/mL Matrigel® solution was used for comparison. A) and D) present phase contrast images (10×). B, C, E, F) represent histograms and contour plots of the fluorescent signal intensity of the analyzed stemness markers TRA1-60 and SSEA4 or Sox2 and Oct4. Scale bar is 100 μm.

Analysis of Stemness Marker Expression by Flow Cytometry of Human Induced Pluripotent Stem Cells (iPSC) After 5 Passages of Culture Induced pluripotent stem cells (iPSC), line CRTD-1, have been seeded on biomatrix layer made of a mixture of 5 µM heparin with 2.5 µM PEG-PQVTRGDVFTMP-KA7 (SEQ ID NO. 241) and 2.5 µM PEG-WQPPRARI-KA7 (SEQ ID NO. 336). Coatings prepared of 9 µg/mL Matrigel® (Corning) solution was used for comparison. mTeRS (STEM-CELL technologies) was used as culture media. Upon 70-80% of confluence, iPSC have been split onto new surfaces by using Accutase (Invitrogen) for detachment and at splitting ratios of 1:4 to 1:20. A PSC 4-Marker Immunocytochemistry kit (Molecular probes, ThermoFisher) including primary antibodies against TRA1-60, SSEA4, Sox2, and Oct4 was used to stain the fixed cells for flow cytometry analysis using a LSR II flow cytometer (BD). Antibodies were applied as indicated by the manufacturer at 1:100 dilution. Results are shown in FIG. 14.

EXAMPLE 18

Figure 15:
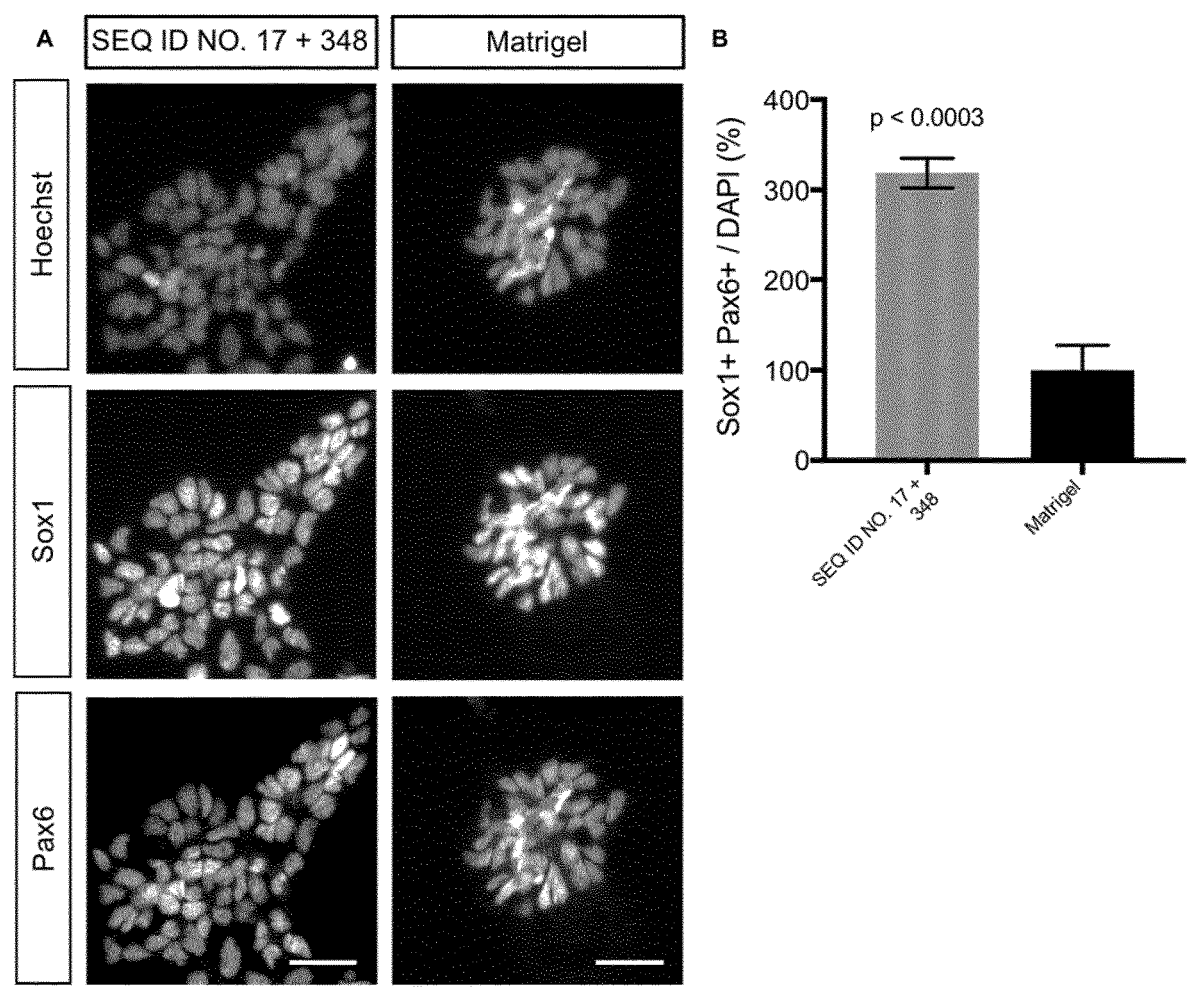
FIG. 15 shows results of the analysis of stemness marker expression by immunocytochemistry of neural precursor cells (NPC) derived from human induced pluripotent stem cells (iPSC) after 5 days of culture. A) NPC have been expanded on biomatrix layer made of a mixture of 5 μM heparin with 2.5 μM RGDSP (SEQ ID NO. 17) and 2.5 μM YRSRKYSSWYVALKRK-conjugated PEG (SEQ ID NO. 348). Coatings prepared of 9 μg/mL Matrigel® solution was used for comparison. Cells were fixed with 4% PFA and stained for Hoechst33342, Sox1 and Pax6 as presented with the fluorescent images. B) Cell numbers of Pax6 and Sox1 positive cells were set in relation to total cell counts. Scale bar is 100 μm.

Analysis of Stemness Marker Expression by Immunocytochemistry of Neural Precursor Cells (NPC) Derived from Human Induced Pluripotent Stem Cells (iPSC) After 5 Days of Culture Neural precursor cells (NPC), derived from human induced pluripotent stem cells were cultured in standard expansion condition. Expansion media was prepared by mixing DMEM and Neurobasal media (Invitrogen) at ration of 1:1 and addition of 1% B27, 0.05% N2, 2% Glutamine and 2% Pen/Strep (all Invitrogen). Further, CHIR 99021 (3 µM final conc., Axon MedChem), ascorbic acid (final conc. 200 µM, SigmaAldrich) and Pumorphamine (final conc. 0.5 µM, Santa Cruz) were added. After 5 days in culture, cells were fixed with 4% PFA and stained with Hoechst33342 (1:4000, Invitrogen), Sox1 (1:300, R&D) and Pax6 (1:300, Biolegend). Secondary antibodies with fluorescent label of AF488 and Cy3 were purchased from Dianova and used at 1:500 dilution. Images were acquired using a BioTek Lionheart FX automated microscope (10× objective) and analyzed for cell counts (Hoechst signal) and fluorescent signal intensities of Sox1 and Pax6 with the Gen5 software (version 3.03). Results indicate significant higher numbers of cells that are positive for stemness markers Sox1 and Pax6 on the biomatrix layer compared to Matrigel coated surfaces. Results are shown in FIG. 15.

EXAMPLE 19

Fluorescent Images of Neural Precursor Cells (NPC) Derived from Human Induced Pluripotent Stem Cells (iPSC) After 10 Days of Differentiation Into Neurons as Indicated by Immunocytochemistry Straining with anti-Tuj1 Antibody NPCs have been first expanded on biomatrix layers made of a mixture of 5 μM dermatan sulfate with 5 μM of PEG-$R_1$-KA7 comprising a single or two different peptide sequences of the peptide library given by table 2. After 2 days of expansion, media was changed to patterning media for 6 days, followed by 4 days in maturation media. Cells were fixed with 4% PFA and stained for anti-Tuj1 antibody as presented with the fluorescent images. The 5 shown images present functional $R_1$ sequences that promoted neuronal outgrowth. Scale bar is 100 μm. The $R_1$ peptide library was employed to identify functional peptide sequences promoting neuronal development of neural precursor cells (NPC), derived from human induced pluripotent stem cells. All biomatrix surfaces were prepared from stock solutions of 5 μM of heparan sulfate and 5 μM of PEG-$R_1$-KA7.

Figure 16:
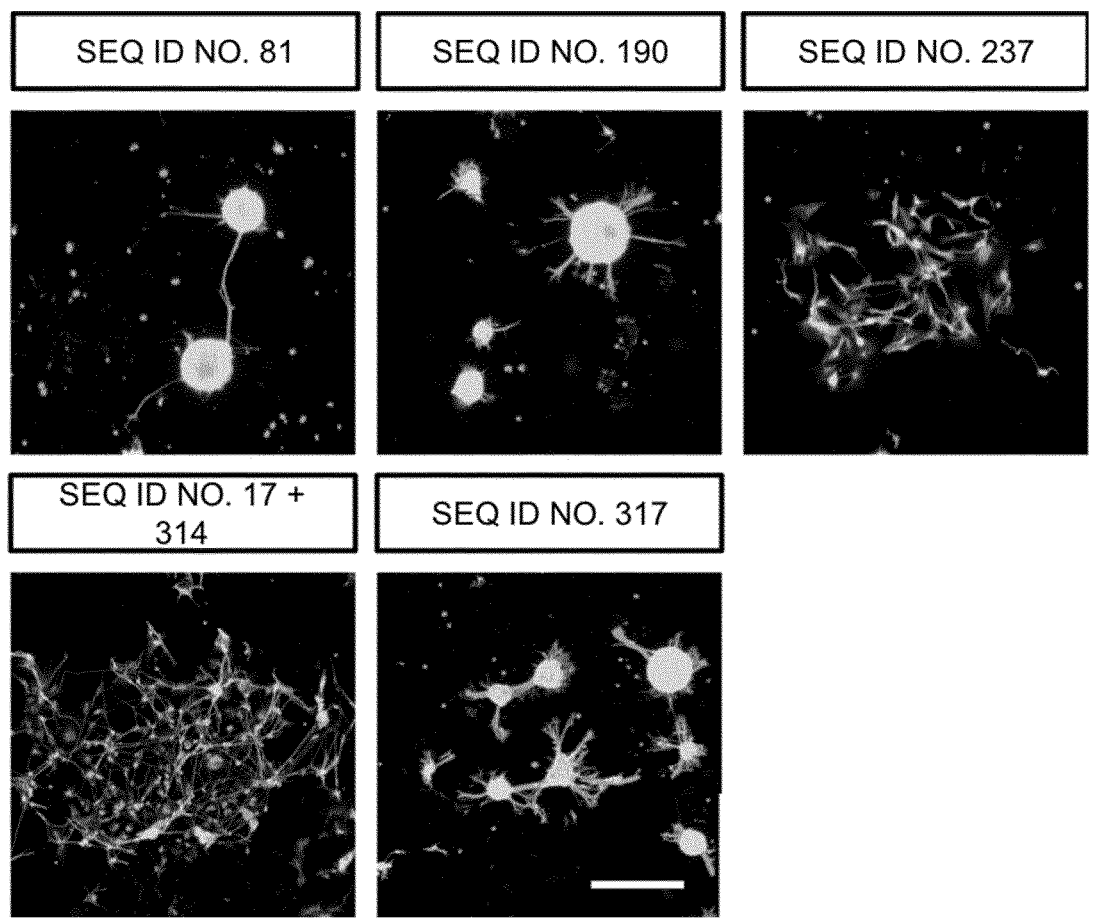
FIG. 16 shows fluorescent images of neural precursor cells (NPC) derived from human induced pluripotent stem cells (iPSC) after 10 days of differentiation into neurons as indicated by immunocytochemistry straining with anti-Tuj1 antibody. NPCs have been first expanded on biomatrix layers made of a mixture of 5 μM dermatan sulfate with 5 μM of peptide-polyethylene glycol-conjugate comprising PEG, $R_1$ and KA7 comprising a single or two different peptide sequences of the peptide library given by table 2. After 2 days of expansion, media was changed to patterning media for 6 days, followed by 4 days in maturation media. Cells were fixed with 4% PFA and stained for anti-Tuj1 antibody as presented with the fluorescent images. The 5 shown images present functional $R_1$ sequences that promoted neuronal outgrowth. Scale bar is 100 μm.

First, NPC were seeded at 25,000 cells/$cm^2$ and cultured in expansion condition. Expansion media was prepared by adding CHIR 99021 (3 μM final conc., Axon MedChem), ascorbic acid (final conc. 200 μM, SigmaAldrich) and Pumorphamine (final conc. 0.5 μM, Santa Cruz) to the base media (DMEM and Neurobasal media (Invitrogen) at ration of 1:1, 1% B27, 0.05% N2, 2% Glutamine and 2% Pen/Strep (all Invitrogen). After 2 days of expansion, media was exchanged with patterning media (base media supplemented with ascorbic acid (final conc. 200 μM), Pumorphamine (final conc. 0.5 μM), GDNF (1 ng/mL, PeproTech), and BDNF (2 ng/mL, PeproTech)) with further media changes every second day. After 6 days, media was exchanged to maturation media (base media supplemented with ascorbic acid (200 μM), TGF-133 (1 ng/mL, PeproTech), DBcAMP (100 μM, Santa Cruz), DAPT (5 μM, Biomol), GDNF (1 ng/mL), and BDNF (2 ng/mL)) with media exchange after 2 days. Cells were fixed with 4% PFA and stained with Hoechst33342 (1:4000, Invitrogen), mouse anti-beta3 tubulin/Tuj1 primary antibody (1:400, R and D systems) and anti-mouse secondary antibody with AF488 fluorescent label (1:500, Dianova). Images were acquired using a BioTek Lionheart FX automated microscope (10× objective) with the Gen5 software (version 3.03). Results indicate development of neuronal cells on biomatrix layer comprising peptide sequences with the ID NO. 81, 190, 237, 317, and a mixture of 17 and 314 at 1:1 ratio. Results are shown in FIG. 16.

The invention claimed is:

1. A biomatrix layer having a thickness of 3 nm to 40 μm, comprising:
    a negatively charged polymer (NCP) at a concentration in the range of 0.1 μM to 250 μM; and
    a peptide-polyethylene glycol-conjugate according to general formula (I):

PEG-CW-spacer-R$_1$-spacer-(BX)$n$    (I);

wherein
        said spacer is absent or is a dipeptide, tripeptide or tetrapeptide, wherein said dipeptide, tripeptide or tetrapeptide consists of glycine, aminopropanoic acid, aminobutyric acid, aminopentanoic acid, aminohexanoic acid, aminoheptanoic acid, aminooctanoic acid and 3-aminoacrylic acid or combinations thereof;
        CW is absent or is a dipeptide consisting of the amino acids cysteine and tryptophan;
        B is lysine or arginine, X is selected from alanine, glycine, serine, threonine, tyrosine, glutamic acid or aspartic acid and n is an integer selected from 5, 6, 7, 8, 9, 10, 11, 12, 13, 14, 15, 16, 17, 18, 19 and 20;
        R$_1$ represents a bio-functional peptide, which may be absent or is a peptide comprising 5 to 30 amino acids;
        PEG is comprised at a concentration in the range of 0.1 μM to 1,000 μM;
        R$_1$, if present, is comprised at a concentration in the range of 0.1 μM to 4,000 μM;
        (BX)n is comprised at a concentration in the range of 0.4 μM to 4,000 μM.

2. The biomatrix layer according to claim 1, wherein said peptide-polyethylene glycol-conjugate is one of formula (Ia):

PEG-R$_1$-(BX)$n$    (Ia)

wherein B, X and n are as defined in claim 1.

3. The biomatrix layer according to claim 1, wherein said peptide-polyethylene glycol-conjugate is one of formula (Ib):

PEG-(BX)$n$    (Ib)

wherein B, X and n are as defined in claim 1.

4. The biomatrix layer according to claim 1, wherein said peptide-polyethylene glycol-conjugate of formula (I) comprises further linker sequences between PEG and R$_1$ and R$_1$ and (BX)n and is a peptide-polyethylene glycol-conjugate according to formula (II):

PEG-CWGG-R$_1$-GG-(BX)$n$    (II)

wherein B, X, n and R$_1$ are as defined in claim 1.

5. The biomatrix layer according to claim 1, wherein said peptide-polyethylene glycol-conjugate of formula (II) comprises a further linker sequence between PEG and (BX)n and is a peptide-polyethylene glycol-conjugate according to formula (IIa):

PEG-CWGG-(BX)$n$    (IIa)

wherein B, X, n and R$_1$ are as defined in claim 1.

6. The biomatrix layer according to claim 1, wherein said peptide-polyethylene glycol-conjugate is a mixture of a peptide-polyethylene glycol-conjugate of formula (I) and a peptide-polyethylene glycol-conjugate of formula (Ia) or a mixture of a peptide-polyethylene glycol-conjugate of formula (II) and a peptide-polyethylene glycol-conjugate of formula (IIa) and/or wherein in said mixture, the proportion of said peptide-polyethylene glycol-conjugate of formula (I) or of formula (II) is in the range of 0.1 to 99.9 mol %.

7. The biomatrix layer according to claim 1, wherein said NCP is selected from the group consisting of heparin, heparan sulfate, chondroitin sulfate, dermatan sulfate, keratan sulfate, dextran sulfate, hyaluronic acid, polystyrene sulfate (PSS), sulfated alginate, sulfated hyaluronic acid, cyclic dextran sulfate, cyclic dextran phosphate and phytic acid.

8. The biomatrix layer according to claim 1, wherein
B is lysine or arginine; and/or
X is alanine or serine; and/or
(BX)n is a peptide selected from the group consisting of the peptides with SEQ ID NOs of table 1: 1 to 14; and/or
$R_1$ is a peptide selected from the group consisting of the peptides with SEQ ID NOs of table 2: 15 to 353.

9. The biomatrix layer according to claim 1, wherein said PEG is a starPEG, which is optionally maleimide-functionalized, carboxylic acid-functionalized, amino-functionalized, azide-functionalized, or alkyne-functionalized.

10. The biomatrix layer according to claim 1, wherein the ratio of the peptide-polyethylene glycol-conjugate of formula (I):NCP or the peptide-polyethylene glycol-conjugate of formula (II): NCP is in the range between 1:100 and 100:1.

11. The biomatrix layer according to claim 1, further comprising cells, organiods, a morphogen or at least one active pharmaceutical ingredient.

12. The biomatrix layer according to claim 1, wherein the thickness, stiffness, porosity and surface coverage by cells of the biomatrix layer is adjustable.

13. The biomatrix layer according to claim 1, wherein the concentration of NCP is from 0.1 µM to 50 µM.

14. The biomatrix layer according to claim 1, wherein said PEG is a 4-arm star PEG, which is optionally maleimide-functionalized, carboxylic acid-functionalized, amino-functionalized, azide-functionalized, or alkyne-functionalized.

15. The biomatrix layer according to claim 1, wherein said PEG is a 4-arm star PEG with a molecular weight in the range of 4 kD to 40 kD, which is optionally maleimide-functionalized, carboxylic acid-functionalized, amino-functionalized, azide-functionalized, or alkyne-functionalized.

* * * * *

SEQUENCE LISTING

```
<160> NUMBER OF SEQ ID NOS: 353

<210> SEQ ID NO 1
<211> LENGTH: 10
<212> TYPE: PRT
<213> ORGANISM: artificial sequence
<220> FEATURE:
<223> OTHER INFORMATION: synthetic peptide

<400> SEQUENCE: 1

Lys Ala Lys Ala Lys Ala Lys Ala Lys Ala
1               5                   10

<210> SEQ ID NO 2
<211> LENGTH: 12
<212> TYPE: PRT
<213> ORGANISM: artificial sequence
<220> FEATURE:
<223> OTHER INFORMATION: synthetic peptide

<400> SEQUENCE: 2

Lys Ala Lys Ala Lys Ala Lys Ala Lys Ala Lys Ala
1               5                   10

<210> SEQ ID NO 3
<211> LENGTH: 14
<212> TYPE: PRT
<213> ORGANISM: artificial sequence
<220> FEATURE:
<223> OTHER INFORMATION: synthetic peptide

<400> SEQUENCE: 3

Lys Ala Lys Ala Lys Ala Lys Ala Lys Ala Lys Ala Lys Ala
1               5                   10

<210> SEQ ID NO 4
<211> LENGTH: 18
```

```
<212> TYPE: PRT
<213> ORGANISM: artificial sequence
<220> FEATURE:
<223> OTHER INFORMATION: synthetic peptide

<400> SEQUENCE: 4

Lys Ala Lys Ala Lys Ala Lys Ala Lys Ala Lys Ala Lys Ala Lys Ala
1               5                   10                  15

Lys Ala

<210> SEQ ID NO 5
<211> LENGTH: 22
<212> TYPE: PRT
<213> ORGANISM: artificial sequence
<220> FEATURE:
<223> OTHER INFORMATION: synthetic peptide

<400> SEQUENCE: 5

Lys Ala Lys Ala Lys Ala Lys Ala Lys Ala Lys Ala Lys Ala Lys Ala
1               5                   10                  15

Lys Ala Lys Ala Lys Ala
            20

<210> SEQ ID NO 6
<211> LENGTH: 10
<212> TYPE: PRT
<213> ORGANISM: artificial sequence
<220> FEATURE:
<223> OTHER INFORMATION: synthetic peptide

<400> SEQUENCE: 6

Lys Ser Lys Ser Lys Ser Lys Ser Lys Ser
1               5                   10

<210> SEQ ID NO 7
<211> LENGTH: 12
<212> TYPE: PRT
<213> ORGANISM: artificial sequence
<220> FEATURE:
<223> OTHER INFORMATION: synthetic peptide

<400> SEQUENCE: 7

Lys Ser Lys Ser Lys Ser Lys Ser Lys Ser Lys Ser
1               5                   10

<210> SEQ ID NO 8
<211> LENGTH: 14
<212> TYPE: PRT
<213> ORGANISM: artificial sequence
<220> FEATURE:
<223> OTHER INFORMATION: synthetic peptide

<400> SEQUENCE: 8

Lys Ser Lys Ser Lys Ser Lys Ser Lys Ser Lys Ser Lys Ser
1               5                   10

<210> SEQ ID NO 9
<211> LENGTH: 10
<212> TYPE: PRT
<213> ORGANISM: artificial sequence
<220> FEATURE:
<223> OTHER INFORMATION: synthetic peptide

<400> SEQUENCE: 9

Arg Ala Arg Ala Arg Ala Arg Ala Arg Ala
1               5                   10
```

<210> SEQ ID NO 10
<211> LENGTH: 12
<212> TYPE: PRT
<213> ORGANISM: artificial sequence
<220> FEATURE:
<223> OTHER INFORMATION: synthetic peptide

<400> SEQUENCE: 10

Arg Ala Arg Ala Arg Ala Arg Ala Arg Ala Arg Ala
1               5                   10

<210> SEQ ID NO 11
<211> LENGTH: 14
<212> TYPE: PRT
<213> ORGANISM: artificial sequence
<220> FEATURE:
<223> OTHER INFORMATION: synthetic peptide

<400> SEQUENCE: 11

Arg Ala Arg Ala Arg Ala Arg Ala Arg Ala Arg Ala Arg Ala
1               5                   10

<210> SEQ ID NO 12
<211> LENGTH: 10
<212> TYPE: PRT
<213> ORGANISM: artificial sequence
<220> FEATURE:
<223> OTHER INFORMATION: synthetic peptide

<400> SEQUENCE: 12

Arg Ser Arg Ser Arg Ser Arg Ser Arg Ser
1               5                   10

<210> SEQ ID NO 13
<211> LENGTH: 12
<212> TYPE: PRT
<213> ORGANISM: artificial sequence
<220> FEATURE:
<223> OTHER INFORMATION: synthetic peptide

<400> SEQUENCE: 13

Arg Ser Arg Ser Arg Ser Arg Ser Arg Ser Arg Ser
1               5                   10

<210> SEQ ID NO 14
<211> LENGTH: 14
<212> TYPE: PRT
<213> ORGANISM: artificial sequence
<220> FEATURE:
<223> OTHER INFORMATION: synthetic peptide

<400> SEQUENCE: 14

Arg Ser Arg Ser Arg Ser Arg Ser Arg Ser Arg Ser Arg Ser
1               5                   10

<210> SEQ ID NO 15
<211> LENGTH: 3
<212> TYPE: PRT
<213> ORGANISM: artificial sequence
<220> FEATURE:
<223> OTHER INFORMATION: synthetic peptide

<400> SEQUENCE: 15

Arg Gly Asp
1

<210> SEQ ID NO 16
<211> LENGTH: 4
<212> TYPE: PRT
<213> ORGANISM: artificial sequence
<220> FEATURE:
<223> OTHER INFORMATION: synthetic peptide

<400> SEQUENCE: 16

Arg Gly Asp Ser
1

<210> SEQ ID NO 17
<211> LENGTH: 5
<212> TYPE: PRT
<213> ORGANISM: artificial sequence
<220> FEATURE:
<223> OTHER INFORMATION: synthetic peptide

<400> SEQUENCE: 17

Arg Gly Asp Ser Pro
1               5

<210> SEQ ID NO 18
<211> LENGTH: 12
<212> TYPE: PRT
<213> ORGANISM: artificial sequence
<220> FEATURE:
<223> OTHER INFORMATION: synthetic peptide

<400> SEQUENCE: 18

Ala Ala Glu Pro Leu Lys Asn Ile Gly Ile Leu Phe
1               5                   10

<210> SEQ ID NO 19
<211> LENGTH: 12
<212> TYPE: PRT
<213> ORGANISM: artificial sequence
<220> FEATURE:
<223> OTHER INFORMATION: synthetic peptide

<400> SEQUENCE: 19

Ala Ala Ser Ile Lys Val Ala Val Ser Ala Asp Arg
1               5                   10

<210> SEQ ID NO 20
<211> LENGTH: 12
<212> TYPE: PRT
<213> ORGANISM: artificial sequence
<220> FEATURE:
<223> OTHER INFORMATION: synthetic peptide

<400> SEQUENCE: 20

Ala Asp Asn Leu Leu Phe Tyr Leu Gly Ser Ala Lys
1               5                   10

<210> SEQ ID NO 21
<211> LENGTH: 6
<212> TYPE: PRT
<213> ORGANISM: artificial sequence
<220> FEATURE:
<223> OTHER INFORMATION: synthetic peptide

<400> SEQUENCE: 21

Ala Asp Thr Pro Pro Val
1               5

```
<210> SEQ ID NO 22
<211> LENGTH: 5
<212> TYPE: PRT
<213> ORGANISM: artificial sequence
<220> FEATURE:
<223> OTHER INFORMATION: synthetic peptide

<400> SEQUENCE: 22

Ala Glu Tyr Leu Arg
1               5

<210> SEQ ID NO 23
<211> LENGTH: 12
<212> TYPE: PRT
<213> ORGANISM: artificial sequence
<220> FEATURE:
<223> OTHER INFORMATION: synthetic peptide

<400> SEQUENCE: 23

Ala Phe Gly Val Leu Ala Leu Trp Gly Thr Arg Val
1               5                   10

<210> SEQ ID NO 24
<211> LENGTH: 12
<212> TYPE: PRT
<213> ORGANISM: artificial sequence
<220> FEATURE:
<223> OTHER INFORMATION: synthetic peptide

<400> SEQUENCE: 24

Ala Phe Ser Thr Leu Glu Gly Arg Pro Ser Ala Tyr
1               5                   10

<210> SEQ ID NO 25
<211> LENGTH: 12
<212> TYPE: PRT
<213> ORGANISM: artificial sequence
<220> FEATURE:
<223> OTHER INFORMATION: synthetic peptide

<400> SEQUENCE: 25

Ala Gly Gln Trp His Arg Val Ser Val Arg Trp Gly
1               5                   10

<210> SEQ ID NO 26
<211> LENGTH: 13
<212> TYPE: PRT
<213> ORGANISM: artificial sequence
<220> FEATURE:
<223> OTHER INFORMATION: synthetic peptide

<400> SEQUENCE: 26

Ala Gly Thr Phe Ala Leu Arg Gly Asp Asn Pro Gln Gly
1               5                   10

<210> SEQ ID NO 27
<211> LENGTH: 15
<212> TYPE: PRT
<213> ORGANISM: artificial sequence
<220> FEATURE:
<223> OTHER INFORMATION: synthetic peptide

<400> SEQUENCE: 27

Ala Ile Ser Met Leu Tyr Leu Asp Glu Asn Glu Lys Val Val Leu
1               5                   10                  15

<210> SEQ ID NO 28
```

```
<211> LENGTH: 13
<212> TYPE: PRT
<213> ORGANISM: artificial sequence
<220> FEATURE:
<223> OTHER INFORMATION: synthetic peptide

<400> SEQUENCE: 28

Ala Lys Ala Leu Glu Leu Arg Gly Val Gln Pro Val Ser
1               5                   10

<210> SEQ ID NO 29
<211> LENGTH: 12
<212> TYPE: PRT
<213> ORGANISM: artificial sequence
<220> FEATURE:
<223> OTHER INFORMATION: synthetic peptide

<400> SEQUENCE: 29

Ala Lys Lys Ile Lys Asn Arg Leu Glu Leu Val Val
1               5                   10

<210> SEQ ID NO 30
<211> LENGTH: 6
<212> TYPE: PRT
<213> ORGANISM: artificial sequence
<220> FEATURE:
<223> OTHER INFORMATION: synthetic peptide

<400> SEQUENCE: 30

Ala Leu Arg Gly Asp Asn
1               5

<210> SEQ ID NO 31
<211> LENGTH: 12
<212> TYPE: PRT
<213> ORGANISM: artificial sequence
<220> FEATURE:
<223> OTHER INFORMATION: synthetic peptide

<400> SEQUENCE: 31

Ala Asn Gly Gln Thr Pro Ile Gln Arg Tyr Ile Lys
1               5                   10

<210> SEQ ID NO 32
<211> LENGTH: 16
<212> TYPE: PRT
<213> ORGANISM: artificial sequence
<220> FEATURE:
<223> OTHER INFORMATION: synthetic peptide

<400> SEQUENCE: 32

Ala Asn Arg Tyr Leu Ala Met Lys Glu Asp Gly Arg Leu Leu Ala Ser
1               5                   10                  15

<210> SEQ ID NO 33
<211> LENGTH: 12
<212> TYPE: PRT
<213> ORGANISM: artificial sequence
<220> FEATURE:
<223> OTHER INFORMATION: synthetic peptide

<400> SEQUENCE: 33

Ala Asn Val Thr His Leu Leu Ile Arg Ala Asn Tyr
1               5                   10

<210> SEQ ID NO 34
<211> LENGTH: 13
```

```
<212> TYPE: PRT
<213> ORGANISM: artificial sequence
<220> FEATURE:
<223> OTHER INFORMATION: synthetic peptide

<400> SEQUENCE: 34

Ala Pro Met Ser Gly Arg Ser Pro Ser Leu Val Leu Lys
1               5                   10

<210> SEQ ID NO 35
<211> LENGTH: 13
<212> TYPE: PRT
<213> ORGANISM: artificial sequence
<220> FEATURE:
<223> OTHER INFORMATION: synthetic peptide

<400> SEQUENCE: 35

Ala Pro Val Lys Phe Leu Gly Asn Gln Val Leu Ser Tyr
1               5                   10

<210> SEQ ID NO 36
<211> LENGTH: 12
<212> TYPE: PRT
<213> ORGANISM: artificial sequence
<220> FEATURE:
<223> OTHER INFORMATION: synthetic peptide

<400> SEQUENCE: 36

Ala Pro Val Asn Val Thr Ala Ser Val Gln Ile Gln
1               5                   10

<210> SEQ ID NO 37
<211> LENGTH: 11
<212> TYPE: PRT
<213> ORGANISM: artificial sequence
<220> FEATURE:
<223> OTHER INFORMATION: synthetic peptide

<400> SEQUENCE: 37

Ala Ser Lys Ala Ile Gln Val Phe Leu Leu Ala
1               5                   10

<210> SEQ ID NO 38
<211> LENGTH: 12
<212> TYPE: PRT
<213> ORGANISM: artificial sequence
<220> FEATURE:
<223> OTHER INFORMATION: synthetic peptide

<400> SEQUENCE: 38

Ala Ser Lys Ala Ile Gln Val Phe Leu Leu Ala Gly
1               5                   10

<210> SEQ ID NO 39
<211> LENGTH: 12
<212> TYPE: PRT
<213> ORGANISM: artificial sequence
<220> FEATURE:
<223> OTHER INFORMATION: synthetic peptide

<400> SEQUENCE: 39

Ala Ser Lys Ala Ile Gln Val Phe Leu Leu Gly Gly
1               5                   10

<210> SEQ ID NO 40
<211> LENGTH: 9
<212> TYPE: PRT
```

```
-continued

<213> ORGANISM: artificial sequence
<220> FEATURE:
<223> OTHER INFORMATION: synthetic peptide

<400> SEQUENCE: 40

Ala Thr Glu Thr Thr Ile Thr Ile Ser
1               5

<210> SEQ ID NO 41
<211> LENGTH: 20
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (13)..(13)
<223> OTHER INFORMATION: Xaa can be any naturally occurring amino acid

<400> SEQUENCE: 41

Ala Thr Leu Gln Leu Gln Glu Gly Arg Leu His Phe Xaa Phe Asp Leu
1               5                   10                  15

Gly Lys Gly Arg
            20

<210> SEQ ID NO 42
<211> LENGTH: 12
<212> TYPE: PRT
<213> ORGANISM: artificial sequence
<220> FEATURE:
<223> OTHER INFORMATION: synthetic peptide

<400> SEQUENCE: 42

Ala Tyr Phe Ser Ile Val Lys Ile Glu Arg Val Gly
1               5                   10

<210> SEQ ID NO 43
<211> LENGTH: 9
<212> TYPE: PRT
<213> ORGANISM: artificial sequence
<220> FEATURE:
<223> OTHER INFORMATION: synthetic peptide

<400> SEQUENCE: 43

Cys Asp Pro Gly Tyr Ile Gly Ser Arg
1               5

<210> SEQ ID NO 44
<211> LENGTH: 19
<212> TYPE: PRT
<213> ORGANISM: artificial sequence
<220> FEATURE:
<223> OTHER INFORMATION: synthetic peptide

<400> SEQUENCE: 44

Cys Asn Tyr Tyr Ser Asn Ser Tyr Ser Phe Trp Leu Ala Ser Leu Asn
1               5                   10                  15

Pro Glu Arg

<210> SEQ ID NO 45
<211> LENGTH: 17
<212> TYPE: PRT
<213> ORGANISM: artificial sequence
<220> FEATURE:
<223> OTHER INFORMATION: synthetic peptide
```

```
<400> SEQUENCE: 45

Cys Ser Arg Asn Leu Ser Glu Ile Lys Leu Leu Ile Ser Arg Ala Arg
1               5                   10                  15

Lys

<210> SEQ ID NO 46
<211> LENGTH: 17
<212> TYPE: PRT
<213> ORGANISM: artificial sequence
<220> FEATURE:
<223> OTHER INFORMATION: synthetic peptide

<400> SEQUENCE: 46

Cys Thr Asp Ile Lys Gly Lys Cys Thr Gly Ala Cys Asp Gly Lys Gln
1               5                   10                  15

Cys

<210> SEQ ID NO 47
<211> LENGTH: 19
<212> TYPE: PRT
<213> ORGANISM: artificial sequence
<220> FEATURE:
<223> OTHER INFORMATION: synthetic peptide

<400> SEQUENCE: 47

Asp Phe Gly Thr Val Gln Leu Arg Asn Gly Phe Pro Phe Phe Ser Tyr
1               5                   10                  15

Asp Leu Gly

<210> SEQ ID NO 48
<211> LENGTH: 19
<212> TYPE: PRT
<213> ORGANISM: artificial sequence
<220> FEATURE:
<223> OTHER INFORMATION: synthetic peptide

<400> SEQUENCE: 48

Asp Phe Met Thr Leu Phe Leu Ala His Gly Arg Leu Val Phe Met Phe
1               5                   10                  15

Asn Val Gly

<210> SEQ ID NO 49
<211> LENGTH: 4
<212> TYPE: PRT
<213> ORGANISM: artificial sequence
<220> FEATURE:
<223> OTHER INFORMATION: synthetic peptide

<400> SEQUENCE: 49

Asp Gly Glu Ala
1

<210> SEQ ID NO 50
<211> LENGTH: 12
<212> TYPE: PRT
<213> ORGANISM: artificial sequence
<220> FEATURE:
<223> OTHER INFORMATION: synthetic peptide

<400> SEQUENCE: 50

Asp Gly Gln Trp His Ser Val Thr Val Ser Ile Lys
1               5                   10
```

```
<210> SEQ ID NO 51
<211> LENGTH: 10
<212> TYPE: PRT
<213> ORGANISM: artificial sequence
<220> FEATURE:
<223> OTHER INFORMATION: synthetic peptide

<400> SEQUENCE: 51

Asp Gly Arg Gly Asp Ser Val Ala Tyr Gly
1               5                   10

<210> SEQ ID NO 52
<211> LENGTH: 12
<212> TYPE: PRT
<213> ORGANISM: artificial sequence
<220> FEATURE:
<223> OTHER INFORMATION: synthetic peptide

<400> SEQUENCE: 52

Asp Gly Arg Trp His Arg Val Ala Val Ile Met Gly
1               5                   10

<210> SEQ ID NO 53
<211> LENGTH: 6
<212> TYPE: PRT
<213> ORGANISM: artificial sequence
<220> FEATURE:
<223> OTHER INFORMATION: synthetic peptide

<400> SEQUENCE: 53

Asp Pro Glu Thr Gly Val
1               5

<210> SEQ ID NO 54
<211> LENGTH: 8
<212> TYPE: PRT
<213> ORGANISM: artificial sequence
<220> FEATURE:
<223> OTHER INFORMATION: synthetic peptide

<400> SEQUENCE: 54

Asp Pro Gly Tyr Ile Gly Ser Arg
1               5

<210> SEQ ID NO 55
<211> LENGTH: 5
<212> TYPE: PRT
<213> ORGANISM: artificial sequence
<220> FEATURE:
<223> OTHER INFORMATION: synthetic peptide

<400> SEQUENCE: 55

Asp Gln Asn Asp Asn
1               5

<210> SEQ ID NO 56
<211> LENGTH: 18
<212> TYPE: PRT
<213> ORGANISM: artificial sequence
<220> FEATURE:
<223> OTHER INFORMATION: synthetic peptide

<400> SEQUENCE: 56

Asp Arg Glu Gly Cys Arg Arg Gly Trp Val Gly Gln Cys Lys Ala Trp
1               5                   10                  15

Phe Asn
```

<210> SEQ ID NO 57
<211> LENGTH: 10
<212> TYPE: PRT
<213> ORGANISM: artificial sequence
<220> FEATURE:
<223> OTHER INFORMATION: synthetic peptide

<400> SEQUENCE: 57

Asp Arg Val Glu Pro Tyr Ser Ser Thr Ala
1               5                   10

<210> SEQ ID NO 58
<211> LENGTH: 12
<212> TYPE: PRT
<213> ORGANISM: artificial sequence
<220> FEATURE:
<223> OTHER INFORMATION: synthetic peptide

<400> SEQUENCE: 58

Asp Ser Ile Thr Lys Tyr Phe Gln Met Ser Leu Glu
1               5                   10

<210> SEQ ID NO 59
<211> LENGTH: 12
<212> TYPE: PRT
<213> ORGANISM: artificial sequence
<220> FEATURE:
<223> OTHER INFORMATION: synthetic peptide

<400> SEQUENCE: 59

Asp Ser Ile Thr Lys Tyr Phe Gln Met Ser Leu Glu
1               5                   10

<210> SEQ ID NO 60
<211> LENGTH: 13
<212> TYPE: PRT
<213> ORGANISM: artificial sequence
<220> FEATURE:
<223> OTHER INFORMATION: synthetic peptide

<400> SEQUENCE: 60

Asp Thr Ile Asn Asn Gly Arg Asp His Met Ile Leu Ile
1               5                   10

<210> SEQ ID NO 61
<211> LENGTH: 15
<212> TYPE: PRT
<213> ORGANISM: artificial sequence
<220> FEATURE:
<223> OTHER INFORMATION: synthetic peptide

<400> SEQUENCE: 61

Asp Val Asp Val Pro Asp Gly Arg Gly Asp Ser Leu Ala Tyr Gly
1               5                   10                  15

<210> SEQ ID NO 62
<211> LENGTH: 12
<212> TYPE: PRT
<213> ORGANISM: artificial sequence
<220> FEATURE:
<223> OTHER INFORMATION: synthetic peptide

<400> SEQUENCE: 62

Asp Val Ile Ser Leu Tyr Asn Phe Lys His Ile Tyr
1               5                   10

<210> SEQ ID NO 63
<211> LENGTH: 10
<212> TYPE: PRT
<213> ORGANISM: artificial sequence
<220> FEATURE:
<223> OTHER INFORMATION: synthetic peptide

<400> SEQUENCE: 63

Asp Val Arg Arg Gly Ile Lys Lys Thr Asp
1               5                   10

<210> SEQ ID NO 64
<211> LENGTH: 5
<212> TYPE: PRT
<213> ORGANISM: artificial sequence
<220> FEATURE:
<223> OTHER INFORMATION: synthetic peptide

<400> SEQUENCE: 64

Asp Trp Ile Val Ala
1               5

<210> SEQ ID NO 65
<211> LENGTH: 19
<212> TYPE: PRT
<213> ORGANISM: artificial sequence
<220> FEATURE:
<223> OTHER INFORMATION: synthetic peptide

<400> SEQUENCE: 65

Asp Tyr Ala Thr Leu Gln Leu Gln Glu Gly Arg Leu His Phe Met Phe
1               5                   10                  15

Asp Leu Gly

<210> SEQ ID NO 66
<211> LENGTH: 7
<212> TYPE: PRT
<213> ORGANISM: artificial sequence
<220> FEATURE:
<223> OTHER INFORMATION: synthetic peptide

<400> SEQUENCE: 66

Glu Asp Gly Ile His Glu Leu
1               5

<210> SEQ ID NO 67
<211> LENGTH: 7
<212> TYPE: PRT
<213> ORGANISM: artificial sequence
<220> FEATURE:
<223> OTHER INFORMATION: synthetic peptide

<400> SEQUENCE: 67

Glu Ile Lys Leu Leu Ile Ser
1               5

<210> SEQ ID NO 68
<211> LENGTH: 8
<212> TYPE: PRT
<213> ORGANISM: artificial sequence
<220> FEATURE:
<223> OTHER INFORMATION: synthetic peptide

<400> SEQUENCE: 68

Glu Ile Leu Asp Val Pro Ser Thr
1               5

```
<210> SEQ ID NO 69
<211> LENGTH: 3
<212> TYPE: PRT
<213> ORGANISM: artificial sequence
<220> FEATURE:
<223> OTHER INFORMATION: synthetic peptide

<400> SEQUENCE: 69

Glu Leu Arg
1

<210> SEQ ID NO 70
<211> LENGTH: 10
<212> TYPE: PRT
<213> ORGANISM: artificial sequence
<220> FEATURE:
<223> OTHER INFORMATION: synthetic peptide

<400> SEQUENCE: 70

Glu Arg Gly Val Val Ser Ile Lys Gly Val
1               5                   10

<210> SEQ ID NO 71
<211> LENGTH: 7
<212> TYPE: PRT
<213> ORGANISM: artificial sequence
<220> FEATURE:
<223> OTHER INFORMATION: synthetic peptide

<400> SEQUENCE: 71

Glu Thr Ile Thr Gly Phe Gly
1               5

<210> SEQ ID NO 72
<211> LENGTH: 13
<212> TYPE: PRT
<213> ORGANISM: artificial sequence
<220> FEATURE:
<223> OTHER INFORMATION: synthetic peptide

<400> SEQUENCE: 72

Glu Val Asn Val Thr Leu Asp Leu Gly Gln Val Phe His
1               5                   10

<210> SEQ ID NO 73
<211> LENGTH: 15
<212> TYPE: PRT
<213> ORGANISM: artificial sequence
<220> FEATURE:
<223> OTHER INFORMATION: synthetic peptide

<400> SEQUENCE: 73

Glu Val Tyr Val Val Ala Glu Asn Gln Gln Gly Lys Ser Lys Ala
1               5                   10                  15

<210> SEQ ID NO 74
<211> LENGTH: 11
<212> TYPE: PRT
<213> ORGANISM: artificial sequence
<220> FEATURE:
<223> OTHER INFORMATION: synthetic peptide

<400> SEQUENCE: 74

Phe Ala Leu Trp Asp Ala Ile Ile Gly Glu Leu
1               5                   10
```

```
<210> SEQ ID NO 75
<211> LENGTH: 11
<212> TYPE: PRT
<213> ORGANISM: artificial sequence
<220> FEATURE:
<223> OTHER INFORMATION: synthetic peptide

<400> SEQUENCE: 75

Phe Asp Leu His Gln Asn Met Gly Ser Val Asn
1               5                   10

<210> SEQ ID NO 76
<211> LENGTH: 14
<212> TYPE: PRT
<213> ORGANISM: artificial sequence
<220> FEATURE:
<223> OTHER INFORMATION: synthetic peptide

<400> SEQUENCE: 76

Phe Asp Pro Glu Leu Tyr Arg Ser Thr Gly His Gly Gly His
1               5                   10

<210> SEQ ID NO 77
<211> LENGTH: 12
<212> TYPE: PRT
<213> ORGANISM: artificial sequence
<220> FEATURE:
<223> OTHER INFORMATION: synthetic peptide

<400> SEQUENCE: 77

Phe Phe Asp Gly Ser Ser Tyr Ala Val Val Arg Asp
1               5                   10

<210> SEQ ID NO 78
<211> LENGTH: 7
<212> TYPE: PRT
<213> ORGANISM: artificial sequence
<220> FEATURE:
<223> OTHER INFORMATION: synthetic peptide

<400> SEQUENCE: 78

Phe His Arg Arg Ile Lys Ala
1               5

<210> SEQ ID NO 79
<211> LENGTH: 12
<212> TYPE: PRT
<213> ORGANISM: artificial sequence
<220> FEATURE:
<223> OTHER INFORMATION: synthetic peptide

<400> SEQUENCE: 79

Phe Gln Lys Leu Leu Asn Asn Leu Thr Ser Ile Lys
1               5                   10

<210> SEQ ID NO 80
<211> LENGTH: 9
<212> TYPE: PRT
<213> ORGANISM: artificial sequence
<220> FEATURE:
<223> OTHER INFORMATION: synthetic peptide

<400> SEQUENCE: 80

Phe Arg His Arg Asn Arg Lys Gly Tyr
1               5
```

```
<210> SEQ ID NO 81
<211> LENGTH: 7
<212> TYPE: PRT
<213> ORGANISM: artificial sequence
<220> FEATURE:
<223> OTHER INFORMATION: synthetic peptide

<400> SEQUENCE: 81

Phe Arg Leu Val Phe Arg Tyr
1               5

<210> SEQ ID NO 82
<211> LENGTH: 12
<212> TYPE: PRT
<213> ORGANISM: artificial sequence
<220> FEATURE:
<223> OTHER INFORMATION: synthetic peptide

<400> SEQUENCE: 82

Phe Ser Thr Arg Asn Glu Ser Gly Ile Ile Leu Leu
1               5                   10

<210> SEQ ID NO 83
<211> LENGTH: 12
<212> TYPE: PRT
<213> ORGANISM: artificial sequence
<220> FEATURE:
<223> OTHER INFORMATION: synthetic peptide

<400> SEQUENCE: 83

Phe Val Leu Tyr Leu Gly Ser Lys Asn Ala Lys Lys
1               5                   10

<210> SEQ ID NO 84
<211> LENGTH: 6
<212> TYPE: PRT
<213> ORGANISM: artificial sequence
<220> FEATURE:
<223> OTHER INFORMATION: synthetic peptide

<400> SEQUENCE: 84

Phe Tyr Phe Asp Leu Arg
1               5

<210> SEQ ID NO 85
<211> LENGTH: 12
<212> TYPE: PRT
<213> ORGANISM: artificial sequence
<220> FEATURE:
<223> OTHER INFORMATION: synthetic peptide

<400> SEQUENCE: 85

Gly Ala Ala Trp Lys Ile Lys Gly Pro Ile Tyr Leu
1               5                   10

<210> SEQ ID NO 86
<211> LENGTH: 12
<212> TYPE: PRT
<213> ORGANISM: artificial sequence
<220> FEATURE:
<223> OTHER INFORMATION: synthetic peptide

<400> SEQUENCE: 86

Gly Ala Lys Gly Arg Ala Gly Phe Pro Gly Leu Pro
1               5                   10

<210> SEQ ID NO 87
```

```
<211> LENGTH: 6
<212> TYPE: PRT
<213> ORGANISM: artificial sequence
<220> FEATURE:
<223> OTHER INFORMATION: synthetic peptide

<400> SEQUENCE: 87

Gly Ala Pro Gly Glu Arg
1               5

<210> SEQ ID NO 88
<211> LENGTH: 12
<212> TYPE: PRT
<213> ORGANISM: artificial sequence
<220> FEATURE:
<223> OTHER INFORMATION: synthetic peptide

<400> SEQUENCE: 88

Gly Ala Pro Gly Pro Lys Gly Ala Arg Gly Ser Ala
1               5                   10

<210> SEQ ID NO 89
<211> LENGTH: 6
<212> TYPE: PRT
<213> ORGANISM: artificial sequence
<220> FEATURE:
<223> OTHER INFORMATION: synthetic peptide

<400> SEQUENCE: 89

Gly Ala Ser Gly Glu Arg
1               5

<210> SEQ ID NO 90
<211> LENGTH: 15
<212> TYPE: PRT
<213> ORGANISM: artificial sequence
<220> FEATURE:
<223> OTHER INFORMATION: synthetic peptide

<400> SEQUENCE: 90

Gly Asp Leu Gly Arg Pro Gly Arg Lys Gly Arg Pro Gly Pro Pro
1               5                   10                  15

<210> SEQ ID NO 91
<211> LENGTH: 13
<212> TYPE: PRT
<213> ORGANISM: artificial sequence
<220> FEATURE:
<223> OTHER INFORMATION: synthetic peptide

<400> SEQUENCE: 91

Gly Asp Arg Gly Ile Lys Gly His Arg Gly Phe Ser Gly
1               5                   10

<210> SEQ ID NO 92
<211> LENGTH: 13
<212> TYPE: PRT
<213> ORGANISM: artificial sequence
<220> FEATURE:
<223> OTHER INFORMATION: synthetic peptide

<400> SEQUENCE: 92

Gly Glu Phe Tyr Phe Asp Leu Arg Leu Lys Gly Asp Lys
1               5                   10

<210> SEQ ID NO 93
<211> LENGTH: 6
```

```
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: pyrrolysine

<400> SEQUENCE: 93

Gly Phe Xaa Gly Glu Arg
1               5

<210> SEQ ID NO 94
<211> LENGTH: 6
<212> TYPE: PRT
<213> ORGANISM: artificial sequence
<220> FEATURE:
<223> OTHER INFORMATION: synthetic peptide

<400> SEQUENCE: 94

Gly Phe Pro Gly Glu Arg
1               5

<210> SEQ ID NO 95
<211> LENGTH: 14
<212> TYPE: PRT
<213> ORGANISM: artificial sequence
<220> FEATURE:
<223> OTHER INFORMATION: synthetic peptide

<400> SEQUENCE: 95

Gly Phe Pro Gly Gly Leu Asn Gln Phe Gly Leu Thr Thr Asn
1               5                   10

<210> SEQ ID NO 96
<211> LENGTH: 12
<212> TYPE: PRT
<213> ORGANISM: artificial sequence
<220> FEATURE:
<223> OTHER INFORMATION: synthetic peptide

<400> SEQUENCE: 96

Gly Phe Pro Gly Ser Arg Gly Asp Thr Gly Pro Pro
1               5                   10

<210> SEQ ID NO 97
<211> LENGTH: 12
<212> TYPE: PRT
<213> ORGANISM: artificial sequence
<220> FEATURE:
<223> OTHER INFORMATION: synthetic peptide

<400> SEQUENCE: 97

Gly Gly Phe Leu Lys Tyr Thr Val Ser Tyr Asp Ile
1               5                   10

<210> SEQ ID NO 98
<211> LENGTH: 20
<212> TYPE: PRT
<213> ORGANISM: artificial sequence
<220> FEATURE:
<223> OTHER INFORMATION: synthetic peptide

<400> SEQUENCE: 98

Gly Gly Thr Tyr Ser Cys His Phe Gly Pro Leu Thr Trp Val Cys Lys
1               5                   10                  15
```

```
Pro Gln Gly Gly
        20

<210> SEQ ID NO 99
<211> LENGTH: 9
<212> TYPE: PRT
<213> ORGANISM: artificial sequence
<220> FEATURE:
<223> OTHER INFORMATION: synthetic peptide

<400> SEQUENCE: 99

Gly Gly Trp Gly Arg Gly Asp Ser Pro
1               5

<210> SEQ ID NO 100
<211> LENGTH: 21
<212> TYPE: PRT
<213> ORGANISM: artificial sequence
<220> FEATURE:
<223> OTHER INFORMATION: synthetic peptide

<400> SEQUENCE: 100

Gly His Arg Gly Pro Thr Gly Arg Pro Gly Lys Arg Gly Lys Gln Gly
1               5                   10                  15

Gln Lys Gly Asp Ser
        20

<210> SEQ ID NO 101
<211> LENGTH: 6
<212> TYPE: PRT
<213> ORGANISM: artificial sequence
<220> FEATURE:
<223> OTHER INFORMATION: synthetic peptide

<400> SEQUENCE: 101

Gly Ile Ile Phe Phe Leu
1               5

<210> SEQ ID NO 102
<211> LENGTH: 6
<212> TYPE: PRT
<213> ORGANISM: artificial sequence
<220> FEATURE:
<223> OTHER INFORMATION: synthetic peptide

<400> SEQUENCE: 102

Gly Lys Asp Gly Glu Ser
1               5

<210> SEQ ID NO 103
<211> LENGTH: 12
<212> TYPE: PRT
<213> ORGANISM: artificial sequence
<220> FEATURE:
<223> OTHER INFORMATION: synthetic peptide

<400> SEQUENCE: 103

Gly Lys Asn Thr Gly Asp His Phe Val Leu Tyr Met
1               5                   10

<210> SEQ ID NO 104
<211> LENGTH: 6
<212> TYPE: PRT
<213> ORGANISM: artificial sequence
<220> FEATURE:
<223> OTHER INFORMATION: synthetic peptide
```

<400> SEQUENCE: 104

Gly Lys Arg Gly Lys Pro
1               5

<210> SEQ ID NO 105
<211> LENGTH: 10
<212> TYPE: PRT
<213> ORGANISM: artificial sequence
<220> FEATURE:
<223> OTHER INFORMATION: synthetic peptide

<400> SEQUENCE: 105

Gly Leu Asp Arg Glu Ser Tyr Pro Tyr Tyr
1               5                   10

<210> SEQ ID NO 106
<211> LENGTH: 12
<212> TYPE: PRT
<213> ORGANISM: artificial sequence
<220> FEATURE:
<223> OTHER INFORMATION: synthetic peptide

<400> SEQUENCE: 106

Gly Leu Ile Tyr Tyr Val Ala His Gln Asn Gln Met
1               5                   10

<210> SEQ ID NO 107
<211> LENGTH: 6
<212> TYPE: PRT
<213> ORGANISM: artificial sequence
<220> FEATURE:
<223> OTHER INFORMATION: synthetic peptide

<400> SEQUENCE: 107

Gly Leu Lys Gly Glu Asn
1               5

<210> SEQ ID NO 108
<211> LENGTH: 12
<212> TYPE: PRT
<213> ORGANISM: artificial sequence
<220> FEATURE:
<223> OTHER INFORMATION: synthetic peptide

<400> SEQUENCE: 108

Gly Leu Leu Phe Tyr Met Ala Arg Ile Asn His Ala
1               5                   10

<210> SEQ ID NO 109
<211> LENGTH: 6
<212> TYPE: PRT
<213> ORGANISM: artificial sequence
<220> FEATURE:
<223> OTHER INFORMATION: synthetic peptide

<400> SEQUENCE: 109

Gly Leu Pro Gly Glu Asn
1               5

<210> SEQ ID NO 110
<211> LENGTH: 6
<212> TYPE: PRT
<213> ORGANISM: artificial sequence
<220> FEATURE:
<223> OTHER INFORMATION: synthetic peptide

```
<400> SEQUENCE: 110

Gly Leu Pro Gly Glu Arg
1               5

<210> SEQ ID NO 111
<211> LENGTH: 6
<212> TYPE: PRT
<213> ORGANISM: artificial sequence
<220> FEATURE:
<223> OTHER INFORMATION: synthetic peptide

<400> SEQUENCE: 111

Gly Leu Ser Gly Glu Arg
1               5

<210> SEQ ID NO 112
<211> LENGTH: 6
<212> TYPE: PRT
<213> ORGANISM: artificial sequence
<220> FEATURE:
<223> OTHER INFORMATION: synthetic peptide

<400> SEQUENCE: 112

Gly Met Pro Gly Glu Arg
1               5

<210> SEQ ID NO 113
<211> LENGTH: 13
<212> TYPE: PRT
<213> ORGANISM: artificial sequence
<220> FEATURE:
<223> OTHER INFORMATION: synthetic peptide

<400> SEQUENCE: 113

Gly Pro Ala Gly Lys Asp Gly Glu Ala Gly Ala Gln Gly
1               5                   10

<210> SEQ ID NO 114
<211> LENGTH: 12
<212> TYPE: PRT
<213> ORGANISM: artificial sequence
<220> FEATURE:
<223> OTHER INFORMATION: synthetic peptide

<400> SEQUENCE: 114

Gly Pro Gly Val Val Val Val Glu Arg Gln Tyr Ile
1               5                   10

<210> SEQ ID NO 115
<211> LENGTH: 12
<212> TYPE: PRT
<213> ORGANISM: artificial sequence
<220> FEATURE:
<223> OTHER INFORMATION: synthetic peptide

<400> SEQUENCE: 115

Gly Pro Lys Gly Ala Ala Gly Glu Pro Gly Lys Pro
1               5                   10

<210> SEQ ID NO 116
<211> LENGTH: 12
<212> TYPE: PRT
<213> ORGANISM: artificial sequence
<220> FEATURE:
<223> OTHER INFORMATION: synthetic peptide
```

```
<400> SEQUENCE: 116

Gly Pro Leu Pro Ser Tyr Leu Gln Phe Val Gly Ile
1               5                   10

<210> SEQ ID NO 117
<211> LENGTH: 12
<212> TYPE: PRT
<213> ORGANISM: artificial sequence
<220> FEATURE:
<223> OTHER INFORMATION: synthetic peptide

<400> SEQUENCE: 117

Gly Pro Pro Gly Asp Gln Gly Pro Pro Gly Ile Pro
1               5                   10

<210> SEQ ID NO 118
<211> LENGTH: 15
<212> TYPE: PRT
<213> ORGANISM: artificial sequence
<220> FEATURE:
<223> OTHER INFORMATION: synthetic peptide

<400> SEQUENCE: 118

Gly Pro Gln Gly Ile Ala Gly Gln Arg Gly Val Val Gly Leu Pro
1               5                   10                  15

<210> SEQ ID NO 119
<211> LENGTH: 13
<212> TYPE: PRT
<213> ORGANISM: artificial sequence
<220> FEATURE:
<223> OTHER INFORMATION: synthetic peptide

<400> SEQUENCE: 119

Gly Gln Leu Phe His Val Ala Tyr Ile Leu Ile Lys Phe
1               5                   10

<210> SEQ ID NO 120
<211> LENGTH: 6
<212> TYPE: PRT
<213> ORGANISM: artificial sequence
<220> FEATURE:
<223> OTHER INFORMATION: synthetic peptide

<400> SEQUENCE: 120

Gly Gln Arg Gly Glu Arg
1               5

<210> SEQ ID NO 121
<211> LENGTH: 13
<212> TYPE: PRT
<213> ORGANISM: artificial sequence
<220> FEATURE:
<223> OTHER INFORMATION: synthetic peptide

<400> SEQUENCE: 121

Gly Gln Val Phe His Val Ala Tyr Val Leu Ile Lys Phe
1               5                   10

<210> SEQ ID NO 122
<211> LENGTH: 6
<212> TYPE: PRT
<213> ORGANISM: artificial sequence
<220> FEATURE:
<223> OTHER INFORMATION: synthetic peptide
```

```
<400> SEQUENCE: 122

Gly Arg Arg Gly Lys Thr
1               5

<210> SEQ ID NO 123
<211> LENGTH: 12
<212> TYPE: PRT
<213> ORGANISM: artificial sequence
<220> FEATURE:
<223> OTHER INFORMATION: synthetic peptide

<400> SEQUENCE: 123

Gly Ser Ala Lys Phe Ile Asp Phe Leu Ala Ile Glu
1               5                   10

<210> SEQ ID NO 124
<211> LENGTH: 11
<212> TYPE: PRT
<213> ORGANISM: artificial sequence
<220> FEATURE:
<223> OTHER INFORMATION: synthetic peptide

<400> SEQUENCE: 124

Gly Ser Ile Lys Val Ala Val Trp Gly Gly Cys
1               5                   10

<210> SEQ ID NO 125
<211> LENGTH: 12
<212> TYPE: PRT
<213> ORGANISM: artificial sequence
<220> FEATURE:
<223> OTHER INFORMATION: synthetic peptide

<400> SEQUENCE: 125

Gly Ser Leu Ser Ser His Leu Glu Phe Val Gly Ile
1               5                   10

<210> SEQ ID NO 126
<211> LENGTH: 13
<212> TYPE: PRT
<213> ORGANISM: artificial sequence
<220> FEATURE:
<223> OTHER INFORMATION: synthetic peptide

<400> SEQUENCE: 126

Gly Thr Asn Asn Trp Trp Gln Ser Pro Ser Ile Gln Asn
1               5                   10

<210> SEQ ID NO 127
<211> LENGTH: 15
<212> TYPE: PRT
<213> ORGANISM: artificial sequence
<220> FEATURE:
<223> OTHER INFORMATION: synthetic peptide

<400> SEQUENCE: 127

Gly Thr Pro Gly Pro Gln Gly Ile Ala Gly Gln Arg Asp Val Val
1               5                   10                  15

<210> SEQ ID NO 128
<211> LENGTH: 15
<212> TYPE: PRT
<213> ORGANISM: artificial sequence
<220> FEATURE:
<223> OTHER INFORMATION: synthetic peptide
```

-continued

```
<400> SEQUENCE: 128

Gly Val Lys Gly Asp Lys Gly Asn Pro Gly Trp Pro Gly Ala Pro
1               5                   10                  15

<210> SEQ ID NO 129
<211> LENGTH: 13
<212> TYPE: PRT
<213> ORGANISM: artificial sequence
<220> FEATURE:
<223> OTHER INFORMATION: synthetic peptide

<400> SEQUENCE: 129

Gly Val Tyr Tyr Gln Gly Gly Thr Tyr Ser Lys Ala Ser
1               5                   10

<210> SEQ ID NO 130
<211> LENGTH: 9
<212> TYPE: PRT
<213> ORGANISM: artificial sequence
<220> FEATURE:
<223> OTHER INFORMATION: synthetic peptide

<400> SEQUENCE: 130

Gly Tyr Ile Gly Ser Arg Gly Gly Cys
1               5

<210> SEQ ID NO 131
<211> LENGTH: 3
<212> TYPE: PRT
<213> ORGANISM: artificial sequence
<220> FEATURE:
<223> OTHER INFORMATION: synthetic peptide

<400> SEQUENCE: 131

His Ala Val
1

<210> SEQ ID NO 132
<211> LENGTH: 7
<212> TYPE: PRT
<213> ORGANISM: artificial sequence
<220> FEATURE:
<223> OTHER INFORMATION: synthetic peptide

<400> SEQUENCE: 132

His His His Arg His Ser Phe
1               5

<210> SEQ ID NO 133
<211> LENGTH: 12
<212> TYPE: PRT
<213> ORGANISM: artificial sequence
<220> FEATURE:
<223> OTHER INFORMATION: synthetic peptide

<400> SEQUENCE: 133

His His Leu Gly Gly Ala Lys Gln Ala Gly Asp Val
1               5                   10

<210> SEQ ID NO 134
<211> LENGTH: 12
<212> TYPE: PRT
<213> ORGANISM: artificial sequence
<220> FEATURE:
<223> OTHER INFORMATION: synthetic peptide
```

<400> SEQUENCE: 134

His Lys Ile Lys Ile Val Arg Val Lys Gln Glu Gly
1               5                   10

<210> SEQ ID NO 135
<211> LENGTH: 12
<212> TYPE: PRT
<213> ORGANISM: artificial sequence
<220> FEATURE:
<223> OTHER INFORMATION: synthetic peptide

<400> SEQUENCE: 135

His Lys Lys Leu Lys Ile Arg Ser Gln Glu Lys Tyr
1               5                   10

<210> SEQ ID NO 136
<211> LENGTH: 12
<212> TYPE: PRT
<213> ORGANISM: artificial sequence
<220> FEATURE:
<223> OTHER INFORMATION: synthetic peptide

<400> SEQUENCE: 136

His Leu Ile Met Thr Phe Lys Thr Phe Arg Pro Ala
1               5                   10

<210> SEQ ID NO 137
<211> LENGTH: 38
<212> TYPE: PRT
<213> ORGANISM: artificial sequence
<220> FEATURE:
<223> OTHER INFORMATION: synthetic peptide

<400> SEQUENCE: 137

His Pro Ile Phe His Arg Gly Glu Phe Ser Val Ala Asp Ser Val Ser
1               5                   10                  15

Val Trp Val Gly Asp Cys Thr Asp Ile Lys Gly Lys Cys Thr Gly Ala
            20                  25                  30

Cys Asp Gly Lys Gln Cys
        35

<210> SEQ ID NO 138
<211> LENGTH: 12
<212> TYPE: PRT
<213> ORGANISM: artificial sequence
<220> FEATURE:
<223> OTHER INFORMATION: synthetic peptide

<400> SEQUENCE: 138

His Gln Asn Met Gly Ser Val Asn Val Ser Val Gly
1               5                   10

<210> SEQ ID NO 139
<211> LENGTH: 13
<212> TYPE: PRT
<213> ORGANISM: artificial sequence
<220> FEATURE:
<223> OTHER INFORMATION: synthetic peptide

<400> SEQUENCE: 139

His Gln Asn Gln Met Asp Tyr Ala Thr Leu Gln Leu Gln
1               5                   10

<210> SEQ ID NO 140

```
<211> LENGTH: 12
<212> TYPE: PRT
<213> ORGANISM: artificial sequence
<220> FEATURE:
<223> OTHER INFORMATION: synthetic peptide

<400> SEQUENCE: 140

His Arg Asp Glu Leu Leu Leu Trp Ala Arg Lys Ile
1               5                   10

<210> SEQ ID NO 141
<211> LENGTH: 6
<212> TYPE: PRT
<213> ORGANISM: artificial sequence
<220> FEATURE:
<223> OTHER INFORMATION: synthetic peptide

<400> SEQUENCE: 141

Ile Ala Phe Gln Arg Asn
1               5

<210> SEQ ID NO 142
<211> LENGTH: 5
<212> TYPE: PRT
<213> ORGANISM: artificial sequence
<220> FEATURE:
<223> OTHER INFORMATION: synthetic peptide

<400> SEQUENCE: 142

Ile Asp Ala Pro Ser
1               5

<210> SEQ ID NO 143
<211> LENGTH: 12
<212> TYPE: PRT
<213> ORGANISM: artificial sequence
<220> FEATURE:
<223> OTHER INFORMATION: synthetic peptide

<400> SEQUENCE: 143

Ile Glu Asn Val Val Thr Thr Phe Ala Pro Asn Arg
1               5                   10

<210> SEQ ID NO 144
<211> LENGTH: 13
<212> TYPE: PRT
<213> ORGANISM: artificial sequence
<220> FEATURE:
<223> OTHER INFORMATION: synthetic peptide

<400> SEQUENCE: 144

Ile Ile Ser Arg Cys Gln Val Cys Met Lys Met Arg Pro
1               5                   10

<210> SEQ ID NO 145
<211> LENGTH: 5
<212> TYPE: PRT
<213> ORGANISM: artificial sequence
<220> FEATURE:
<223> OTHER INFORMATION: synthetic peptide

<400> SEQUENCE: 145

Ile Lys Val Ala Val
1               5

<210> SEQ ID NO 146
<211> LENGTH: 13
```

<212> TYPE: PRT
<213> ORGANISM: artificial sequence
<220> FEATURE:
<223> OTHER INFORMATION: synthetic peptide

<400> SEQUENCE: 146

Ile Arg Ser Leu Lys Leu Thr Lys Gly Thr Gly Lys Pro
1               5                   10

<210> SEQ ID NO 147
<211> LENGTH: 17
<212> TYPE: PRT
<213> ORGANISM: artificial sequence
<220> FEATURE:
<223> OTHER INFORMATION: synthetic peptide

<400> SEQUENCE: 147

Ile Ser Asn Val Phe Val Gln Arg Met Ser Gln Ser Pro Glu Val Leu
1               5                   10                  15

Asp

<210> SEQ ID NO 148
<211> LENGTH: 12
<212> TYPE: PRT
<213> ORGANISM: artificial sequence
<220> FEATURE:
<223> OTHER INFORMATION: synthetic peptide

<400> SEQUENCE: 148

Ile Ser Arg Cys Gln Val Cys Met Lys Lys Arg His
1               5                   10

<210> SEQ ID NO 149
<211> LENGTH: 12
<212> TYPE: PRT
<213> ORGANISM: artificial sequence
<220> FEATURE:
<223> OTHER INFORMATION: synthetic peptide

<400> SEQUENCE: 149

Ile Ser Thr Val Met Phe Lys Phe Arg Thr Phe Ser
1               5                   10

<210> SEQ ID NO 150
<211> LENGTH: 12
<212> TYPE: PRT
<213> ORGANISM: artificial sequence
<220> FEATURE:
<223> OTHER INFORMATION: synthetic peptide

<400> SEQUENCE: 150

Lys Ala Phe Asp Ile Thr Tyr Val Arg Leu Lys Phe
1               5                   10

<210> SEQ ID NO 151
<211> LENGTH: 13
<212> TYPE: PRT
<213> ORGANISM: artificial sequence
<220> FEATURE:
<223> OTHER INFORMATION: synthetic peptide

<400> SEQUENCE: 151

Lys Ala Arg Ser Phe Asn Val Asn Gln Leu Leu Gln Asp
1               5                   10

<210> SEQ ID NO 152

```
<211> LENGTH: 12
<212> TYPE: PRT
<213> ORGANISM: artificial sequence
<220> FEATURE:
<223> OTHER INFORMATION: synthetic peptide

<400> SEQUENCE: 152

Lys Asp Ile Ser Glu Lys Val Ala Val Tyr Ser Thr
1               5                   10

<210> SEQ ID NO 153
<211> LENGTH: 12
<212> TYPE: PRT
<213> ORGANISM: artificial sequence
<220> FEATURE:
<223> OTHER INFORMATION: synthetic peptide

<400> SEQUENCE: 153

Lys Glu Ala Glu Arg Glu Val Thr Asp Leu Leu Arg
1               5                   10

<210> SEQ ID NO 154
<211> LENGTH: 6
<212> TYPE: PRT
<213> ORGANISM: artificial sequence
<220> FEATURE:
<223> OTHER INFORMATION: synthetic peptide

<400> SEQUENCE: 154

Lys Gly His Arg Gly Phe
1               5

<210> SEQ ID NO 155
<211> LENGTH: 6
<212> TYPE: PRT
<213> ORGANISM: artificial sequence
<220> FEATURE:
<223> OTHER INFORMATION: synthetic peptide

<400> SEQUENCE: 155

Lys Gly Ile Arg Gly His
1               5

<210> SEQ ID NO 156
<211> LENGTH: 20
<212> TYPE: PRT
<213> ORGANISM: artificial sequence
<220> FEATURE:
<223> OTHER INFORMATION: synthetic peptide

<400> SEQUENCE: 156

Lys Ile Pro Lys Ala Ser Ser Val Pro Thr Glu Leu Ser Ala Ile Ser
1               5                   10                  15

Thr Leu Tyr Leu
            20

<210> SEQ ID NO 157
<211> LENGTH: 12
<212> TYPE: PRT
<213> ORGANISM: artificial sequence
<220> FEATURE:
<223> OTHER INFORMATION: synthetic peptide

<400> SEQUENCE: 157

Lys Lys Gly Ser Tyr Asn Asn Ile Val Val His Val
1               5                   10
```

<210> SEQ ID NO 158
<211> LENGTH: 16
<212> TYPE: PRT
<213> ORGANISM: artificial sequence
<220> FEATURE:
<223> OTHER INFORMATION: synthetic peptide

<400> SEQUENCE: 158

Lys Lys Gln Arg Phe Arg His Arg Asn Arg Lys Gly Tyr Arg Ser Gln
1               5                   10                  15

<210> SEQ ID NO 159
<211> LENGTH: 6
<212> TYPE: PRT
<213> ORGANISM: artificial sequence
<220> FEATURE:
<223> OTHER INFORMATION: synthetic peptide

<400> SEQUENCE: 159

Lys Leu Asp Ala Pro Thr
1               5

<210> SEQ ID NO 160
<211> LENGTH: 15
<212> TYPE: PRT
<213> ORGANISM: artificial sequence
<220> FEATURE:
<223> OTHER INFORMATION: synthetic peptide

<400> SEQUENCE: 160

Lys Leu Thr Trp Gln Glu Leu Tyr Gln Leu Tyr Lys Gly Ile
1               5                   10                  15

<210> SEQ ID NO 161
<211> LENGTH: 12
<212> TYPE: PRT
<213> ORGANISM: artificial sequence
<220> FEATURE:
<223> OTHER INFORMATION: synthetic peptide

<400> SEQUENCE: 161

Lys Met Pro Tyr Val Ser Leu Glu Leu Glu Met Arg
1               5                   10

<210> SEQ ID NO 162
<211> LENGTH: 15
<212> TYPE: PRT
<213> ORGANISM: artificial sequence
<220> FEATURE:
<223> OTHER INFORMATION: synthetic peptide

<400> SEQUENCE: 162

Lys Asn Asn Gln Lys Ser Glu Pro Leu Ile Gly Arg Lys Lys Thr
1               5                   10                  15

<210> SEQ ID NO 163
<211> LENGTH: 12
<212> TYPE: PRT
<213> ORGANISM: artificial sequence
<220> FEATURE:
<223> OTHER INFORMATION: synthetic peptide

<400> SEQUENCE: 163

Lys Asn Arg Leu Thr Ile Glu Leu Glu Val Arg Thr
1               5                   10

```
<210> SEQ ID NO 164
<211> LENGTH: 12
<212> TYPE: PRT
<213> ORGANISM: artificial sequence
<220> FEATURE:
<223> OTHER INFORMATION: synthetic peptide

<400> SEQUENCE: 164

Lys Asn Ser Phe Met Ala Leu Tyr Leu Ser Lys Gly
1               5                   10

<210> SEQ ID NO 165
<211> LENGTH: 19
<212> TYPE: PRT
<213> ORGANISM: artificial sequence
<220> FEATURE:
<223> OTHER INFORMATION: synthetic peptide

<400> SEQUENCE: 165

Lys Asn Ser Phe Met Ala Leu Tyr Leu Ser Lys Gly Arg Leu Val Phe
1               5                   10                  15

Ala Leu Gly

<210> SEQ ID NO 166
<211> LENGTH: 11
<212> TYPE: PRT
<213> ORGANISM: artificial sequence
<220> FEATURE:
<223> OTHER INFORMATION: synthetic peptide

<400> SEQUENCE: 166

Lys Pro Asp Val Arg Ser Tyr Thr Ile Thr Gly
1               5                   10

<210> SEQ ID NO 167
<211> LENGTH: 12
<212> TYPE: PRT
<213> ORGANISM: artificial sequence
<220> FEATURE:
<223> OTHER INFORMATION: synthetic peptide

<400> SEQUENCE: 167

Lys Pro Arg Leu Gln Phe Ser Leu Asp Ile Gln Thr
1               5                   10

<210> SEQ ID NO 168
<211> LENGTH: 4
<212> TYPE: PRT
<213> ORGANISM: artificial sequence
<220> FEATURE:
<223> OTHER INFORMATION: synthetic peptide

<400> SEQUENCE: 168

Lys Pro Ser Ser
1

<210> SEQ ID NO 169
<211> LENGTH: 13
<212> TYPE: PRT
<213> ORGANISM: artificial sequence
<220> FEATURE:
<223> OTHER INFORMATION: synthetic peptide

<400> SEQUENCE: 169

Lys Gln Ala Asn Ile Ser Ile Val Asp Ile Asp Ser Asn
1               5                   10
```

```
<210> SEQ ID NO 170
<211> LENGTH: 12
<212> TYPE: PRT
<213> ORGANISM: artificial sequence
<220> FEATURE:
<223> OTHER INFORMATION: synthetic peptide

<400> SEQUENCE: 170

Lys Gln Gly Lys Ala Leu Thr Gln Arg His Ala Lys
1               5                   10

<210> SEQ ID NO 171
<211> LENGTH: 22
<212> TYPE: PRT
<213> ORGANISM: artificial sequence
<220> FEATURE:
<223> OTHER INFORMATION: synthetic peptide

<400> SEQUENCE: 171

Lys Gln Asn Cys Leu Ser Ser Arg Ala Ser Phe Arg Gly Cys Val Arg
1               5                   10                  15

Asn Leu Arg Leu Ser Arg
            20

<210> SEQ ID NO 172
<211> LENGTH: 7
<212> TYPE: PRT
<213> ORGANISM: artificial sequence
<220> FEATURE:
<223> OTHER INFORMATION: synthetic peptide

<400> SEQUENCE: 172

Lys Arg Leu Asp Gly Ser Val
1               5

<210> SEQ ID NO 173
<211> LENGTH: 8
<212> TYPE: PRT
<213> ORGANISM: artificial sequence
<220> FEATURE:
<223> OTHER INFORMATION: synthetic peptide

<400> SEQUENCE: 173

Lys Arg Leu Val Thr Gly Gln Arg
1               5

<210> SEQ ID NO 174
<211> LENGTH: 12
<212> TYPE: PRT
<213> ORGANISM: artificial sequence
<220> FEATURE:
<223> OTHER INFORMATION: synthetic peptide

<400> SEQUENCE: 174

Lys Arg Arg Ala Arg Asp Leu Val His Arg Ala Glu
1               5                   10

<210> SEQ ID NO 175
<211> LENGTH: 4
<212> TYPE: PRT
<213> ORGANISM: artificial sequence
<220> FEATURE:
<223> OTHER INFORMATION: synthetic peptide
```

```
<400> SEQUENCE: 175

Lys Arg Ser Arg
1

<210> SEQ ID NO 176
<211> LENGTH: 12
<212> TYPE: PRT
<213> ORGANISM: artificial sequence
<220> FEATURE:
<223> OTHER INFORMATION: synthetic peptide

<400> SEQUENCE: 176

Lys Thr Trp Gly Val Tyr Arg Tyr Phe Ala Tyr Asp
1               5                   10

<210> SEQ ID NO 177
<211> LENGTH: 14
<212> TYPE: PRT
<213> ORGANISM: artificial sequence
<220> FEATURE:
<223> OTHER INFORMATION: synthetic peptide

<400> SEQUENCE: 177

Lys Val Leu Ser Arg Leu Pro Tyr Gly Pro Gly Arg Ser Lys
1               5                   10

<210> SEQ ID NO 178
<211> LENGTH: 12
<212> TYPE: PRT
<213> ORGANISM: artificial sequence
<220> FEATURE:
<223> OTHER INFORMATION: synthetic peptide

<400> SEQUENCE: 178

Lys Val Ser Phe Leu Trp Trp Val Gly Ser Gly Val
1               5                   10

<210> SEQ ID NO 179
<211> LENGTH: 11
<212> TYPE: PRT
<213> ORGANISM: artificial sequence
<220> FEATURE:
<223> OTHER INFORMATION: synthetic peptide

<400> SEQUENCE: 179

Lys Tyr Ile Leu Arg Trp Arg Pro Lys Asn Ser
1               5                   10

<210> SEQ ID NO 180
<211> LENGTH: 12
<212> TYPE: PRT
<213> ORGANISM: artificial sequence
<220> FEATURE:
<223> OTHER INFORMATION: synthetic peptide

<400> SEQUENCE: 180

Leu Ala Gly Ser Cys Leu Ala Arg Phe Ser Thr Met
1               5                   10

<210> SEQ ID NO 181
<211> LENGTH: 12
<212> TYPE: PRT
<213> ORGANISM: artificial sequence
<220> FEATURE:
<223> OTHER INFORMATION: synthetic peptide
```

<400> SEQUENCE: 181

Leu Ala Gly Ser Cys Leu Pro Val Phe Ser Thr Leu
1               5                   10

<210> SEQ ID NO 182
<211> LENGTH: 12
<212> TYPE: PRT
<213> ORGANISM: artificial sequence
<220> FEATURE:
<223> OTHER INFORMATION: synthetic peptide

<400> SEQUENCE: 182

Leu Ala Ile Lys Asn Asp Asn Leu Val Tyr Val Tyr
1               5                   10

<210> SEQ ID NO 183
<211> LENGTH: 10
<212> TYPE: PRT
<213> ORGANISM: artificial sequence
<220> FEATURE:
<223> OTHER INFORMATION: synthetic peptide

<400> SEQUENCE: 183

Leu Ala Leu Glu Arg Lys Asp His Ser Gly
1               5                   10

<210> SEQ ID NO 184
<211> LENGTH: 12
<212> TYPE: PRT
<213> ORGANISM: artificial sequence
<220> FEATURE:
<223> OTHER INFORMATION: synthetic peptide

<400> SEQUENCE: 184

Leu Ala Leu Phe Leu Ser Asn Gly His Phe Val Ala
1               5                   10

<210> SEQ ID NO 185
<211> LENGTH: 5
<212> TYPE: PRT
<213> ORGANISM: artificial sequence
<220> FEATURE:
<223> OTHER INFORMATION: synthetic peptide

<400> SEQUENCE: 185

Leu Asp Val Pro Ser
1               5

<210> SEQ ID NO 186
<211> LENGTH: 12
<212> TYPE: PRT
<213> ORGANISM: artificial sequence
<220> FEATURE:
<223> OTHER INFORMATION: synthetic peptide

<400> SEQUENCE: 186

Leu Glu Ala Glu Phe His Phe Thr His Leu Ile Met
1               5                   10

<210> SEQ ID NO 187
<211> LENGTH: 10
<212> TYPE: PRT
<213> ORGANISM: artificial sequence
<220> FEATURE:
<223> OTHER INFORMATION: synthetic peptide

<400> SEQUENCE: 187

Leu Glu Lys Val Ala His Gln Leu Glu Glu
1               5                   10

<210> SEQ ID NO 188
<211> LENGTH: 13
<212> TYPE: PRT
<213> ORGANISM: artificial sequence
<220> FEATURE:
<223> OTHER INFORMATION: synthetic peptide

<400> SEQUENCE: 188

Leu Glu Pro Arg Arg Glu Val Cys Glu Leu Asn Pro Asp
1               5                   10

<210> SEQ ID NO 189
<211> LENGTH: 10
<212> TYPE: PRT
<213> ORGANISM: artificial sequence
<220> FEATURE:
<223> OTHER INFORMATION: synthetic peptide

<400> SEQUENCE: 189

Leu Phe Ser His Ala Val Ser Ser Asn Gly
1               5                   10

<210> SEQ ID NO 190
<211> LENGTH: 13
<212> TYPE: PRT
<213> ORGANISM: artificial sequence
<220> FEATURE:
<223> OTHER INFORMATION: synthetic peptide

<400> SEQUENCE: 190

Leu Gly Gly Leu Pro Ser His Tyr Arg Ala Arg Asn Ile
1               5                   10

<210> SEQ ID NO 191
<211> LENGTH: 6
<212> TYPE: PRT
<213> ORGANISM: artificial sequence
<220> FEATURE:
<223> OTHER INFORMATION: synthetic peptide

<400> SEQUENCE: 191

Leu Gly Thr Ile Pro Gly
1               5

<210> SEQ ID NO 192
<211> LENGTH: 12
<212> TYPE: PRT
<213> ORGANISM: artificial sequence
<220> FEATURE:
<223> OTHER INFORMATION: synthetic peptide

<400> SEQUENCE: 192

Leu His Lys Lys Gly Lys Asn Ser Ser Lys Pro Lys
1               5                   10

<210> SEQ ID NO 193
<211> LENGTH: 12
<212> TYPE: PRT
<213> ORGANISM: artificial sequence
<220> FEATURE:
<223> OTHER INFORMATION: synthetic peptide

```
<400> SEQUENCE: 193

Leu His Val Phe Tyr Asp Phe Gly Phe Ser Asn Gly
1               5                   10

<210> SEQ ID NO 194
<211> LENGTH: 20
<212> TYPE: PRT
<213> ORGANISM: artificial sequence
<220> FEATURE:
<223> OTHER INFORMATION: synthetic peptide

<400> SEQUENCE: 194

Leu Lys Lys Ala Gln Ile Asn Asp Ala Lys Tyr Arg Glu Ile Ser Ile
1               5                   10                  15

Ile Tyr His Asn
            20

<210> SEQ ID NO 195
<211> LENGTH: 12
<212> TYPE: PRT
<213> ORGANISM: artificial sequence
<220> FEATURE:
<223> OTHER INFORMATION: synthetic peptide

<400> SEQUENCE: 195

Leu Leu Glu Phe Thr Ser Ala Arg Tyr Ile Arg Leu
1               5                   10

<210> SEQ ID NO 196
<211> LENGTH: 10
<212> TYPE: PRT
<213> ORGANISM: artificial sequence
<220> FEATURE:
<223> OTHER INFORMATION: synthetic peptide

<400> SEQUENCE: 196

Leu Asn Arg Gln Glu Leu Phe Pro Phe Gly
1               5                   10

<210> SEQ ID NO 197
<211> LENGTH: 12
<212> TYPE: PRT
<213> ORGANISM: artificial sequence
<220> FEATURE:
<223> OTHER INFORMATION: synthetic peptide

<400> SEQUENCE: 197

Leu Asn Arg Arg Tyr Glu Gln Ala Arg Asn Ile Ser
1               5                   10

<210> SEQ ID NO 198
<211> LENGTH: 13
<212> TYPE: PRT
<213> ORGANISM: artificial sequence
<220> FEATURE:
<223> OTHER INFORMATION: synthetic peptide

<400> SEQUENCE: 198

Leu Pro Phe Phe Asn Asp Arg Pro Trp Arg Arg Ala Thr
1               5                   10

<210> SEQ ID NO 199
<211> LENGTH: 12
<212> TYPE: PRT
<213> ORGANISM: artificial sequence
<220> FEATURE:
```

<223> OTHER INFORMATION: synthetic peptide

<400> SEQUENCE: 199

Leu Gln Gln Ser Arg Ile Ala Asn Ile Ser Met Glu
1               5                   10

<210> SEQ ID NO 200
<211> LENGTH: 9
<212> TYPE: PRT
<213> ORGANISM: artificial sequence
<220> FEATURE:
<223> OTHER INFORMATION: synthetic peptide

<400> SEQUENCE: 200

Leu Gln Val Gln Leu Ser Ile Arg Thr
1               5

<210> SEQ ID NO 201
<211> LENGTH: 10
<212> TYPE: PRT
<213> ORGANISM: artificial sequence
<220> FEATURE:
<223> OTHER INFORMATION: synthetic peptide

<400> SEQUENCE: 201

Leu Arg Ala His Ala Val Asp Ile Asn Gly
1               5                   10

<210> SEQ ID NO 202
<211> LENGTH: 10
<212> TYPE: PRT
<213> ORGANISM: artificial sequence
<220> FEATURE:
<223> OTHER INFORMATION: synthetic peptide

<400> SEQUENCE: 202

Leu Arg Ala His Ala Val Asp Val Asn Gly
1               5                   10

<210> SEQ ID NO 203
<211> LENGTH: 12
<212> TYPE: PRT
<213> ORGANISM: artificial sequence
<220> FEATURE:
<223> OTHER INFORMATION: synthetic peptide

<400> SEQUENCE: 203

Leu Ser Asn Ile Asp Tyr Ile Leu Ile Lys Ala Ser
1               5                   10

<210> SEQ ID NO 204
<211> LENGTH: 14
<212> TYPE: PRT
<213> ORGANISM: artificial sequence
<220> FEATURE:
<223> OTHER INFORMATION: synthetic peptide

<400> SEQUENCE: 204

Leu Thr Arg Tyr Lys Ile Thr Pro Arg Arg Gly Pro Pro Thr
1               5                   10

<210> SEQ ID NO 205
<211> LENGTH: 12
<212> TYPE: PRT
<213> ORGANISM: artificial sequence
<220> FEATURE:
<223> OTHER INFORMATION: synthetic peptide

```
<400> SEQUENCE: 205

Leu Val Phe Met Phe Asn Val Gly His Lys Lys Leu
1               5                  10

<210> SEQ ID NO 206
<211> LENGTH: 10
<212> TYPE: PRT
<213> ORGANISM: artificial sequence
<220> FEATURE:
<223> OTHER INFORMATION: synthetic peptide

<400> SEQUENCE: 206

Leu Val Val Gln Ala Ala Asp Leu Gln Gly
1               5                  10

<210> SEQ ID NO 207
<211> LENGTH: 12
<212> TYPE: PRT
<213> ORGANISM: artificial sequence
<220> FEATURE:
<223> OTHER INFORMATION: synthetic peptide

<400> SEQUENCE: 207

Leu Trp Pro Leu Leu Ala Val Leu Ala Ala Val Ala
1               5                  10

<210> SEQ ID NO 208
<211> LENGTH: 13
<212> TYPE: PRT
<213> ORGANISM: artificial sequence
<220> FEATURE:
<223> OTHER INFORMATION: synthetic peptide

<400> SEQUENCE: 208

Leu Trp Val Thr Val Arg Ser Gln Gln Arg Gly Leu Phe
1               5                  10

<210> SEQ ID NO 209
<211> LENGTH: 12
<212> TYPE: PRT
<213> ORGANISM: artificial sequence
<220> FEATURE:
<223> OTHER INFORMATION: synthetic peptide

<400> SEQUENCE: 209

Met Glu Met Gln Ala Asn Leu Leu Leu Asp Arg Leu
1               5                  10

<210> SEQ ID NO 210
<211> LENGTH: 16
<212> TYPE: PRT
<213> ORGANISM: artificial sequence
<220> FEATURE:
<223> OTHER INFORMATION: synthetic peptide

<400> SEQUENCE: 210

Met Phe Lys Lys Pro Thr Pro Ser Thr Leu Lys Ala Gly Glu Leu Arg
1               5                  10                  15

<210> SEQ ID NO 211
<211> LENGTH: 12
<212> TYPE: PRT
<213> ORGANISM: artificial sequence
<220> FEATURE:
<223> OTHER INFORMATION: synthetic peptide
```

<400> SEQUENCE: 211

Met Phe Arg Lys Pro Ile Pro Ser Thr Val Lys Ala
1               5                   10

<210> SEQ ID NO 212
<211> LENGTH: 13
<212> TYPE: PRT
<213> ORGANISM: artificial sequence
<220> FEATURE:
<223> OTHER INFORMATION: synthetic peptide

<400> SEQUENCE: 212

Met Ile Leu Ile Ser Ile Gly Lys Ser Gln Lys Arg Met
1               5                   10

<210> SEQ ID NO 213
<211> LENGTH: 10
<212> TYPE: PRT
<213> ORGANISM: artificial sequence
<220> FEATURE:
<223> OTHER INFORMATION: synthetic peptide

<400> SEQUENCE: 213

Met Lys Val Ser Ala Thr Asp Ala Asp Asp
1               5                   10

<210> SEQ ID NO 214
<211> LENGTH: 7
<212> TYPE: PRT
<213> ORGANISM: artificial sequence
<220> FEATURE:
<223> OTHER INFORMATION: synthetic peptide

<400> SEQUENCE: 214

Met Asn Tyr Tyr Ser Asn Ser
1               5

<210> SEQ ID NO 215
<211> LENGTH: 12
<212> TYPE: PRT
<213> ORGANISM: artificial sequence
<220> FEATURE:
<223> OTHER INFORMATION: synthetic peptide

<400> SEQUENCE: 215

Asn Ala Pro Phe Pro Lys Leu Ser Trp Thr Ile Gln
1               5                   10

<210> SEQ ID NO 216
<211> LENGTH: 11
<212> TYPE: PRT
<213> ORGANISM: artificial sequence
<220> FEATURE:
<223> OTHER INFORMATION: synthetic peptide

<400> SEQUENCE: 216

Asn Ala Val Gly Tyr Ser Val Tyr Asp Ile Ser
1               5                   10

<210> SEQ ID NO 217
<211> LENGTH: 10
<212> TYPE: PRT
<213> ORGANISM: artificial sequence
<220> FEATURE:
<223> OTHER INFORMATION: synthetic peptide

<400> SEQUENCE: 217

Asn Asp Asp Gly Gly Gln Phe Val Val Thr
1               5                   10

<210> SEQ ID NO 218
<211> LENGTH: 13
<212> TYPE: PRT
<213> ORGANISM: artificial sequence
<220> FEATURE:
<223> OTHER INFORMATION: synthetic peptide

<400> SEQUENCE: 218

Asn Glu Pro Lys Val Leu Lys Ser Tyr Tyr Tyr Ala Ile
1               5                   10

<210> SEQ ID NO 219
<211> LENGTH: 12
<212> TYPE: PRT
<213> ORGANISM: artificial sequence
<220> FEATURE:
<223> OTHER INFORMATION: synthetic peptide

<400> SEQUENCE: 219

Asn Gly Glu Pro Arg Gly Asp Thr Tyr Arg Ala Tyr
1               5                   10

<210> SEQ ID NO 220
<211> LENGTH: 12
<212> TYPE: PRT
<213> ORGANISM: artificial sequence
<220> FEATURE:
<223> OTHER INFORMATION: synthetic peptide

<400> SEQUENCE: 220

Asn Gly Gln Trp His Lys Val Thr Ala Lys Lys Ile
1               5                   10

<210> SEQ ID NO 221
<211> LENGTH: 3
<212> TYPE: PRT
<213> ORGANISM: artificial sequence
<220> FEATURE:
<223> OTHER INFORMATION: synthetic peptide

<400> SEQUENCE: 221

Asn Gly Arg
1

<210> SEQ ID NO 222
<211> LENGTH: 9
<212> TYPE: PRT
<213> ORGANISM: artificial sequence
<220> FEATURE:
<223> OTHER INFORMATION: synthetic peptide

<400> SEQUENCE: 222

Asn His Gly Phe Val Val Glu Val Thr
1               5

<210> SEQ ID NO 223
<211> LENGTH: 12
<212> TYPE: PRT
<213> ORGANISM: artificial sequence
<220> FEATURE:
<223> OTHER INFORMATION: synthetic peptide

```
<400> SEQUENCE: 223

Asn Ile Arg Leu Arg Phe Leu Arg Thr Asn Thr Leu
1               5                   10

<210> SEQ ID NO 224
<211> LENGTH: 6
<212> TYPE: PRT
<213> ORGANISM: artificial sequence
<220> FEATURE:
<223> OTHER INFORMATION: synthetic peptide

<400> SEQUENCE: 224

Asn Lys Arg Ala His Gly
1               5

<210> SEQ ID NO 225
<211> LENGTH: 12
<212> TYPE: PRT
<213> ORGANISM: artificial sequence
<220> FEATURE:
<223> OTHER INFORMATION: synthetic peptide

<400> SEQUENCE: 225

Asn Leu Leu Leu Leu Val Lys Ala Asn Leu Lys
1               5                   10

<210> SEQ ID NO 226
<211> LENGTH: 7
<212> TYPE: PRT
<213> ORGANISM: artificial sequence
<220> FEATURE:
<223> OTHER INFORMATION: synthetic peptide

<400> SEQUENCE: 226

Asn Leu Leu Met Ala Ala Ser
1               5

<210> SEQ ID NO 227
<211> LENGTH: 12
<212> TYPE: PRT
<213> ORGANISM: artificial sequence
<220> FEATURE:
<223> OTHER INFORMATION: synthetic peptide

<400> SEQUENCE: 227

Asn Pro Trp His Ser Ile Tyr Ile Thr Arg Phe Gly
1               5                   10

<210> SEQ ID NO 228
<211> LENGTH: 13
<212> TYPE: PRT
<213> ORGANISM: artificial sequence
<220> FEATURE:
<223> OTHER INFORMATION: synthetic peptide

<400> SEQUENCE: 228

Asn Gln Phe Gly Leu Thr Thr Asn Ile Arg Phe Arg Gly
1               5                   10

<210> SEQ ID NO 229
<211> LENGTH: 13
<212> TYPE: PRT
<213> ORGANISM: artificial sequence
<220> FEATURE:
<223> OTHER INFORMATION: synthetic peptide
```

<400> SEQUENCE: 229

Asn Gln Arg Leu Ala Ser Phe Ser Asn Ala Gln Gln Ser
1               5                   10

<210> SEQ ID NO 230
<211> LENGTH: 12
<212> TYPE: PRT
<213> ORGANISM: artificial sequence
<220> FEATURE:
<223> OTHER INFORMATION: synthetic peptide

<400> SEQUENCE: 230

Asn Arg Trp His Ser Ile Tyr Ile Thr Arg Phe Gly
1               5                   10

<210> SEQ ID NO 231
<211> LENGTH: 50
<212> TYPE: PRT
<213> ORGANISM: artificial sequence
<220> FEATURE:
<223> OTHER INFORMATION: synthetic peptide

<400> SEQUENCE: 231

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp
    50

<210> SEQ ID NO 232
<211> LENGTH: 12
<212> TYPE: PRT
<213> ORGANISM: artificial sequence
<220> FEATURE:
<223> OTHER INFORMATION: synthetic peptide

<400> SEQUENCE: 232

Asn Val Leu Ser Leu Tyr Asn Phe Lys Thr Thr Phe
1               5                   10

<210> SEQ ID NO 233
<211> LENGTH: 5
<212> TYPE: PRT
<213> ORGANISM: artificial sequence
<220> FEATURE:
<223> OTHER INFORMATION: synthetic peptide

<400> SEQUENCE: 233

Pro Asp Ser Gly Arg
1               5

<210> SEQ ID NO 234
<211> LENGTH: 12
<212> TYPE: PRT
<213> ORGANISM: artificial sequence
<220> FEATURE:
<223> OTHER INFORMATION: synthetic peptide

<400> SEQUENCE: 234

Pro Gly Gly Met Arg Glu Lys Gly Arg Lys Ala Arg
1               5                   10

```
<210> SEQ ID NO 235
<211> LENGTH: 12
<212> TYPE: PRT
<213> ORGANISM: artificial sequence
<220> FEATURE:
<223> OTHER INFORMATION: synthetic peptide

<400> SEQUENCE: 235

Pro Gly Arg Trp His Lys Val Ser Val Arg Trp Glu
1               5                  10

<210> SEQ ID NO 236
<211> LENGTH: 5
<212> TYPE: PRT
<213> ORGANISM: artificial sequence
<220> FEATURE:
<223> OTHER INFORMATION: synthetic peptide

<400> SEQUENCE: 236

Pro Gly Val Gly Val
1               5

<210> SEQ ID NO 237
<211> LENGTH: 5
<212> TYPE: PRT
<213> ORGANISM: artificial sequence
<220> FEATURE:
<223> OTHER INFORMATION: synthetic peptide

<400> SEQUENCE: 237

Pro His Ser Arg Asn
1               5

<210> SEQ ID NO 238
<211> LENGTH: 9
<212> TYPE: PRT
<213> ORGANISM: artificial sequence
<220> FEATURE:
<223> OTHER INFORMATION: synthetic peptide

<400> SEQUENCE: 238

Pro Lys Gly Gln Lys Gly Glu Lys Gly
1               5

<210> SEQ ID NO 239
<211> LENGTH: 10
<212> TYPE: PRT
<213> ORGANISM: artificial sequence
<220> FEATURE:
<223> OTHER INFORMATION: synthetic peptide

<400> SEQUENCE: 239

Pro Leu Asp Arg Glu Ala Ile Ala Lys Tyr
1               5                  10

<210> SEQ ID NO 240
<211> LENGTH: 12
<212> TYPE: PRT
<213> ORGANISM: artificial sequence
<220> FEATURE:
<223> OTHER INFORMATION: synthetic peptide

<400> SEQUENCE: 240

Pro Pro Phe Leu Met Leu Leu Lys Gly Ser Thr Arg
1               5                  10
```

```
<210> SEQ ID NO 241
<211> LENGTH: 12
<212> TYPE: PRT
<213> ORGANISM: artificial sequence
<220> FEATURE:
<223> OTHER INFORMATION: synthetic peptide

<400> SEQUENCE: 241

Pro Gln Val Thr Arg Gly Asp Val Phe Thr Met Pro
1               5                   10

<210> SEQ ID NO 242
<211> LENGTH: 26
<212> TYPE: PRT
<213> ORGANISM: artificial sequence
<220> FEATURE:
<223> OTHER INFORMATION: synthetic peptide

<400> SEQUENCE: 242

Pro Arg Ala Arg Ile Thr Gly Tyr Ile Ile Lys Tyr Glu Lys Pro Gly
1               5                   10                  15

Ser Pro Pro Arg Glu Val Val Pro Arg Pro
            20                  25

<210> SEQ ID NO 243
<211> LENGTH: 14
<212> TYPE: PRT
<213> ORGANISM: artificial sequence
<220> FEATURE:
<223> OTHER INFORMATION: synthetic peptide

<400> SEQUENCE: 243

Pro Ser Lys Lys Thr Lys Pro Val Lys Pro Lys Lys Val Ala
1               5                   10

<210> SEQ ID NO 244
<211> LENGTH: 10
<212> TYPE: PRT
<213> ORGANISM: artificial sequence
<220> FEATURE:
<223> OTHER INFORMATION: synthetic peptide

<400> SEQUENCE: 244

Gln Asp Pro Glu Leu Pro Asp Lys Asn Met
1               5                   10

<210> SEQ ID NO 245
<211> LENGTH: 10
<212> TYPE: PRT
<213> ORGANISM: artificial sequence
<220> FEATURE:
<223> OTHER INFORMATION: synthetic peptide

<400> SEQUENCE: 245

Gln Gly Ala Asp Thr Pro Pro Val Gly Val
1               5                   10

<210> SEQ ID NO 246
<211> LENGTH: 13
<212> TYPE: PRT
<213> ORGANISM: artificial sequence
<220> FEATURE:
<223> OTHER INFORMATION: synthetic peptide
```

<400> SEQUENCE: 246

Gln Lys Ile Ala Glu Lys Phe Ser Gly Thr Arg Arg Gly
1               5                   10

<210> SEQ ID NO 247
<211> LENGTH: 12
<212> TYPE: PRT
<213> ORGANISM: artificial sequence
<220> FEATURE:
<223> OTHER INFORMATION: synthetic peptide

<400> SEQUENCE: 247

Gln Gln Asn Leu Gly Ser Val Asn Val Ser Thr Gly
1               5                   10

<210> SEQ ID NO 248
<211> LENGTH: 23
<212> TYPE: PRT
<213> ORGANISM: artificial sequence
<220> FEATURE:
<223> OTHER INFORMATION: synthetic peptide

<400> SEQUENCE: 248

Gln Arg Val Glu Ile Leu Glu Gly Arg Thr Glu Cys Val Leu Ser Asn
1               5                   10                  15

Leu Arg Gly Arg Thr Arg Tyr
            20

<210> SEQ ID NO 249
<211> LENGTH: 12
<212> TYPE: PRT
<213> ORGANISM: artificial sequence
<220> FEATURE:
<223> OTHER INFORMATION: synthetic peptide

<400> SEQUENCE: 249

Arg Ala Tyr Phe Asn Gly Gln Ser Phe Ile Ala Ser
1               5                   10

<210> SEQ ID NO 250
<211> LENGTH: 15
<212> TYPE: PRT
<213> ORGANISM: artificial sequence
<220> FEATURE:
<223> OTHER INFORMATION: synthetic peptide

<400> SEQUENCE: 250

Arg Asp Phe Thr Lys Ala Thr Asn Ile Arg Leu Arg Phe Leu Arg
1               5                   10                  15

<210> SEQ ID NO 251
<211> LENGTH: 10
<212> TYPE: PRT
<213> ORGANISM: artificial sequence
<220> FEATURE:
<223> OTHER INFORMATION: synthetic peptide

<400> SEQUENCE: 251

Arg Asp Ile Ala Glu Ile Ile Lys Asp Ile
1               5                   10

<210> SEQ ID NO 252
<211> LENGTH: 12
<212> TYPE: PRT
<213> ORGANISM: artificial sequence

```
<220> FEATURE:
<223> OTHER INFORMATION: synthetic peptide

<400> SEQUENCE: 252

Arg Asp Gln Leu Met Thr Val Leu Ala Asn Val Thr
1               5                   10

<210> SEQ ID NO 253
<211> LENGTH: 19
<212> TYPE: PRT
<213> ORGANISM: artificial sequence
<220> FEATURE:
<223> OTHER INFORMATION: synthetic peptide

<400> SEQUENCE: 253

Arg Asp Ser Phe Val Ala Leu Tyr Leu Ser Glu Gly His Val Ile Phe
1               5                   10                  15

Ala Leu Gly

<210> SEQ ID NO 254
<211> LENGTH: 12
<212> TYPE: PRT
<213> ORGANISM: artificial sequence
<220> FEATURE:
<223> OTHER INFORMATION: synthetic peptide

<400> SEQUENCE: 254

Arg Glu Lys Tyr Tyr Tyr Ala Val Tyr Asp Met Val
1               5                   10

<210> SEQ ID NO 255
<211> LENGTH: 12
<212> TYPE: PRT
<213> ORGANISM: artificial sequence
<220> FEATURE:
<223> OTHER INFORMATION: synthetic peptide

<400> SEQUENCE: 255

Arg Phe Asp Gln Glu Leu Arg Leu Val Ser Tyr Asn
1               5                   10

<210> SEQ ID NO 256
<211> LENGTH: 9
<212> TYPE: PRT
<213> ORGANISM: artificial sequence
<220> FEATURE:
<223> OTHER INFORMATION: synthetic peptide

<400> SEQUENCE: 256

Arg Gly Gln Pro Gly Arg Lys Gly Leu
1               5

<210> SEQ ID NO 257
<211> LENGTH: 9
<212> TYPE: PRT
<213> ORGANISM: artificial sequence
<220> FEATURE:
<223> OTHER INFORMATION: synthetic peptide

<400> SEQUENCE: 257

Arg Gly Gln Pro Gly Val Met Gly Phe
1               5

<210> SEQ ID NO 258
<211> LENGTH: 15
<212> TYPE: PRT
```

```
<213> ORGANISM: artificial sequence
<220> FEATURE:
<223> OTHER INFORMATION: synthetic peptide

<400> SEQUENCE: 258

Arg Gly Gln Pro Gly Val Pro Gly Val Pro Gly Met Lys Gly Asp
1               5                   10                  15

<210> SEQ ID NO 259
<211> LENGTH: 9
<212> TYPE: PRT
<213> ORGANISM: artificial sequence
<220> FEATURE:
<223> OTHER INFORMATION: synthetic peptide

<400> SEQUENCE: 259

Arg His Val Arg Ile Ser Arg Ser Leu
1               5

<210> SEQ ID NO 260
<211> LENGTH: 20
<212> TYPE: PRT
<213> ORGANISM: artificial sequence
<220> FEATURE:
<223> OTHER INFORMATION: synthetic peptide

<400> SEQUENCE: 260

Arg Ile Leu Ser Ile Leu Arg His Gln Asn Leu Leu Lys Glu Leu Gln
1               5                   10                  15

Asp Leu Ala Leu
            20

<210> SEQ ID NO 261
<211> LENGTH: 17
<212> TYPE: PRT
<213> ORGANISM: artificial sequence
<220> FEATURE:
<223> OTHER INFORMATION: synthetic peptide

<400> SEQUENCE: 261

Arg Ile Gln Asn Leu Leu Lys Ile Thr Asn Leu Arg Ile Lys Phe Val
1               5                   10                  15

Lys

<210> SEQ ID NO 262
<211> LENGTH: 21
<212> TYPE: PRT
<213> ORGANISM: artificial sequence
<220> FEATURE:
<223> OTHER INFORMATION: synthetic peptide

<400> SEQUENCE: 262

Arg Lys Ile Pro Lys Ala Ser Ser Val Pro Thr Glu Leu Ser Ala Ile
1               5                   10                  15

Ser Met Leu Tyr Leu
            20

<210> SEQ ID NO 263
<211> LENGTH: 8
<212> TYPE: PRT
<213> ORGANISM: artificial sequence
<220> FEATURE:
<223> OTHER INFORMATION: synthetic peptide
```

```
<400> SEQUENCE: 263

Arg Lys Leu Lys His Met Arg Phe
1               5

<210> SEQ ID NO 264
<211> LENGTH: 12
<212> TYPE: PRT
<213> ORGANISM: artificial sequence
<220> FEATURE:
<223> OTHER INFORMATION: synthetic peptide

<400> SEQUENCE: 264

Arg Lys Arg Leu Gln Val Gln Leu Ser Ile Arg Thr
1               5                   10

<210> SEQ ID NO 265
<211> LENGTH: 21
<212> TYPE: PRT
<213> ORGANISM: artificial sequence
<220> FEATURE:
<223> OTHER INFORMATION: synthetic peptide

<400> SEQUENCE: 265

Arg Lys Val Gly Lys Ala Ser Ser Val Pro Thr Lys Leu Ser Pro Ile
1               5                   10                  15

Ser Ile Leu Tyr Lys
            20

<210> SEQ ID NO 266
<211> LENGTH: 12
<212> TYPE: PRT
<213> ORGANISM: artificial sequence
<220> FEATURE:
<223> OTHER INFORMATION: synthetic peptide

<400> SEQUENCE: 266

Arg Leu Lys Thr Arg Ser Ser His Gly Met Ile Phe
1               5                   10

<210> SEQ ID NO 267
<211> LENGTH: 12
<212> TYPE: PRT
<213> ORGANISM: artificial sequence
<220> FEATURE:
<223> OTHER INFORMATION: synthetic peptide

<400> SEQUENCE: 267

Arg Leu Arg Gly Pro Gln Arg Val Phe Asp Leu His
1               5                   10

<210> SEQ ID NO 268
<211> LENGTH: 13
<212> TYPE: PRT
<213> ORGANISM: artificial sequence
<220> FEATURE:
<223> OTHER INFORMATION: synthetic peptide

<400> SEQUENCE: 268

Arg Leu Val Ser Tyr Asn Gly Ile Ile Phe Phe Leu Lys
1               5                   10

<210> SEQ ID NO 269
<211> LENGTH: 13
<212> TYPE: PRT
<213> ORGANISM: artificial sequence
```

```
<220> FEATURE:
<223> OTHER INFORMATION: synthetic peptide

<400> SEQUENCE: 269

Arg Leu Val Ser Tyr Ser Gly Val Leu Phe Phe Leu Lys
1               5                   10

<210> SEQ ID NO 270
<211> LENGTH: 10
<212> TYPE: PRT
<213> ORGANISM: artificial sequence
<220> FEATURE:
<223> OTHER INFORMATION: synthetic peptide

<400> SEQUENCE: 270

Arg Asn Ile Ala Glu Ile Ile Lys Asp Ile
1               5                   10

<210> SEQ ID NO 271
<211> LENGTH: 12
<212> TYPE: PRT
<213> ORGANISM: artificial sequence
<220> FEATURE:
<223> OTHER INFORMATION: synthetic peptide

<400> SEQUENCE: 271

Arg Asn Arg Leu His Leu Ser Met Leu Val Arg Pro
1               5                   10

<210> SEQ ID NO 272
<211> LENGTH: 4
<212> TYPE: PRT
<213> ORGANISM: artificial sequence
<220> FEATURE:
<223> OTHER INFORMATION: synthetic peptide

<400> SEQUENCE: 272

Arg Pro Gly Val
1

<210> SEQ ID NO 273
<211> LENGTH: 13
<212> TYPE: PRT
<213> ORGANISM: artificial sequence
<220> FEATURE:
<223> OTHER INFORMATION: synthetic peptide

<400> SEQUENCE: 273

Arg Gln Val Phe Gln Val Ala Tyr Ile Ile Ile Lys Ala
1               5                   10

<210> SEQ ID NO 274
<211> LENGTH: 12
<212> TYPE: PRT
<213> ORGANISM: artificial sequence
<220> FEATURE:
<223> OTHER INFORMATION: synthetic peptide

<400> SEQUENCE: 274

Arg Arg Gln Thr Thr Gln Ala Tyr Tyr Ala Ile Phe
1               5                   10

<210> SEQ ID NO 275
<211> LENGTH: 25
<212> TYPE: PRT
<213> ORGANISM: artificial sequence
<220> FEATURE:
```

<223> OTHER INFORMATION: synthetic peptide

<400> SEQUENCE: 275

Arg Arg Trp Arg Arg Trp Trp Arg Arg Trp Trp Arg Trp Arg Arg
1               5                   10                  15

Pro Val Pro Glu Tyr Ile Asn Gln Ser
            20                  25

<210> SEQ ID NO 276
<211> LENGTH: 12
<212> TYPE: PRT
<213> ORGANISM: artificial sequence
<220> FEATURE:
<223> OTHER INFORMATION: synthetic peptide

<400> SEQUENCE: 276

Arg Arg Tyr Tyr Tyr Ser Ile Lys Asp Ile Ser Val
1               5                   10

<210> SEQ ID NO 277
<211> LENGTH: 15
<212> TYPE: PRT
<213> ORGANISM: artificial sequence
<220> FEATURE:
<223> OTHER INFORMATION: synthetic peptide

<400> SEQUENCE: 277

Arg Ser Met Arg Leu Ser Phe Arg Ala Arg Gly Tyr Gly Phe Arg
1               5                   10                  15

<210> SEQ ID NO 278
<211> LENGTH: 15
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: norleucine

<400> SEQUENCE: 278

Arg Thr Xaa Arg Leu Thr Trp Arg Ala Arg Gly Tyr Gly Trp Arg
1               5                   10                  15

<210> SEQ ID NO 279
<211> LENGTH: 21
<212> TYPE: PRT
<213> ORGANISM: artificial sequence
<220> FEATURE:
<223> OTHER INFORMATION: synthetic peptide

<400> SEQUENCE: 279

Arg Thr Val Pro Lys Pro Ser Ser Ala Pro Thr Gln Leu Asn Ala Ile
1               5                   10                  15

Ser Thr Leu Tyr Phe
            20

<210> SEQ ID NO 280
<211> LENGTH: 7
<212> TYPE: PRT
<213> ORGANISM: artificial sequence
<220> FEATURE:
<223> OTHER INFORMATION: synthetic peptide

<400> SEQUENCE: 280

Arg Tyr Val Val Leu Pro Arg
1               5

<210> SEQ ID NO 281
<211> LENGTH: 13
<212> TYPE: PRT
<213> ORGANISM: artificial sequence
<220> FEATURE:
<223> OTHER INFORMATION: synthetic peptide

<400> SEQUENCE: 281

Ser Glu Thr Thr Val Lys Tyr Ile Phe Arg Leu His Glu
1               5                   10

<210> SEQ ID NO 282
<211> LENGTH: 12
<212> TYPE: PRT
<213> ORGANISM: artificial sequence
<220> FEATURE:
<223> OTHER INFORMATION: synthetic peptide

<400> SEQUENCE: 282

Ser Phe Ser Phe Arg Val Asp Arg Arg Asp Thr Arg
1               5                   10

<210> SEQ ID NO 283
<211> LENGTH: 13
<212> TYPE: PRT
<213> ORGANISM: artificial sequence
<220> FEATURE:
<223> OTHER INFORMATION: synthetic peptide

<400> SEQUENCE: 283

Ser Ile Asp Arg Val Glu Pro Tyr Ser Ser Thr Ala Gln
1               5                   10

<210> SEQ ID NO 284
<211> LENGTH: 11
<212> TYPE: PRT
<213> ORGANISM: artificial sequence
<220> FEATURE:
<223> OTHER INFORMATION: synthetic peptide

<400> SEQUENCE: 284

Ser Ile Gly Phe Arg Gly Asp Gly Gln Thr Cys
1               5                   10

<210> SEQ ID NO 285
<211> LENGTH: 13
<212> TYPE: PRT
<213> ORGANISM: artificial sequence
<220> FEATURE:
<223> OTHER INFORMATION: synthetic peptide

<400> SEQUENCE: 285

Ser Ile Gly Leu Trp Asn Tyr Ile Glu Arg Glu Gly Lys
1               5                   10

<210> SEQ ID NO 286
<211> LENGTH: 12
<212> TYPE: PRT
<213> ORGANISM: artificial sequence
<220> FEATURE:
<223> OTHER INFORMATION: synthetic peptide

```
<400> SEQUENCE: 286

Ser Ile Asn Asn Thr Ala Val Met Gln Arg Leu Thr
1               5                   10

<210> SEQ ID NO 287
<211> LENGTH: 7
<212> TYPE: PRT
<213> ORGANISM: artificial sequence
<220> FEATURE:
<223> OTHER INFORMATION: synthetic peptide

<400> SEQUENCE: 287

Ser Ile Tyr Ile Thr Arg Phe
1               5

<210> SEQ ID NO 288
<211> LENGTH: 12
<212> TYPE: PRT
<213> ORGANISM: artificial sequence
<220> FEATURE:
<223> OTHER INFORMATION: synthetic peptide

<400> SEQUENCE: 288

Ser Leu Leu Ser Gln Leu Asn Asn Leu Leu Asp Gln
1               5                   10

<210> SEQ ID NO 289
<211> LENGTH: 12
<212> TYPE: PRT
<213> ORGANISM: artificial sequence
<220> FEATURE:
<223> OTHER INFORMATION: synthetic peptide

<400> SEQUENCE: 289

Ser Leu Val Arg Asn Arg Arg Val Ile Thr Ile Gln
1               5                   10

<210> SEQ ID NO 290
<211> LENGTH: 9
<212> TYPE: PRT
<213> ORGANISM: artificial sequence
<220> FEATURE:
<223> OTHER INFORMATION: synthetic peptide

<400> SEQUENCE: 290

Ser Pro Pro Arg Arg Ala Arg Val Thr
1               5

<210> SEQ ID NO 291
<211> LENGTH: 14
<212> TYPE: PRT
<213> ORGANISM: artificial sequence
<220> FEATURE:
<223> OTHER INFORMATION: synthetic peptide

<400> SEQUENCE: 291

Ser Pro Tyr Thr Phe Ile Asp Ser Leu Val Leu Met Pro Tyr
1               5                   10

<210> SEQ ID NO 292
<211> LENGTH: 12
<212> TYPE: PRT
<213> ORGANISM: artificial sequence
<220> FEATURE:
<223> OTHER INFORMATION: synthetic peptide
```

<400> SEQUENCE: 292

Ser Gln Phe Gln Glu Ser Val Asp Asn Ile Thr Lys
1               5                   10

<210> SEQ ID NO 293
<211> LENGTH: 13
<212> TYPE: PRT
<213> ORGANISM: artificial sequence
<220> FEATURE:
<223> OTHER INFORMATION: synthetic peptide

<400> SEQUENCE: 293

Ser Gln Arg Ile Tyr Gln Phe Ala Lys Leu Asn Tyr Thr
1               5                   10

<210> SEQ ID NO 294
<211> LENGTH: 12
<212> TYPE: PRT
<213> ORGANISM: artificial sequence
<220> FEATURE:
<223> OTHER INFORMATION: synthetic peptide

<400> SEQUENCE: 294

Ser Arg Ala Thr Ala Gln Lys Val Ser Arg Arg Ser
1               5                   10

<210> SEQ ID NO 295
<211> LENGTH: 12
<212> TYPE: PRT
<213> ORGANISM: artificial sequence
<220> FEATURE:
<223> OTHER INFORMATION: synthetic peptide

<400> SEQUENCE: 295

Ser Arg Leu Arg Gly Lys Asn Pro Thr Lys Gly Lys
1               5                   10

<210> SEQ ID NO 296
<211> LENGTH: 12
<212> TYPE: PRT
<213> ORGANISM: artificial sequence
<220> FEATURE:
<223> OTHER INFORMATION: synthetic peptide

<400> SEQUENCE: 296

Ser Ser Phe His Phe Asp Gly Ser Gly Tyr Ala Met
1               5                   10

<210> SEQ ID NO 297
<211> LENGTH: 7
<212> TYPE: PRT
<213> ORGANISM: artificial sequence
<220> FEATURE:
<223> OTHER INFORMATION: synthetic peptide

<400> SEQUENCE: 297

Ser Val Val Tyr Gly Leu Arg
1               5

<210> SEQ ID NO 298
<211> LENGTH: 12
<212> TYPE: PRT
<213> ORGANISM: artificial sequence
<220> FEATURE:
<223> OTHER INFORMATION: synthetic peptide

```
<400> SEQUENCE: 298

Ser Tyr Trp Tyr Arg Ile Glu Ala Ser Arg Thr Gly
1               5                   10

<210> SEQ ID NO 299
<211> LENGTH: 12
<212> TYPE: PRT
<213> ORGANISM: artificial sequence
<220> FEATURE:
<223> OTHER INFORMATION: synthetic peptide

<400> SEQUENCE: 299

Thr Ala Gly Ser Cys Leu Arg Lys Phe Ser Thr Met
1               5                   10

<210> SEQ ID NO 300
<211> LENGTH: 12
<212> TYPE: PRT
<213> ORGANISM: artificial sequence
<220> FEATURE:
<223> OTHER INFORMATION: synthetic peptide

<400> SEQUENCE: 300

Thr Ala Gly Ser Cys Leu Arg Arg Phe Ser Thr Met
1               5                   10

<210> SEQ ID NO 301
<211> LENGTH: 15
<212> TYPE: PRT
<213> ORGANISM: artificial sequence
<220> FEATURE:
<223> OTHER INFORMATION: synthetic peptide

<400> SEQUENCE: 301

Thr Ala Ile Pro Ser Cys Pro Glu Gly Thr Val Pro Leu Tyr Ser
1               5                   10                  15

<210> SEQ ID NO 302
<211> LENGTH: 15
<212> TYPE: PRT
<213> ORGANISM: artificial sequence
<220> FEATURE:
<223> OTHER INFORMATION: synthetic peptide

<400> SEQUENCE: 302

Thr Asp Ile Pro Pro Cys Pro His Gly Trp Ile Ser Leu Trp Lys
1               5                   10                  15

<210> SEQ ID NO 303
<211> LENGTH: 13
<212> TYPE: PRT
<213> ORGANISM: artificial sequence
<220> FEATURE:
<223> OTHER INFORMATION: synthetic peptide

<400> SEQUENCE: 303

Thr Asp Ile Arg Val Thr Leu Asn Arg Leu Asn Thr Phe
1               5                   10

<210> SEQ ID NO 304
<211> LENGTH: 13
<212> TYPE: PRT
<213> ORGANISM: artificial sequence
<220> FEATURE:
<223> OTHER INFORMATION: synthetic peptide
```

<400> SEQUENCE: 304

Thr Phe Asp Leu Leu Arg Asn Ser Tyr Gly Val Arg Lys
1               5                   10

<210> SEQ ID NO 305
<211> LENGTH: 12
<212> TYPE: PRT
<213> ORGANISM: artificial sequence
<220> FEATURE:
<223> OTHER INFORMATION: synthetic peptide

<400> SEQUENCE: 305

Thr Leu Phe Leu Ala His Gly Arg Leu Val Phe Met
1               5                   10

<210> SEQ ID NO 306
<211> LENGTH: 20
<212> TYPE: PRT
<213> ORGANISM: artificial sequence
<220> FEATURE:
<223> OTHER INFORMATION: synthetic peptide

<400> SEQUENCE: 306

Thr Leu Phe Leu Ala His Gly Arg Leu Val Phe Met Phe Asn Val Gly
1               5                   10                  15

His Lys Lys Leu
            20

<210> SEQ ID NO 307
<211> LENGTH: 12
<212> TYPE: PRT
<213> ORGANISM: artificial sequence
<220> FEATURE:
<223> OTHER INFORMATION: synthetic peptide

<400> SEQUENCE: 307

Thr Leu Gly Ser Cys Leu Gln Arg Phe Thr Thr Met
1               5                   10

<210> SEQ ID NO 308
<211> LENGTH: 9
<212> TYPE: PRT
<213> ORGANISM: artificial sequence
<220> FEATURE:
<223> OTHER INFORMATION: synthetic peptide

<400> SEQUENCE: 308

Thr Leu Val Asn Ser Val Asn Ser Lys
1               5

<210> SEQ ID NO 309
<211> LENGTH: 12
<212> TYPE: PRT
<213> ORGANISM: artificial sequence
<220> FEATURE:
<223> OTHER INFORMATION: synthetic peptide

<400> SEQUENCE: 309

Thr Asn Leu Arg Ile Lys Phe Val Lys Leu His Thr
1               5                   10

<210> SEQ ID NO 310
<211> LENGTH: 12
<212> TYPE: PRT
<213> ORGANISM: artificial sequence -continued

```
<220> FEATURE:
<223> OTHER INFORMATION: synthetic peptide

<400> SEQUENCE: 310

Thr Ser Ala Glu Ala Tyr Asn Leu Leu Leu Arg Thr
1               5                   10

<210> SEQ ID NO 311
<211> LENGTH: 12
<212> TYPE: PRT
<213> ORGANISM: artificial sequence
<220> FEATURE:
<223> OTHER INFORMATION: synthetic peptide

<400> SEQUENCE: 311

Thr Ser Ile Lys Ile Arg Gly Thr Tyr Ser Glu Arg
1               5                   10

<210> SEQ ID NO 312
<211> LENGTH: 10
<212> TYPE: PRT
<213> ORGANISM: artificial sequence
<220> FEATURE:
<223> OTHER INFORMATION: synthetic peptide

<400> SEQUENCE: 312

Thr Thr Ser Trp Ser Gln Cys Ser Lys Ser
1               5                   10

<210> SEQ ID NO 313
<211> LENGTH: 12
<212> TYPE: PRT
<213> ORGANISM: artificial sequence
<220> FEATURE:
<223> OTHER INFORMATION: synthetic peptide

<400> SEQUENCE: 313

Thr Val Phe Ser Val Asp Gln Asp Asn Met Leu Glu
1               5                   10

<210> SEQ ID NO 314
<211> LENGTH: 17
<212> TYPE: PRT
<213> ORGANISM: artificial sequence
<220> FEATURE:
<223> OTHER INFORMATION: synthetic peptide

<400> SEQUENCE: 314

Thr Trp Ser Lys Val Gly Gly His Leu Arg Pro Gly Ile Val Gln Ser
1               5                   10                  15

Gly

<210> SEQ ID NO 315
<211> LENGTH: 12
<212> TYPE: PRT
<213> ORGANISM: artificial sequence
<220> FEATURE:
<223> OTHER INFORMATION: synthetic peptide

<400> SEQUENCE: 315

Thr Trp Ser Gln Lys Ala Leu His His Arg Val Pro
1               5                   10

<210> SEQ ID NO 316
<211> LENGTH: 12
<212> TYPE: PRT
```

```
<213> ORGANISM: artificial sequence
<220> FEATURE:
<223> OTHER INFORMATION: synthetic peptide

<400> SEQUENCE: 316

Thr Trp Tyr Lys Ile Ala Phe Gln Arg Asn Arg His
1               5                   10

<210> SEQ ID NO 317
<211> LENGTH: 12
<212> TYPE: PRT
<213> ORGANISM: artificial sequence
<220> FEATURE:
<223> OTHER INFORMATION: synthetic peptide

<400> SEQUENCE: 317

Thr Trp Tyr Lys Ile Ala Phe Gln Arg Asn Arg Lys
1               5                   10

<210> SEQ ID NO 318
<211> LENGTH: 10
<212> TYPE: PRT
<213> ORGANISM: artificial sequence
<220> FEATURE:
<223> OTHER INFORMATION: synthetic peptide

<400> SEQUENCE: 318

Thr Tyr Arg Ile Trp Arg Asp Thr Ala Asn
1               5                   10

<210> SEQ ID NO 319
<211> LENGTH: 11
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: seleneocysteine

<400> SEQUENCE: 319

Xaa Glu Gln Leu Glu Arg Ala Leu Asn Ser Ser
1               5                   10

<210> SEQ ID NO 320
<211> LENGTH: 9
<212> TYPE: PRT
<213> ORGANISM: artificial sequence
<220> FEATURE:
<223> OTHER INFORMATION: synthetic peptide

<400> SEQUENCE: 320

Val Ala Glu Ile Asp Gly Ile Glu Leu
1               5

<210> SEQ ID NO 321
<211> LENGTH: 14
<212> TYPE: PRT
<213> ORGANISM: artificial sequence
<220> FEATURE:
<223> OTHER INFORMATION: synthetic peptide

<400> SEQUENCE: 321

Val Glu His Asp Lys Glu Phe Phe His Pro Arg Tyr His His
1               5                   10
```

```
<210> SEQ ID NO 322
<211> LENGTH: 8
<212> TYPE: PRT
<213> ORGANISM: artificial sequence
<220> FEATURE:
<223> OTHER INFORMATION: synthetic peptide

<400> SEQUENCE: 322

Val Phe Asp Asn Phe Val Leu Lys
1               5

<210> SEQ ID NO 323
<211> LENGTH: 6
<212> TYPE: PRT
<213> ORGANISM: artificial sequence
<220> FEATURE:
<223> OTHER INFORMATION: synthetic peptide

<400> SEQUENCE: 323

Val Gly Val Ala Pro Gly
1               5

<210> SEQ ID NO 324
<211> LENGTH: 12
<212> TYPE: PRT
<213> ORGANISM: artificial sequence
<220> FEATURE:
<223> OTHER INFORMATION: synthetic peptide

<400> SEQUENCE: 324

Val Ile Leu Gln Gln Ser Ala Ala Asp Ile Ala Arg
1               5                   10

<210> SEQ ID NO 325
<211> LENGTH: 12
<212> TYPE: PRT
<213> ORGANISM: artificial sequence
<220> FEATURE:
<223> OTHER INFORMATION: synthetic peptide

<400> SEQUENCE: 325

Val Ile Arg Asp Ser Asn Val Val Gln Leu Asp Val
1               5                   10

<210> SEQ ID NO 326
<211> LENGTH: 10
<212> TYPE: PRT
<213> ORGANISM: artificial sequence
<220> FEATURE:
<223> OTHER INFORMATION: synthetic peptide

<400> SEQUENCE: 326

Val Ile Thr Val Lys Asp Ile Asn Asp Asn
1               5                   10

<210> SEQ ID NO 327
<211> LENGTH: 12
<212> TYPE: PRT
<213> ORGANISM: artificial sequence
<220> FEATURE:
<223> OTHER INFORMATION: synthetic peptide

<400> SEQUENCE: 327

Val Leu Ile Lys Gly Gly Arg Ala Arg Lys His Val
1               5                   10

<210> SEQ ID NO 328
```

```
<211> LENGTH: 12
<212> TYPE: PRT
<213> ORGANISM: artificial sequence
<220> FEATURE:
<223> OTHER INFORMATION: synthetic peptide

<400> SEQUENCE: 328

Val Leu Leu Gln Ala Asn Asp Gly Ala Gly Glu Phe
1               5                   10

<210> SEQ ID NO 329
<211> LENGTH: 12
<212> TYPE: PRT
<213> ORGANISM: artificial sequence
<220> FEATURE:
<223> OTHER INFORMATION: synthetic peptide

<400> SEQUENCE: 329

Val Leu Val Arg Val Glu Arg Ala Thr Val Phe Ser
1               5                   10

<210> SEQ ID NO 330
<211> LENGTH: 12
<212> TYPE: PRT
<213> ORGANISM: artificial sequence
<220> FEATURE:
<223> OTHER INFORMATION: synthetic peptide

<400> SEQUENCE: 330

Val Gln Leu Arg Asn Gly Phe Pro Tyr Phe Ser Tyr
1               5                   10

<210> SEQ ID NO 331
<211> LENGTH: 12
<212> TYPE: PRT
<213> ORGANISM: artificial sequence
<220> FEATURE:
<223> OTHER INFORMATION: synthetic peptide

<400> SEQUENCE: 331

Val Arg Trp Gly Met Gln Gln Ile Gln Leu Val Val
1               5                   10

<210> SEQ ID NO 332
<211> LENGTH: 25
<212> TYPE: PRT
<213> ORGANISM: artificial sequence
<220> FEATURE:
<223> OTHER INFORMATION: synthetic peptide

<400> SEQUENCE: 332

Val Ser Pro Pro Arg Arg Ala Arg Val Thr Asp Ala Thr Glu Thr Thr
1               5                   10                  15

Ile Thr Ile Ser Trp Arg Thr Lys Thr
            20                  25

<210> SEQ ID NO 333
<211> LENGTH: 15
<212> TYPE: PRT
<213> ORGANISM: artificial sequence
<220> FEATURE:
<223> OTHER INFORMATION: synthetic peptide

<400> SEQUENCE: 333

Val Val Ile Asp Ala Ser Thr Ala Ile Asp Ala Pro Ser Asn Leu
1               5                   10                  15
```

<210> SEQ ID NO 334
<211> LENGTH: 13
<212> TYPE: PRT
<213> ORGANISM: artificial sequence
<220> FEATURE:
<223> OTHER INFORMATION: synthetic peptide

<400> SEQUENCE: 334

Val Val Ser Leu Tyr Asn Phe Glu Gln Thr Phe Met Leu
1               5                   10

<210> SEQ ID NO 335
<211> LENGTH: 20
<212> TYPE: PRT
<213> ORGANISM: artificial sequence
<220> FEATURE:
<223> OTHER INFORMATION: synthetic peptide

<400> SEQUENCE: 335

Trp Cys Ser Arg Ala Arg Lys Gln Ala Ala Ser Ile Lys Val Ala Val
1               5                   10                  15

Ser Ala Asp Arg
            20

<210> SEQ ID NO 336
<211> LENGTH: 8
<212> TYPE: PRT
<213> ORGANISM: artificial sequence
<220> FEATURE:
<223> OTHER INFORMATION: synthetic peptide

<400> SEQUENCE: 336

Trp Gln Pro Pro Arg Ala Arg Ile
1               5

<210> SEQ ID NO 337
<211> LENGTH: 19
<212> TYPE: PRT
<213> ORGANISM: artificial sequence
<220> FEATURE:
<223> OTHER INFORMATION: synthetic peptide

<400> SEQUENCE: 337

Trp Gln Pro Pro Arg Ala Arg Ile Thr Gly Tyr Ile Ile Lys Tyr Glu
1               5                   10                  15

Lys Pro Gly

<210> SEQ ID NO 338
<211> LENGTH: 12
<212> TYPE: PRT
<213> ORGANISM: artificial sequence
<220> FEATURE:
<223> OTHER INFORMATION: synthetic peptide

<400> SEQUENCE: 338

Trp Thr Ile Gln Thr Thr Val Asp Arg Gly Leu Leu
1               5                   10

<210> SEQ ID NO 339
<211> LENGTH: 20
<212> TYPE: PRT
<213> ORGANISM: artificial sequence
<220> FEATURE:
<223> OTHER INFORMATION: synthetic peptide -continued

```
<400> SEQUENCE: 339

Trp Thr Pro Pro Arg Ala Gln Ile Thr Gly Tyr Arg Leu Thr Val Gly
1               5                   10                  15

Leu Thr Arg Arg
            20

<210> SEQ ID NO 340
<211> LENGTH: 13
<212> TYPE: PRT
<213> ORGANISM: artificial sequence
<220> FEATURE:
<223> OTHER INFORMATION: synthetic peptide

<400> SEQUENCE: 340

Trp Val Thr Val Thr Leu Asp Leu Arg Gln Val Phe Gln
1               5                   10

<210> SEQ ID NO 341
<211> LENGTH: 12
<212> TYPE: PRT
<213> ORGANISM: artificial sequence
<220> FEATURE:
<223> OTHER INFORMATION: synthetic peptide

<400> SEQUENCE: 341

Tyr Ala Ile Phe Leu Asn Lys Gly Arg Leu Glu Val
1               5                   10

<210> SEQ ID NO 342
<211> LENGTH: 9
<212> TYPE: PRT
<213> ORGANISM: artificial sequence
<220> FEATURE:
<223> OTHER INFORMATION: synthetic peptide

<400> SEQUENCE: 342

Tyr Cys Trp Ser Gln Tyr Leu Cys Tyr
1               5

<210> SEQ ID NO 343
<211> LENGTH: 19
<212> TYPE: PRT
<213> ORGANISM: artificial sequence
<220> FEATURE:
<223> OTHER INFORMATION: synthetic peptide

<400> SEQUENCE: 343

Tyr Glu Lys Pro Gly Ser Pro Pro Arg Glu Val Val Pro Arg Pro Arg
1               5                   10                  15

Pro Gly Val

<210> SEQ ID NO 344
<211> LENGTH: 12
<212> TYPE: PRT
<213> ORGANISM: artificial sequence
<220> FEATURE:
<223> OTHER INFORMATION: synthetic peptide

<400> SEQUENCE: 344

Tyr Phe Asp Gly Thr Gly Phe Ala Lys Ala Val Gly
1               5                   10

<210> SEQ ID NO 345
<211> LENGTH: 5
```

```
<212> TYPE: PRT
<213> ORGANISM: artificial sequence
<220> FEATURE:
<223> OTHER INFORMATION: synthetic peptide

<400> SEQUENCE: 345

Tyr Ile Gly Ser Arg
1               5

<210> SEQ ID NO 346
<211> LENGTH: 10
<212> TYPE: PRT
<213> ORGANISM: artificial sequence
<220> FEATURE:
<223> OTHER INFORMATION: synthetic peptide

<400> SEQUENCE: 346

Tyr Ile Leu His Val Ala Val Thr Asn Tyr
1               5                   10

<210> SEQ ID NO 347
<211> LENGTH: 12
<212> TYPE: PRT
<213> ORGANISM: artificial sequence
<220> FEATURE:
<223> OTHER INFORMATION: synthetic peptide

<400> SEQUENCE: 347

Tyr Ile Arg Leu Arg Leu Gln Arg Ile Arg Thr Leu
1               5                   10

<210> SEQ ID NO 348
<211> LENGTH: 16
<212> TYPE: PRT
<213> ORGANISM: artificial sequence
<220> FEATURE:
<223> OTHER INFORMATION: synthetic peptide

<400> SEQUENCE: 348

Tyr Arg Ser Arg Lys Tyr Ser Ser Trp Tyr Val Ala Leu Lys Arg Lys
1               5                   10                  15

<210> SEQ ID NO 349
<211> LENGTH: 32
<212> TYPE: PRT
<213> ORGANISM: artificial sequence
<220> FEATURE:
<223> OTHER INFORMATION: synthetic peptide

<400> SEQUENCE: 349

Tyr Arg Ser Arg Lys Tyr Ser Ser Trp Tyr Val Ala Leu Lys Arg Lys
1               5                   10                  15

His Tyr Arg Ser Arg Lys Tyr Ser Ser Trp Tyr Val Ala Leu Lys Arg
                20                  25                  30

<210> SEQ ID NO 350
<211> LENGTH: 16
<212> TYPE: PRT
<213> ORGANISM: artificial sequence
<220> FEATURE:
<223> OTHER INFORMATION: synthetic peptide

<400> SEQUENCE: 350

Tyr Arg Val Arg Val Thr Pro Lys Glu Lys Thr Gly Pro Met Lys Glu
1               5                   10                  15
```

```
<210> SEQ ID NO 351
<211> LENGTH: 19
<212> TYPE: PRT
<213> ORGANISM: artificial sequence
<220> FEATURE:
<223> OTHER INFORMATION: synthetic peptide

<400> SEQUENCE: 351

Tyr Ser Met Lys Lys Thr Thr Met Lys Ile Ile Pro Phe Asn Arg Leu
1               5                   10                  15

Thr Ile Gly

<210> SEQ ID NO 352
<211> LENGTH: 10
<212> TYPE: PRT
<213> ORGANISM: artificial sequence
<220> FEATURE:
<223> OTHER INFORMATION: synthetic peptide

<400> SEQUENCE: 352

Tyr Thr Ala Leu Ile Ile Ala Thr Asp Asn
1               5                   10

<210> SEQ ID NO 353
<211> LENGTH: 12
<212> TYPE: PRT
<213> ORGANISM: artificial sequence
<220> FEATURE:
<223> OTHER INFORMATION: synthetic peptide

<400> SEQUENCE: 353

Tyr Tyr Ala Ile Ser Asp Phe Ala Val Gly Gly Arg
1               5                   10
```